United States Patent [19]
Peterson et al.

[11] Patent Number: 5,529,921
[45] Date of Patent: Jun. 25, 1996

[54] IN VITRO ACTIVATION OF CYTOTOXIC T-CELLS USING INSECT CELLS EXPRESSING HUMAN CLASS I MHC AND β2-MICROGLOBULIN

[75] Inventors: Per A. Peterson, La Jolla; Michael Jackson; Pierre Langlade-Demoyen, both of Del Mar, all of Calif.

[73] Assignee: Scripps Research Institute, La Jolla, Calif.

[21] Appl. No.: 209,797

[22] Filed: Mar. 10, 1994

Related U.S. Application Data

[62] Division of Ser. No. 841,662, Feb. 19, 1992, Pat. No. 5,314,813.
[51] Int. Cl.$^6$ .............................. C12N 5/16; C12N 5/22; C12N 15/00
[52] U.S. Cl. .................... 435/240.2; 435/240.1; 435/252.3; 435/320.1
[58] Field of Search ............................ 435/240.1, 252.3, 435/320.1, 240.2; 424/534

[56] References Cited

PUBLICATIONS

ATCC Catalogue pp. 47, 48, 72 & 73 (1992).
Osband et al Immunology Today 11(6):193–195 (1990).
Basse et al. Cancer Immunol. Immunother. 34:221–227 (1992).
Levy et al. Int. Imm. 2(10):995–1002 (1990).
Angelichio et al NAR 19(18):5037–5043 (1991).

*Primary Examiner*—Donald E. Adams
*Attorney, Agent, or Firm*—Townsend and Townsend and Crew

[57] ABSTRACT

The present invention relates to a rational, elegant means of producing, loading and using Class I molecules to specifically activate CD8 cells in vitro, and their therapeutic applications in the treatment of a variety of conditions, including cancer, tumors or neoplasias, as well as viral, retroviral, autoimmune, and autoimmune-type diseases. The present invention also relates to vectors, cell lines, recombinant DNA molecules encoding human β2 microglobulin or Class I MHC molecules in soluble and insoluble form, and methods of producing same.

12 Claims, 19 Drawing Sheets

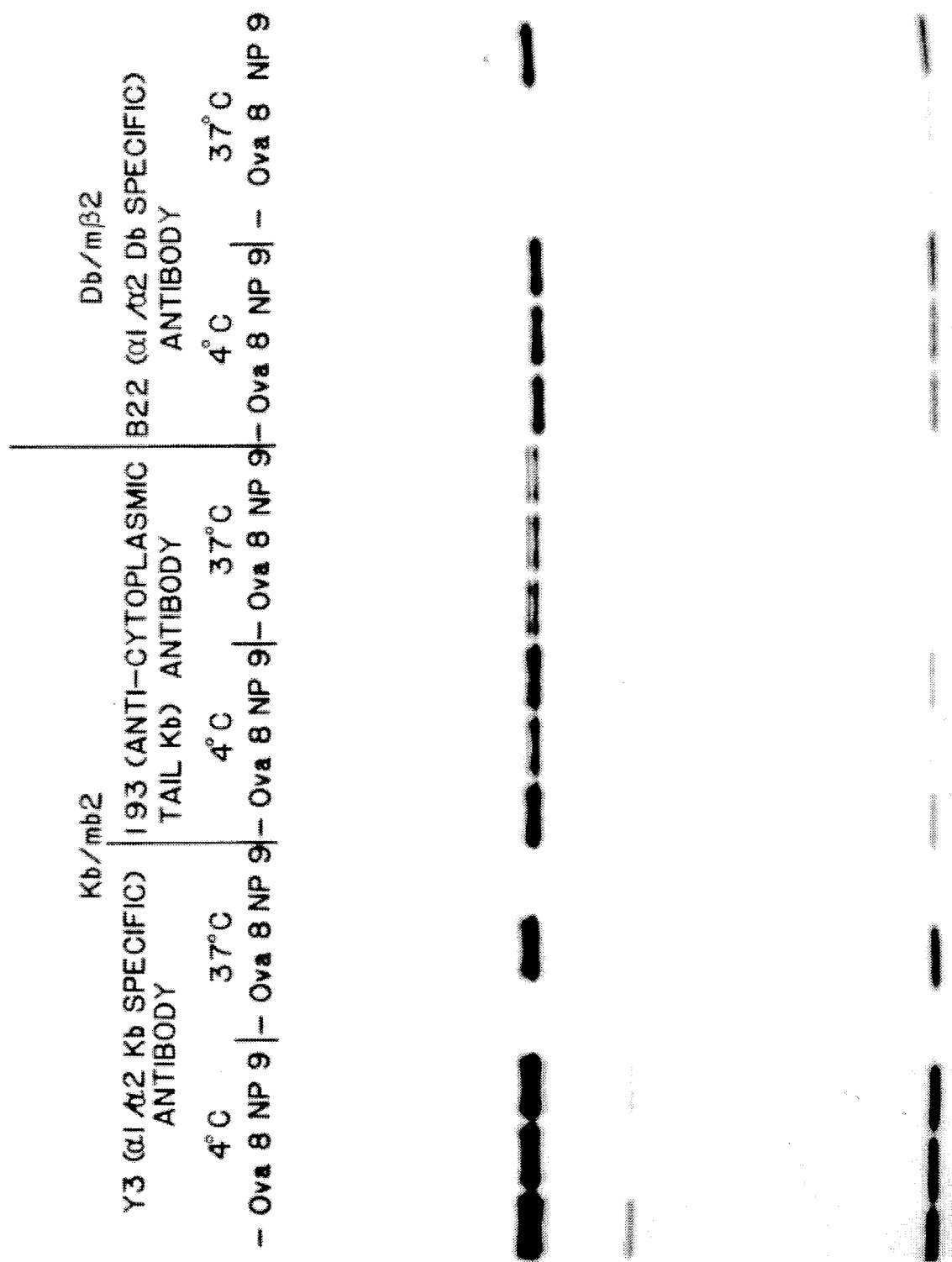

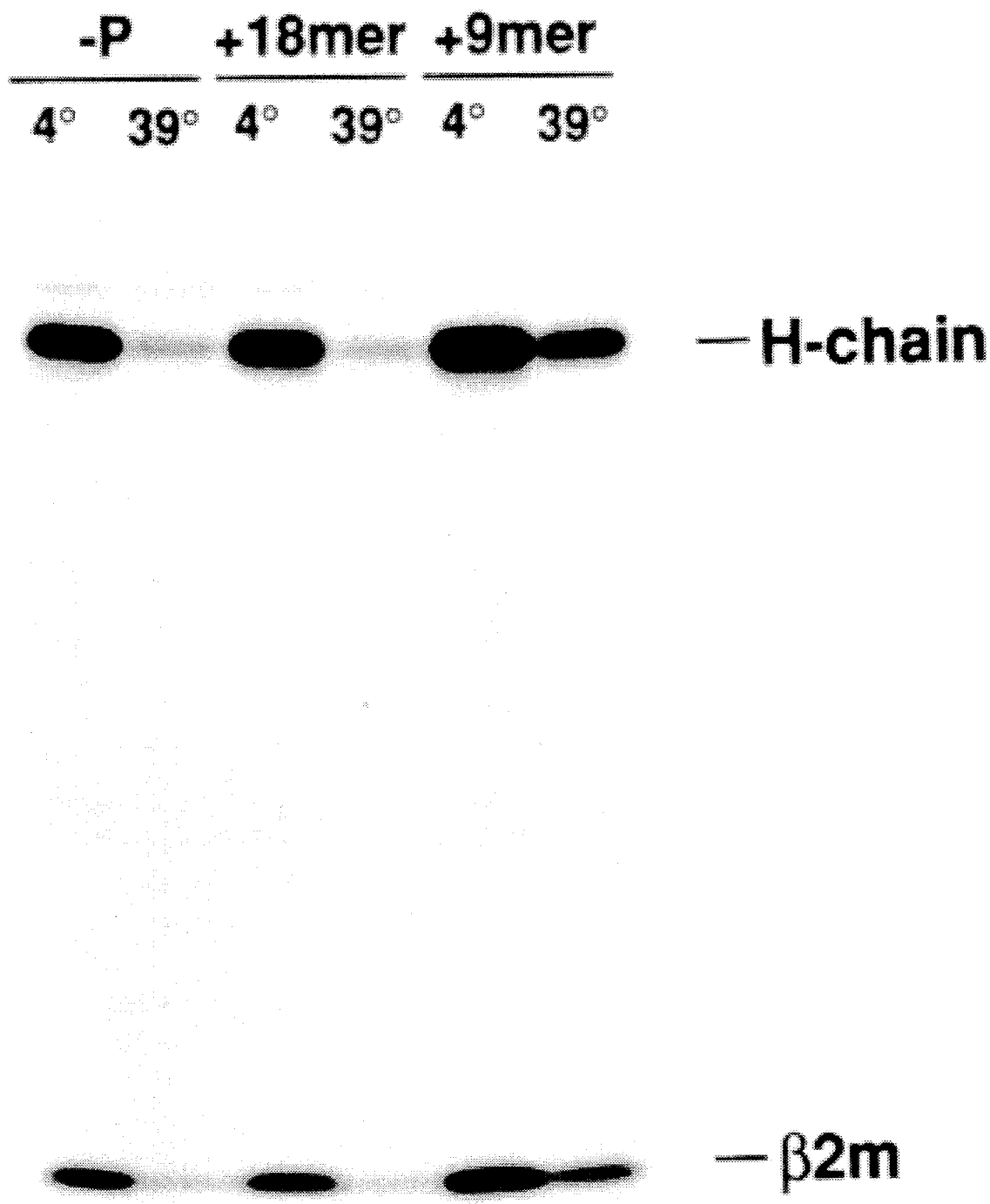

STABILISATION OF HLA A2.2 IN TRITON X100 LYSATES BY PEPTIDE
| 4°C | 37°C | 37°C | 37°C | 37°C | 37°C |
|---|---|---|---|---|---|
| A | B | C | D | E | F |
 — HEAVY CHAIN
 —β2M
FIG. 5C

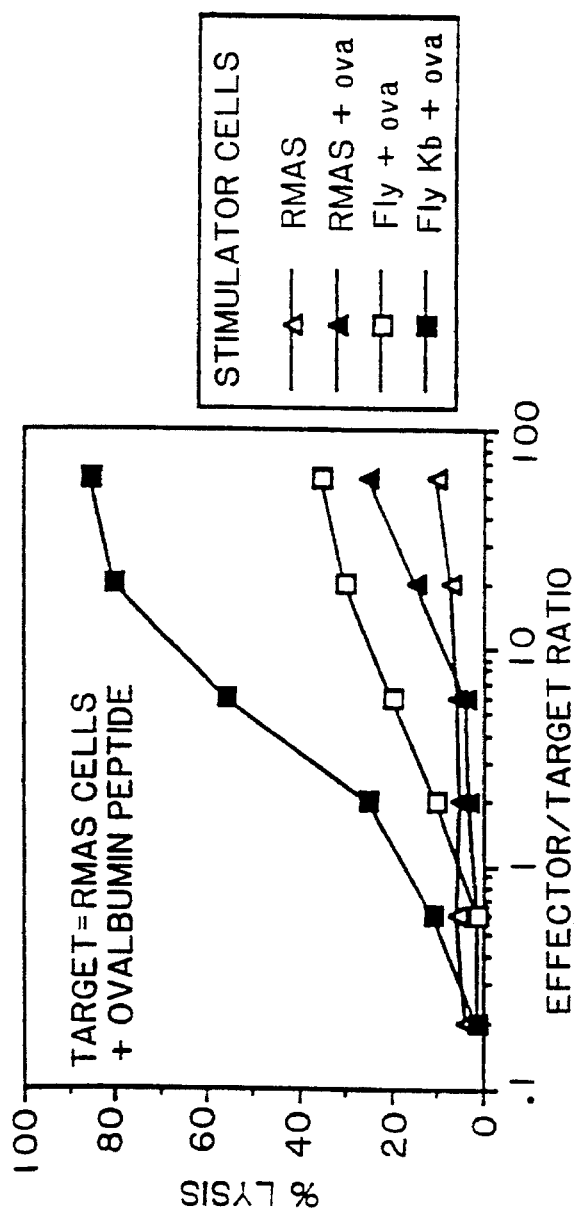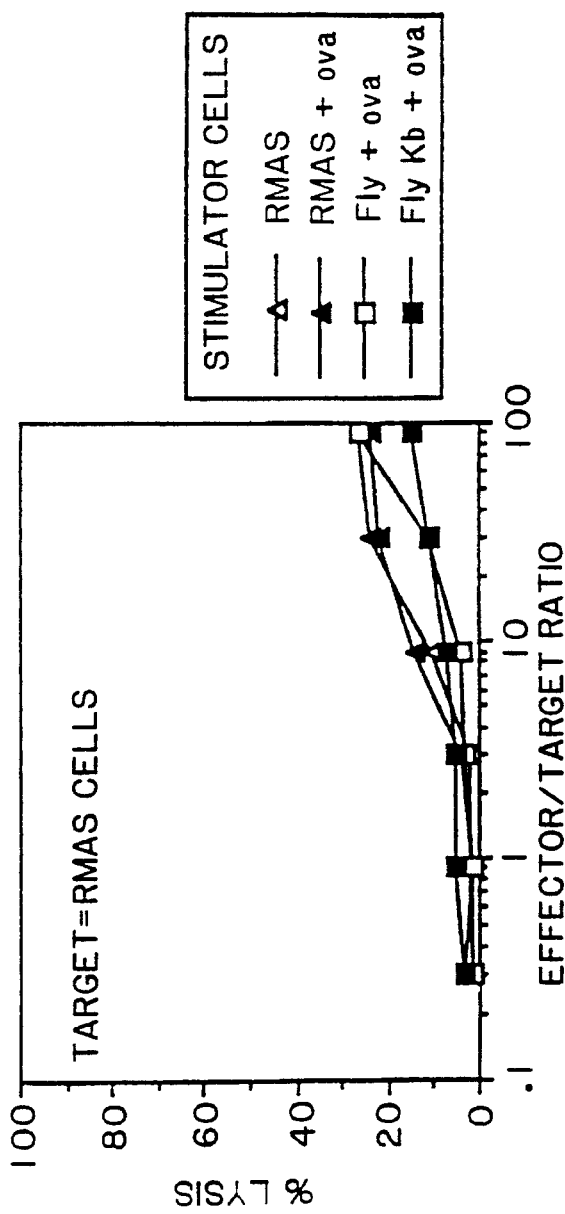

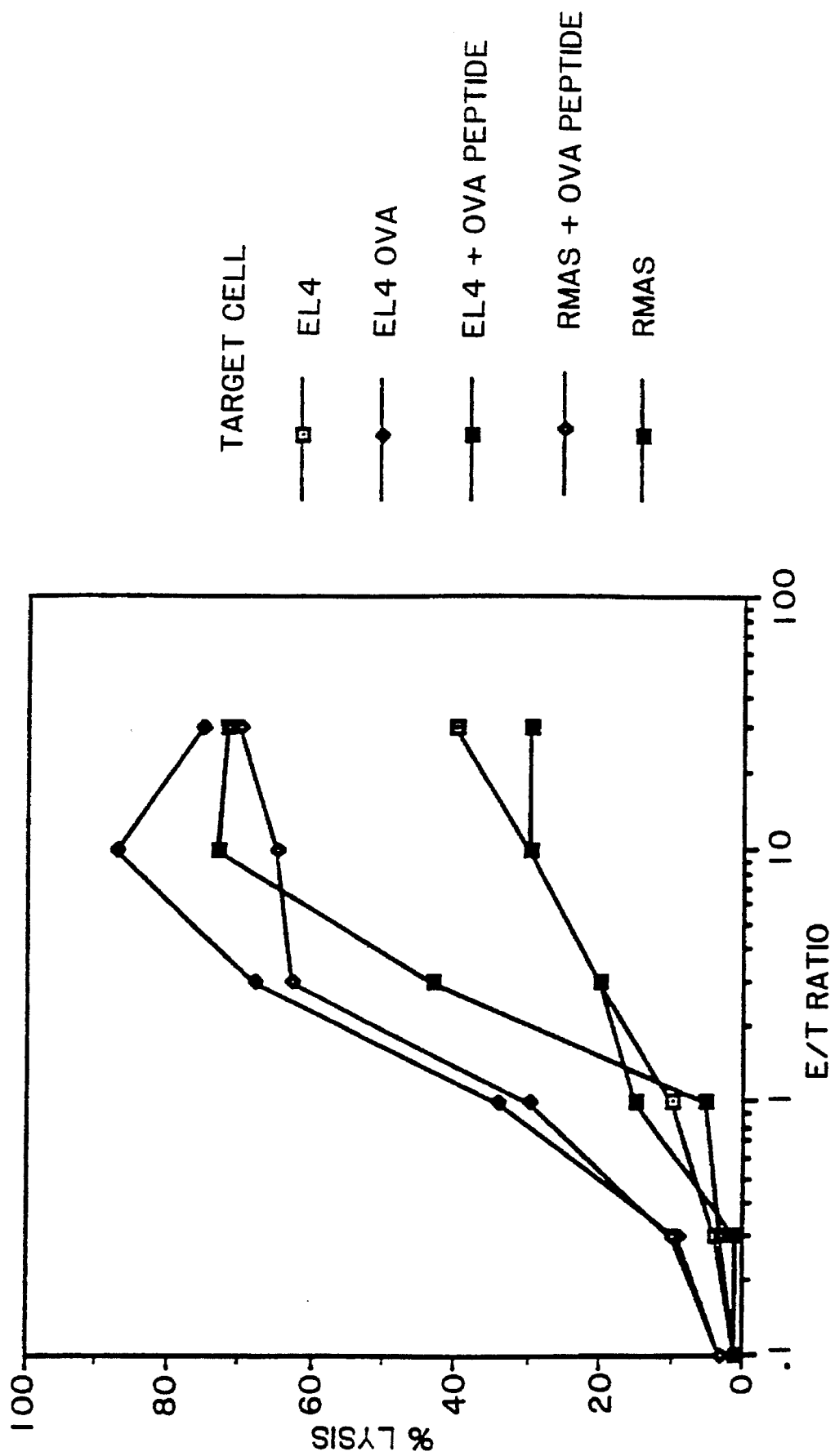

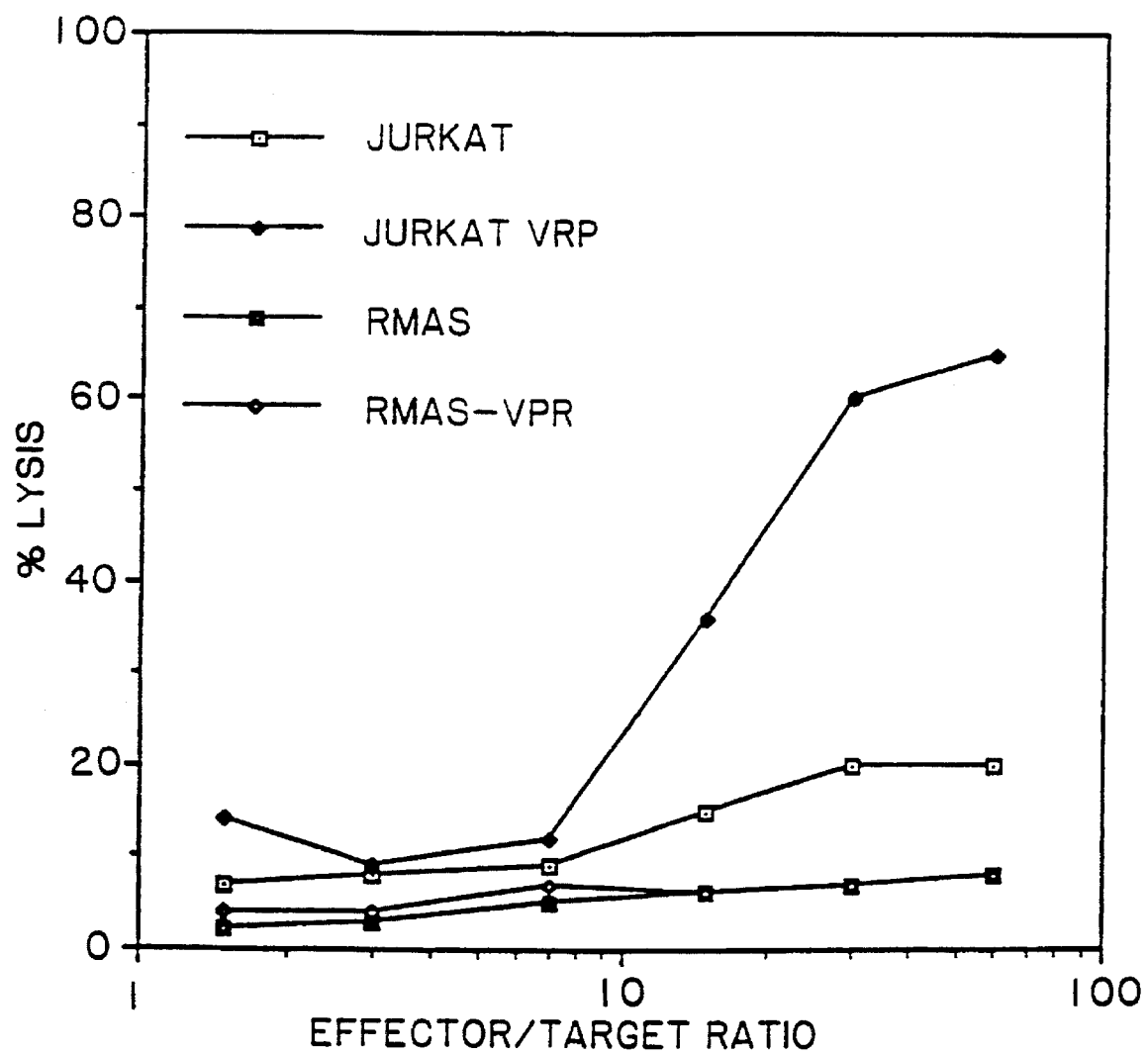
FIG.IOC

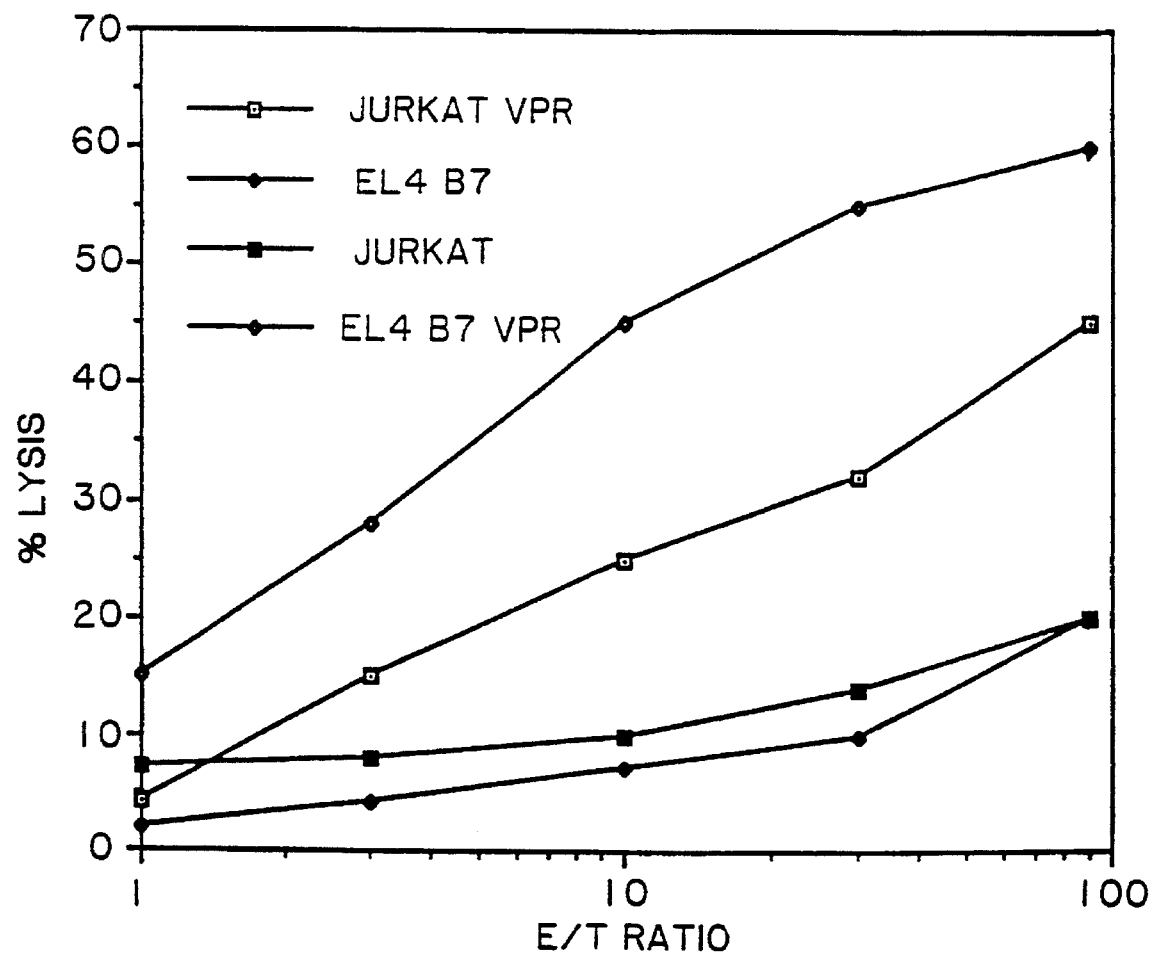
FIG.IIA

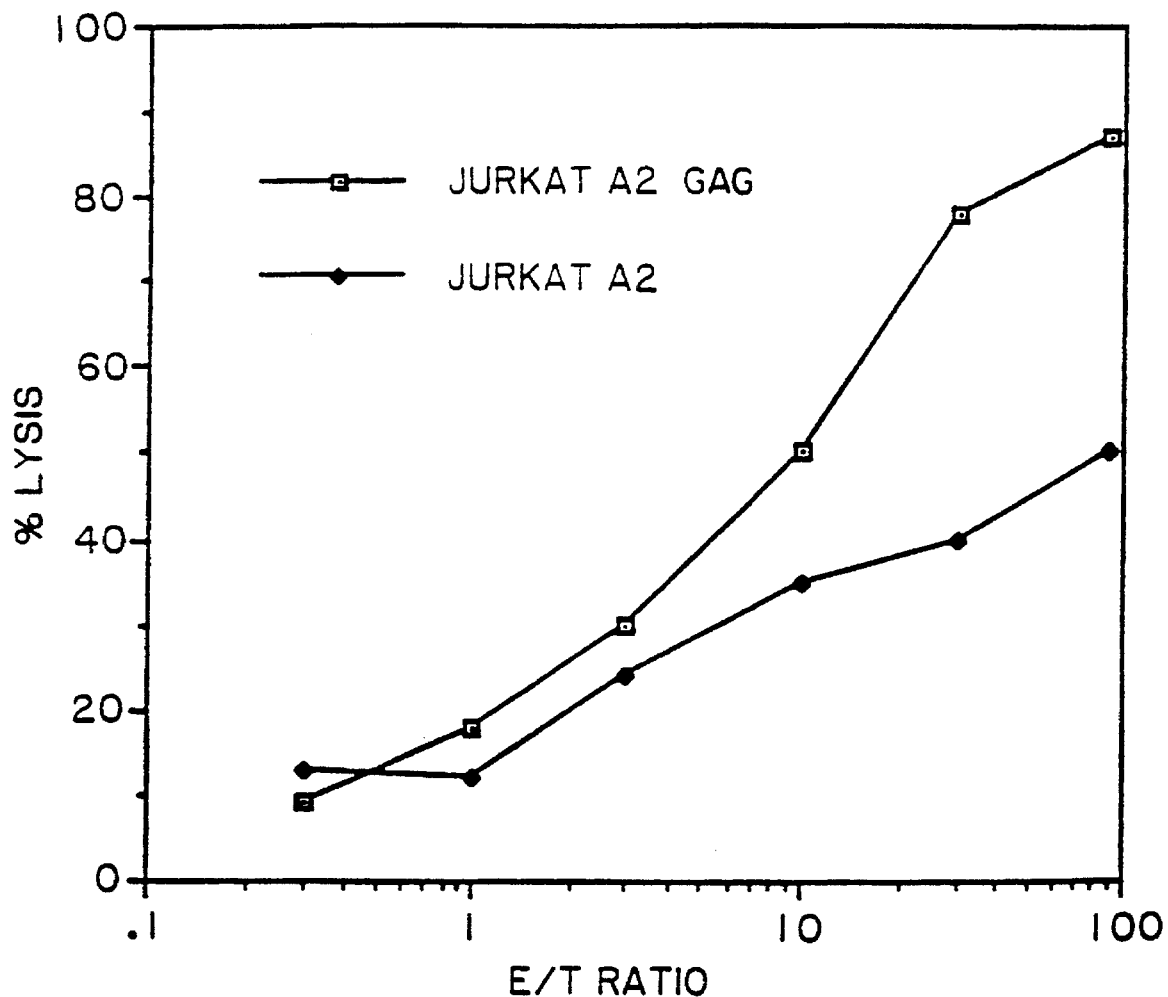
FIG. IIB

SEQUENCE LISTING ( 1 ) GENERAL INFORMATION:

( i i i ) NUMBER OF SEQUENCES: 36

( 2 ) INFORMATION FOR SEQ ID NO:1:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:1:

CCACCATGGC CGTCATGGCG CCC 23

( 2 ) INFORMATION FOR SEQ ID NO:2:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:2:

GGTCACACTT TACAAGCTCT GAG 23

( 2 ) INFORMATION FOR SEQ ID NO:3:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:3:

CCACCATGCT GGTCATGGCG CCC 23

( 2 ) INFORMATION FOR SEQ ID NO:4:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:4:

GGACTCGATG TGAGAGACAC ATC 23

( 2 ) INFORMATION FOR SEQ ID NO:5:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:5:

CCACCATGCG GGTCATGGCG CCC 23

( 2 ) INFORMATION FOR SEQ ID NO:6:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:6:

GGTCAGGCTT TACAAGCGAT GAG 23

( 2 ) INFORMATION FOR SEQ ID NO:7:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:7:

CCACCATGCG GGTAGATGCC CTC 23

( 2 ) INFORMATION FOR SEQ ID NO:8:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:8:

GGTTACAAGC TGTGAGACTC AGA    23

(2) INFORMATION FOR SEQ ID NO:9:

( i ) SEQUENCE CHARACTERISTICS:
    ( A ) LENGTH: 23 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:9:

CCACCATGGC GCCCCGAAGC CTC    23

(2) INFORMATION FOR SEQ ID NO:10:

( i ) SEQUENCE CHARACTERISTICS:
    ( A ) LENGTH: 23 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:10:

GGTCACACTT TATTAGCTGT GAG    23

(2) INFORMATION FOR SEQ ID NO:11:

( i ) SEQUENCE CHARACTERISTICS:
    ( A ) LENGTH: 23 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:11:

CCACCATGGC GCCCCGAACC CTC    23

(2) INFORMATION FOR SEQ ID NO:12:

( i ) SEQUENCE CHARACTERISTICS:
    ( A ) LENGTH: 23 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:12:

GGTCACAATT TACAAGCCGA GAG    23

( 2 ) INFORMATION FOR SEQ ID NO:13:

( i ) SEQUENCE CHARACTERISTICS:
    ( A ) LENGTH: 427 base pairs
    ( B ) TYPE: nucleic acid
    ( C ) STRANDEDNESS: double
    ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:13:

```
AATTCGTTGC  AGGACAGGAT  GTGGTGCCCG  ATGTGACTAG  CTCTTTGCTG  CAGGCCGTCC    60
TATCCTCTGG  TTCCGATAAG  AGACCCAGAA  CTCCGGCCCC  CCACCGCCCA  CCGCCACCCC   120
CATACATATG  TGGTACGCAA  GTAAGAGTGC  CTGCGCATGC  CCCATGTGCC  CCACCAAGAG   180
TTTTGCATCC  CATACAAGTC  CCCAAAGTGG  AGAACCGAAC  CAATTCTTCG  CGGGCAGAAC   240
AAAAGCTTCT  GCACACGTCT  CCACTCGAAT  TTGGAGCCGG  CCGGCGTGTG  CAAAAGAGGT   300
GAATCGAACG  AAAGACCCGT  GTGTAAAGCC  GCGTTTCCAA  AATGTATAAA  ACCGAGAGCA   360
TCTGGCCAAT  GTGCATCAGT  TGTGGTCAGC  AGCAAAATCA  AGTGAATCAT  CTCAGTGCAA   420
CTAAAGG                                                                 427
```

( 2 ) INFORMATION FOR SEQ ID NO:14:

( i ) SEQUENCE CHARACTERISTICS:
    ( A ) LENGTH: 740 base pairs
    ( B ) TYPE: nucleic acid
    ( C ) STRANDEDNESS: double
    ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:14:

```
ATTCGATGCA  CACTCACATT  CTTCTCCTAA  TACGATAATA  AAACTTTCCA  TGAAAAATAT    60
GGAAAAATAT  ATGAAAATTG  AGAAATCCAA  AAAACTGATA  AACGCTCTAC  TTAATTAAAA   120
TAGATAAATG  GGAGCGGCTG  GAATGGCGGA  GCATGACCAA  GTTCCTCCGC  CAATCAGTCG   180
TAAAACAGAA  GTCGTGGAAA  GCGGATAGAA  AGAATGTTCG  ATTTGACGGG  CAAGCATGTC   240
TGCTATGTGG  CGGATTGCGG  AGGAATTGCA  CTGGAGACCA  GCAAGGTTCT  CATGACCAAG   300
AATATAGCGG  TGTGAGTGAG  CGGGAAGCTC  GGTTTCTGTC  CAGATCGAAC  TCAAAACTAG   360
TCCAGCCAGT  CGCTGTCGAA  ACTAATTAAG  TTAATGAGTT  TTTCATGTTA  GTTTCGCGCT   420
GAGCAACAAT  TAAGTTTATG  TTTCAGTTCG  GCTTAGATTT  CGCTGAAGGA  CTTGCCACTT   480
TCAATCAATA  CTTTAGAACA  AAATCAAAAC  TCATTCTAAT  AGCTTGGTGT  TCATCTTTTT   540
TTTTAATGAT  AAGCATTTTG  TCGTTTATAC  TTTTTATATT  TCGATATTAA  ACCACCTATG   600
AAGTTCATTT  TAATCGCCAG  ATAAGCAATA  TATTGTGTAA  ATATTTGTAT  TCTTTATCAG   660
GAAATTCAGG  GAGACGGGGA  AGTTACTATC  TACTAAAAGC  CAAACAATTT  CTTACAGTTT   720
TACTCTCTCT  ACTCTAGAGT                                                  740
```

( 2 ) INFORMATION FOR SEQ ID NO:15:

( i ) SEQUENCE CHARACTERISTICS:
    ( A ) LENGTH: 60 base pairs ( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:15:

GCTTGGATCC AGATCTACCA TGTCTCGCTC CGTGGCCTTA GCTGTGCTCG CGCTACTCTC    60

( 2 ) INFORMATION FOR SEQ ID NO:16:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:16:

GGATCCGGAT GGTTACATGT CGCGATCCCA CTTAAC    36

( 2 ) INFORMATION FOR SEQ ID NO:17:

( i ) SEQUENCE CHARACTERISTICS:
( A ) LENGTH: 19 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:17:

GGAGCCGTGA CTGACTGAG    19

( 2 ) INFORMATION FOR SEQ ID NO:18:

( i ) SEQUENCE CHARACTERISTICS:
( A ) LENGTH: 24 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:18:

CCCTCGGCAC TGACTGACTC CTAG    24

( 2 ) INFORMATION FOR SEQ ID NO:19:

( i ) SEQUENCE CHARACTERISTICS:
( A ) LENGTH: 26 base pairs
( B ) TYPE: nucleic acid
( C ) STRANDEDNESS: single
( D ) TOPOLOGY: linear (  i  i  )  MOLECULE TYPE: DNA (genomic)

(  i  i  i  )  HYPOTHETICAL: NO (  i  v  )  ANTI-SENSE: NO (  x  i  )  SEQUENCE DESCRIPTION: SEQ ID NO:19:

GCGGATCCAT GGCCGTCATG GCGCCC  26

( 2 ) INFORMATION FOR SEQ ID NO:20:

(  i  )  SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear (  i  i  )  MOLECULE TYPE: DNA (genomic)

(  i  i  i  )  HYPOTHETICAL: NO (  i  v  )  ANTI-SENSE: NO (  x  i  )  SEQUENCE DESCRIPTION: SEQ ID NO:20:

CGGAATTCTC ATCAGGGCTT CGGCAGCCC  29

( 2 ) INFORMATION FOR SEQ ID NO:21:

(  i  )  SEQUENCE CHARACTERISTICS:
        ( A ) LENGTH: 38 base pairs
        ( B ) TYPE: nucleic acid
        ( C ) STRANDEDNESS: double
        ( D ) TOPOLOGY: linear (  i  i  )  MOLECULE TYPE: cDNA (  i  i  i  )  HYPOTHETICAL: NO (  i  v  )  ANTI-SENSE: NO (  x  i  )  SEQUENCE DESCRIPTION: SEQ ID NO:21:

GGATCCTCTC AGACGCCGAG ATGCGGGTCA CGGCGCCC  38

( 2 ) INFORMATION FOR SEQ ID NO:22:

(  i  )  SEQUENCE CHARACTERISTICS:
        ( A ) LENGTH: 52 base pairs
        ( B ) TYPE: nucleic acid
        ( C ) STRANDEDNESS: single
        ( D ) TOPOLOGY: linear (  i  i  )  MOLECULE TYPE: DNA (genomic)

(  i  i  i  )  HYPOTHETICAL: NO (  i  v  )  ANTI-SENSE: NO (  x  i  )  SEQUENCE DESCRIPTION: SEQ ID NO:22:

AGCTTGAGCA CTTGTTCTTT TTGCAGAAGC TCAGAATAAA CGCTCAACTT TG  52

( 2 ) INFORMATION FOR SEQ ID NO:23:

(  i  )  SEQUENCE CHARACTERISTICS:
        ( A ) LENGTH: 24 amino acids
        ( B ) TYPE: amino acid
        ( C ) STRANDEDNESS: single
        ( D ) TOPOLOGY: linear (  i  i  )  MOLECULE TYPE: peptide (  i  i  i  )  HYPOTHETICAL: NO ( i v ) ANTI-SENSE: NO ( v ) FRAGMENT TYPE: internal ( x i ) SEQUENCE DESCRIPTION: SEQ ID NO:23:

```
Glu Gln Leu Glu Ser Ile Ile Asn Phe Glu Lys Leu Thr Glu Trp Thr
1               5                   10                  15
Ser Ser Asn Val Met Glu Glu Arg
            20
```

( 2 ) INFORMATION FOR SEQ ID NO:24:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:24:

```
Asp Leu Arg Gly Tyr Val Tyr Gln Gly Leu
1               5                   10
```

( 2 ) INFORMATION FOR SEQ ID NO:25:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v ) FRAGMENT TYPE: internal ( x i ) SEQUENCE DESCRIPTION: SEQ ID NO:25:

```
Ala Ser Asn Glu Asn Met Glu Thr Met
1               5
```

( 2 ) INFORMATION FOR SEQ ID NO:26:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:26:

```
Ser Glu Arg Pro Gln Ala Ser Gly Val Tyr Met Gly Asn Leu
1               5                   10
```

( 2 ) INFORMATION FOR SEQ ID NO:27:

( i ) SEQUENCE CHARACTERISTICS:
    ( A ) LENGTH: 14 amino acids
    ( B ) TYPE: amino acid
    ( C ) STRANDEDNESS: single
    ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:27:

Asp Ser Ser Gly Val Glu Asn Pro Gly Gly Tyr Cys Thr Lys
 1               5                   10

( 2 ) INFORMATION FOR SEQ ID NO:28:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:28:

Gln Met Lys Asp Cys Thr Glu Arg Gln
     1               5

( 2 ) INFORMATION FOR SEQ ID NO:29:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:29:

Lys Arg Trp Ile Ile Leu Gly Leu Asn
     1               5

( 2 ) INFORMATION FOR SEQ ID NO:30:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:30:

Phe Arg Ile Gly Cys Arg His Ser Arg
1               5

( 2 ) INFORMATION FOR SEQ ID NO:31:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:31:

Ile Leu Lys Glu Pro Val His Gly Val
1               5

( 2 ) INFORMATION FOR SEQ ID NO:32:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:32:

Ile Leu Gly Phe Val Phe Thr Leu Thr Val
1               5                   10

( 2 ) INFORMATION FOR SEQ ID NO:33:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:33:

Leu Pro Asp Cys Lys Val Met Val His Asp Pro Ser Leu Ala
1               5                   10

( 2 ) INFORMATION FOR SEQ ID NO:34:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:34:

ATATGGATCC TCACCATCTC AGGGTGAGGG GC    32

( 2 ) INFORMATION FOR SEQ ID NO:35:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:35:

Arg Gly Tyr Val Tyr Gln Gly Leu Lys Ser
1               5                   10

( 2 ) INFORMATION FOR SEQ ID NO:36:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:36:

Phe Ala Pro Gly Asn Tyr Pro Ala Leu
1               5

IN VITRO ACTIVATION OF CYTOTOXIC T-CELLS USING INSECT CELLS EXPRESSING HUMAN CLASS I MHC AND β2-MICROGLOBULIN

This invention was made with the support of the Government of the United States of America, and the Government of the United States of America has certain rights in the invention.

This is a Division of application Ser. No. 07/841,662 filed Feb. 19, 1992 now U.S. Pat. No. 5,314,813.

TECHNICAL FIELD

The present invention relates to methods of activating CD8 cells in vitro with specificity for particular antigenic peptides, the use of activated CD8 cells in vivo for the treatment of a variety of disease conditions, and compositions appropriate for these USES.

BACKGROUND

The efficiency with which the immune system cures or protects individuals from infectious disease has always been intriguing to scientists, as it has been believed that it might be possible to activate the immune system to combat other types of diseases. Such diseases include cancer, AIDS, hepatitis and infectious disease in immunosuppressed patients. While various procedures involving the use of antibodies have been applied in those types of diseases, few if any successful attempts using cytotoxic T cells have been recorded. Theoretically, cytotoxic T cells would be the preferable means of treating the types of disease noted above. However, no in vitro procedures have been available to specifically activate cytotoxic T cells.

Cytotoxic T cells, or CD8 cells as they are presently known, represent the main line of defense against viral infections. CD8 lymphocytes specifically recognize and kill cells which are infected by a virus. Thus, the cost of eliminating a viral infection is the accompanying loss of the infected cells. The T cell receptors on the surface of CD8 cells cannot recognize foreign antigens directly. In contrast to antibodies, antigen must first be presented to the receptors.

The presentation of antigen to T cells is accomplished by major histocompatibility complex (MHC) molecules of the Class I type. The major histocompatibility complex (MHC) refers to a large genetic locus encoding an extensive family of glycoproteins which play an important role in the immune response. The MHC genes, which are also referred to as the HLA (human leucocyte antigen) complex, are located on chromosome 6 in humans. The molecules encoded by MHC genes are present on cell surfaces and are largely responsible for recognition of tissue transplants as "non-self". Thus, membrane-bound MHC molecules are intimately involved in recognition of antigens by T cells.

MHC products are grouped into three major classes, referred to as I, II, and III. T cells that serve mainly as helper cells express CD4 and are primarily restricted by Class II molecules, whereas CD8 expressing cells, which mostly represent cytotoxic effector cells, interact with Class I molecules.

Class I molecules are membrane glycoproteins with the ability to bind peptides derived primarily from intracellular degradation of endogenous proteins. Complexes of MHC molecules with peptides derived from viral, bacterial and other foreign proteins comprise the ligand that triggers the antigen responsiveness of T cells. In contrast, complexes of MHC molecules with peptides derived from normal cellular products play a role in "teaching" the T cells to tolerate self-peptides, in the thymus. Class I molecules do not present entire, intact antigens; rather, they present peptide fragments thereof, "loaded" onto their "peptide binding groove".

For many years, immunologists have hoped to raise specific cytotoxic cells targeting viruses, retroviruses and cancer cells. While targeting against viral diseases in general may be accomplished in vivo by vaccination with live or attenuated vaccines, no similar success has been achieved with retroviruses or with cancer cells. Moreover, the vaccine approach has not had the desired efficacy in immunosuppressed patients. One way around this difficulty would be to immunize a healthy individual, isolate the CD8 cells from this individual, and inject these CD8 cells into the disease-afflicted person. This experimental protocol seems to work in inbred mouse strains, but it has not been successfully tried in humans. There are several possible explanations. First of all, peptides are unique for a given MHC; in other words, certain antigenic peptides bind preferentially to particular MHC species and do not bind well to others, even in the absence of the "preferred" MHC molecule. Furthermore, MHC molecules are highly polymorphic, which fact generates at least two problems. First, the CD8 cells of an individual can only interact with peptides bound to precisely those three to six Class I molecules present in that individual. Second, CD8 cells react violently with all Class I molecules which are different from those expressed in the individual from whom the CD8 cells are obtained, regardless of what peptides the Class I molecules contain. This reactivity has been observed for some time and is termed allo-reactivity. It is the underlying cause of the immune rejection of transplanted organs.

Thus, apart from the rather heroic experimental protocol in which one individual is used as the donor of activated CD8 cells to another individual, it is difficult to find two unrelated persons with the exact same setup of Class I molecules. For this reason, at least one researcher has taken the rather non-specific approach of "boosting" existing CD8 cells by incubating them in vitro with IL-2, a growth factor for T cells. However, this protocol (known as LAK cell therapy) will only allow the expansion of those CD8 cells which are already activated. As the immune system is always active for one reason or another, most of the IL-2 stimulated cells will be irrelevant for the purpose of combatting the disease. In fact, it has not been documented that this type of therapy activates any cells with the desired specificity. Thus, the benefits of LAK cell therapy are controversial at best, and the side effects are typically so severe that many studies have been discontinued.

Several novel molecules which appear to be involved in the peptide loading process have recently been identified. It has also been noted that Class I molecules without bound peptide (i.e., "empty" molecules) can be produced under certain restrictive circumstances. These "empty" molecules are often unable to reach the cell surface, however, as Class I molecules without bound peptide are very thermolabile. Thus, the "empty" Class I molecules disassemble during their transport from the interior of the cell to the cell surface. This is an elegant means by which the immune system can ensure that only cells that are actively synthesizing viral proteins are destroyed. For example, when a virally infected cell is killed, it will release viral peptides. If neighboring cells were expressing "empty" Class I molecules—i.e., those without bound peptide—these cells would be coated with the released viral peptides. Since cytotoxic T cells (or CD8 cells) have no means of ascertaining how or why a peptide happens to be bound to a Class I molecule, cells which passively obtained a viral peptide coating would be killed as well as those which were actively synthesizing the viral proteins.

Viral peptides in vivo are broken down by a large particle known as the proteasome. This enzyme complex also breaks down normal, cellular proteins, which suggests that peptides derived from our own cellular proteins compete with virally-derived peptides for binding sites on Class I molecules. Thus, only some of the Class I molecules on the surface of a virally-infected cell would actually contain viral peptides, as the majority of the Class I molecules would contain peptides derived from our own, cellular proteins. As there are tens of thousands of Class I molecules on the surface of a cell, and as CD8 cells can recognize as few as 200 Class I molecules loaded with a given viral peptide, this competition between peptides derived from viruses and cellular proteins does not completely compromise the efficiency by which the CD8 cells can destroy a virally-infected cell. Nevertheless, if one were able to "engineer" cells to express Class I molecules displaying only one species of antigenic peptide—i.e., if all Class I molecules had the same peptide bound thereto—it would arguably increase the efficiency of CD8 activation.

Class I molecules bind peptides in a specific manner. All peptides have to be about 8–9 amino acids in length and their sequences must fit the peptide-binding pocket of the Class I molecules. In this respect, Class I molecules display some resemblance to antibodies. However, while a given antibody tends to bind only one antigen, a given Class I molecule can bind many hundred different peptides. As the number of viruses and other pathogens is quite large, it is apparent that our immune defense would be poor if we had only a single Class I molecule, even if it is capable of binding land altering many different peptides. For this reason, all humans have between three and six different Class I molecules, which can each bind many different types of peptides. Accordingly, the CD8 cells can recognize many thousands of peptides bound to one or another Class I molecule.

As selection seems to be the dominant force in evolution, pathogens emerge which cannot be recognized efficiently by the immune system. Thus, a viral sequence, which gives rise to peptides that bind efficiently to a variety of Class I molecules, may mutate such that it is not recognized by any of the three to six Class I molecules present in an individual. This virus may therefore not be recognized by the immune system and may consequently cause the death of the affected individual. If all individuals had an identical set of Class I molecules, such a virus might conceivably eliminate an entire species. However, individual variation is a safeguard against that possibility, as some 100 different forms of Class I molecules are present in the population. Thus, a mutated virus may injure some individuals, but it is unlikely to result in the extinction of an entire population, since different individuals possess different sets of Class I molecules.

If Class I molecules can bind a variety of peptides, including peptides derived from our own cellular proteins, one may wonder why the CD8 cells of the immune system do not recognize and destroy our own tissues. While the answer to this question is not entirely clear, two distinct mechanisms are presently believed to be operating. First, CD8 cells that can react with self-peptides are eliminated in the thymus. Second, CD8 cells become non-responsive (anergic) to self-peptides in the peripheral organs of the immune system. Since every possible type or epitope of cellular proteins is not synthesized by the cells in the thymus, the second mechanism would appear to be the more likely explanation. This mechanism appears to be operational for the level of self-peptides normally encountered. If this level is increased by some means, it can be shown that individuals do indeed have CD8 cells that can recognize and destroy cells expressing self-peptides. This latter observation is significant with regard to the concept of using the immune system to eliminate tumor cells.

BRIEF SUMMARY OF THE INVENTION

A more direct approach to solving the problems discussed above would be to directly and specifically stimulate only those CD8 cells which are relevant to combat the disease. Recent insights into the mechanisms which govern peptide loading onto Class I molecules have now permitted this. Thus, Class I molecules have been expressed in *Drosophila melanogaster* (fruit fly) cells. Since Drosophila does not have an immune system, the various proteins involved in the peptide loading machinery should be absent from such cells. It is now evident that the lack of peptide loading machinery allows the Class I molecules to be expressed as "empty" molecules at the cell surface.

Another advantage of using the Drosophila system is that Drosophila cells prefer a temperature of 28° C. rather than 37° C. This fact is very important, because "empty" Class I molecules are thermolabile and tend to disintegrate at 37° C. By incubating the Class I expressing Drosophila cells with peptides that can bind to the Class I molecule, it is possible to get every Class I molecule to contain one and the same peptide. The cells are accordingly very different from mammalian cells, where the Class I molecules contain many different types of peptides, most of which are derived from our own, innocuous cellular proteins.

Despite numerous, unsuccessful efforts over the years in hundreds of laboratories to specifically activate CD8 cells in vitro, it seems reasonable that the high level of expression of one Class I molecule containing a single peptide might override the need for in vivo stimulation of the immune system. By incubating the properly treated Drosophila cells with spleen or lymph node cells from unprimed mice (i.e., the mice had never previously encountered the peptides used), it is now feasible to generate cytotoxic T cells which are totally specific for the antigenic peptide. The cytotoxic response is usually three to five times stronger than what is obtained via previously-known methods.

While some examples herein present a "model" using murine Class I molecules, other examples are disclosed herein using human Class I molecules, or transgenic mice expressing human molecules. In one example, a peptide derived from the gag protein of HIV (the AIDS virus) is used. This combination of molecules works well; in fact, it works as well as experiments using a pure murine model. Moreover, the presently-disclosed system, which uses human molecules in a Drosophila system as presently disclosed, is much more versatile than the mouse system described in a recent paper by DeBruijn, et al. (*Eur. J. Immunol.* 21: 2963–70, 1991). In particular, the latter system requires enormous amounts of effector cells in order to effect killing and is less versatile than the presently-disclosed system. More importantly, the presently-disclosed system, unlike the mouse system, efficiently uses and activates responses against human molecules.

Most of the presently-disclosed experiments carried out to date have used the intact Drosophila cells. However, it is now demonstrated that empty, truncated molecules can be obtained from the Drosophila cells in good yields (approximately 1 mg/L). Such molecules might be useful in accomplishing immunosuppression in transplant patients and for treatment of patients with autoimmune diseases such as rheumatoid arthritis.

In summary, our long-term commitment aimed at understanding the details of how peptides are generated and loaded onto Class I molecules in vivo has stimulated the development of a rational and highly efficient means by which CD8 cells can become activated against peptides of our choice. It is our belief that the use of such activated cells may have a role in the treatment of a wide variety of disease states.

A rational, elegant means of producing, loading and using Class I molecules to specifically activate CD8 cells in vitro is now disclosed herein. In addition, therapeutic applications of this new technology in the treatment of cancer, tumors or neoplasias, as well as viral, retroviral, autoimmune, and autoimmune-type diseases are disclosed.

Therefore, the present invention contemplates a eukaryotic cell line containing at least one expressible human Class I MHC nucleotide sequence, preferably a cDNA sequence, under the control of an inducible promoter. More preferably, the cell line also contains an expressible human $\beta 2$ microglobulin nucleotide sequence. In another embodiment, the invention contemplates an insect cell line containing at least one expressible human Class I MHC cDNA sequence. The sequence may be under the control of an inducible promoter, and the cell line may further contain an expressible human $\beta 2$ microglobulin gene.

The present invention also contemplates a eukaryotic cell line expressing a human Class I MHC molecule monotype. In one embodiment, the MHC molecules are empty. In another embodiment, the eukaryotic cell is an insect cell; more preferably, that insect cell is capable of expressing human Class I MHC molecules on its surface. In another aspect, an insect cell of the present invention contains a sufficient number of surface-expressed human Class I MHC molecules to activate CD8 cells. An insect cell as disclosed herein may further contain an average of about 200 surface-expressed human Class I MHC molecules. It is also contemplated that the cells are Drosophila cells having surface-expressed human Class I MHC molecules; more preferably, the cells contain a sufficient number of surface-expressed human Class I MHC molecules to activate CD8 cells. In another embodiment, the cells are Drosophila cells having surface-expressed human Class I MHC molecules; in a further variation, the Drosophila cells contain about 200 to about 500,000 surface-expressed human Class I MHC molecules. In yet another embodiment, the number of the molecules is in the range of 200 to 1,000 per cell. The present invention further contemplates a variety of cell cultures, wherein the cells have the characteristics described herein.

Also contemplated by the present invention are various methods of producing cell lines. In one embodiment, a method of producing a eukaryotic cell line containing at least one expressible human Class I MHC gene is disclosed, which method comprises establishing a culture of eukaryotic cells, and transfecting the culture with an inducible expression vector comprising an inducible promoter and an expressible human Class I MHC gene. In another variation, the vector further comprises an expressible human $\beta 2$ microglobulin gene; in yet another aspect, the vector further comprises a nucleotide sequence encoding a transcribable polyadenylation site. In a preferred embodiment, the vector comprises pRmHa-3. The invention also contemplates that the cells used according to the disclosed methods may be Drosophila cells. In other variations, the culture may be stable, or it may be transient. According to the disclosed methods, the Class I MHC molecules are preferably human and are selected from the group comprising HLA-A, HLA-B, HLA-C, HLA-E, HLA-F, and HLA-G, and more preferably, from the group comprising HLA-A, HLA-B, and HLA-C.

The present invention further contemplates a solid matrix for activating CD8 cells; in a preferred embodiment, the matrix is characterized as being human Class I MHC monotypic. In another variation, the matrix is monoantigenic. Another embodiment discloses a solid matrix for activating CD8 cells in an antigen-specific manner, wherein the matrix is characterized as being human Class I MHC monotypic. In another variation, a solid matrix for activating CD8 cells is contemplated, wherein the matrix contains a CD8 cell-activating amount of human Class I MHC molecule-antigen complexes comprising antigen-loaded human Class I MHC molecules, the complexes being monotypic. In another embodiment, the complexes are mono-antigenic.

The present invention also contemplates methods for producing activated CD8 cells in vitro, wherein one method comprises contacting, in vitro, CD8 cells with antigen-loaded human Class I MHC molecules surface-expressed on Drosophila cells for a time period sufficient to activate, in an antigen-specific manner, the CD8 cells. In one variation, the surface-expressed molecules are monotypic; in another, the surface-expressed molecules are mono-antigenic. The methods contemplated herein may further comprise (1) separating the activated CD8 cells from the antigen-loaded Class I molecules; (2) suspending the activated CD8 cells in an acceptable carrier or excipient; and (3) administering the suspension to an individual in need of treatment. According to the disclosed methods, the antigens may comprise native or undegraded proteins or polypeptides, or they may comprise antigenic polypeptides which have been cleaved into peptide fragments comprising at least 8 amino acid residues prior to incubation with the human Class I molecules.

In another variation, the invention contemplates methods of specifically killing target cells in a human patient, comprising (1) obtaining a fluid sample containing resting or precursor CD8 cells from the patient; (2) contacting, in vitro, the CD8 cells with antigen-loaded human Class I MHC molecules surface-expressed on Drosophila cells for a time period sufficient to activate, in an antigen-specific manner, the CD8 cells; and (3) administering the activated CD8 cells to the patient. The invention also contemplates methods of treating a medical condition, comprising (1) obtaining a fluid sample containing resting or precursor CD8 cells from an individual in need of the medical treatment; (2) contacting, in vitro, the CD8 cells with antigen-loaded human Class I MHC molecules surface-expressed on Drosophila cells for a time period sufficient to activate, in an antigen-specific manner, the CD8 cells; and (3) administering the activated CD8 cells to the patient. In various embodiments the condition may comprise cancer, tumors, neoplasia, viral or retroviral infection, autoimmune or autoimmune-type conditions. In one embodiment, the method of administering the cells comprises intravenous injection.

The invention further contemplates methods of inhibiting rejection of transplanted tissue, comprising (1) conjugating empty human Class I molecules surface-expressed on Drosophila cells to a toxin in vitro; (2) contacting, in vitro, the conjugated Class I molecules with antigenic peptides derived from the transplanted tissue for a time period sufficient to load the conjugates with peptide; (3) isolating the peptide-loaded conjugates; and (4) administering the peptide-loaded conjugates to an individual who has undergone a transplant procedure. In another aspect, the method further comprises monitoring the individual throughout the administration, and continuing the administration until the threat of rejection is substantially reduced or eliminated.

Yet another variation of the present invention contemplates a recombinant nucleotide sequence, preferably a DNA sequence, comprising an expressible human Class I MHC gene operatively linked to an inducible promoter. In one embodiment, the sequence is in a vector. In another variation, the nucleotide sequence further comprises an expressible human β2 microglobulin gene. The vector may further comprise a transcribable polyadenylation site.

The present invention also contemplates stable, empty human Class I MHC molecules produced by the cell lines disclosed herein. In one embodiment, the Class I MHC molecules are human molecules and are selected from the group comprising HLA-A, HLA-B, HLA-C, HLA-E, HLA-F, and HLA-G, and more preferably, from the group comprising HLA-A, HLA-B, and HLA-C. In another variation, the molecules are in soluble form. In yet another embodiment, the Class I MHC molecules may be complexed with an antigenic peptide; preferably, the complex is monoantigenic.

BRIEF DESCRIPTION OF THE DRAWINGS

FIG. 3 (A and B) shows the mean fluorescence of transfected Drosophila cells cultured in serum-free media as determined by cytofluorimetry after staining for $K^b$/mβ2 with Y3 antibody and $D^b$/mβ2 with B22.249 antibody. Prior to the staining and as indicated in the figure, cells were incubated in peptide (25 µg/ml) for one hour at 27° C. followed by a 2-hour incubation at 37° C. The mean fluorescence of each treated cell population is shown plotted against the incubation conditions.

The supernatant from the cocultures were analyzed for IL-2 by $^3$H thymidine incorporation by the IL-2-dependent cell line CTLL (ATCC No. TIB 214). The amount of $^3$H thymidine incorporated is plotted against the initial cell treatments.

Figures 1, 5A:
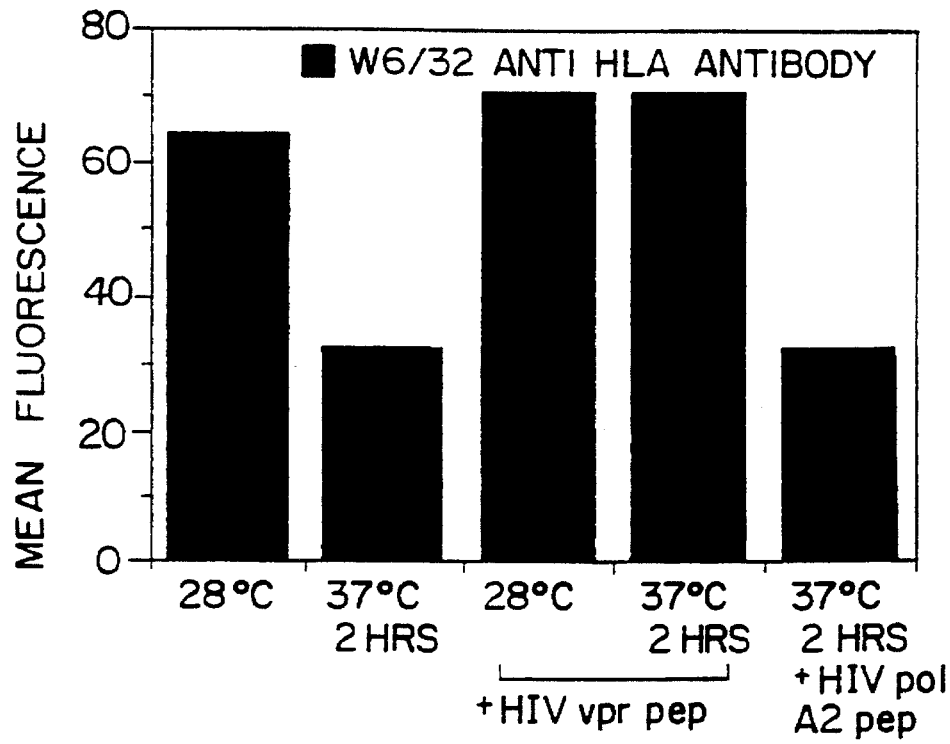
Figures 2, 5A:
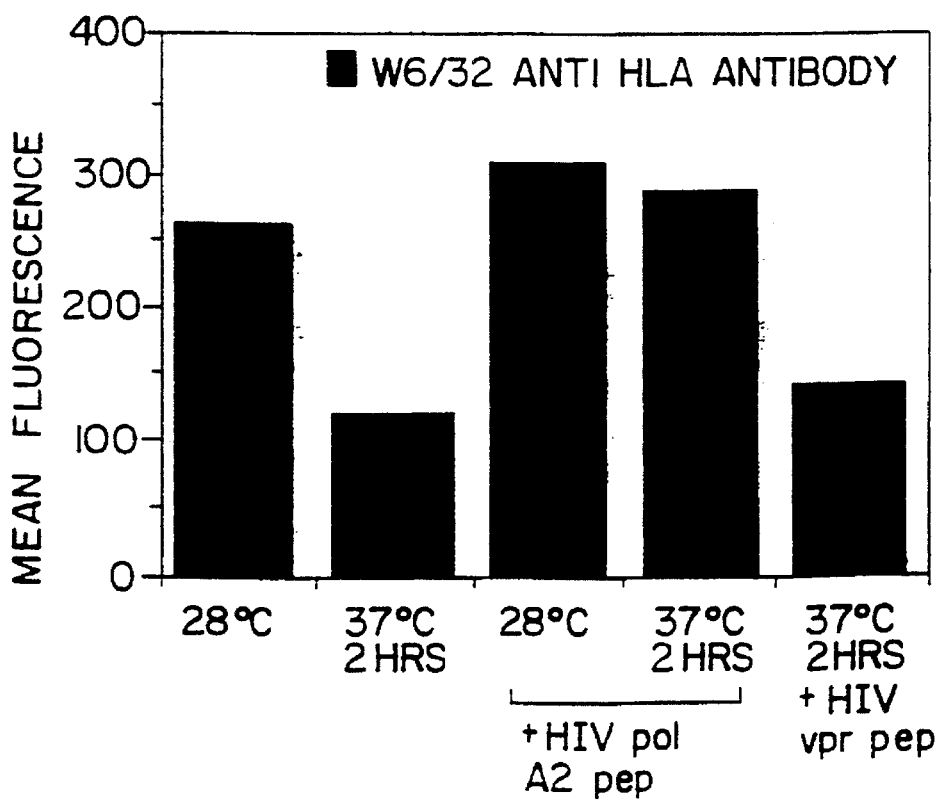
FIG. 2A shows that murine MHC Class I $K^b$/mouse β2 (mβ2) and $D^b$/mβ2 expressed in Drosophila cells have the characteristics of peptide-free or "empty" Class I molecules. Drosophila cells expressing $K^b$/β2, $L^d$/β2, and $D^b$/β2 were labelled for 45 minutes with 35S methionine and lysates prepared. Each lysate was divided into four aliquots, to which was added either OVA, NP peptide, or no peptide at all. After incubation of one hour at 4° C., the other was incubated for one hour at 30° C. Class I molecules were then immunoprecipitated from the lysates and analyzed by SDS-PAGE.

FIGS. 5A-1 and 5A-2 show peptide-induced thermostabilization of HLA B27 and HLA A2.1 respectively expressed on the surface of Drosophila cells by HIV peptides. The mean fluorescence of each cell population is shown plotted against the incubation conditions.

FIG. 5B shows that HLA B7 expressed in Drosophila cells has the characteristics of empty Class I molecules in Triton X100 lysates.

FIG. 5C illustrates that HLA A2.2Y expressed in Drosophila cells has the characteristics of empty Class I molecules in Triton X100 lysates.

FIGS. 6A and 6B illustrate primary CD8 response induction after in vitro CD8 stimulation in the presence or absence of peptide. The responder is B6 mouse spleen cells, and the stimulators are RMA-S (open triangles); RMA-S plus OVA (solid triangles); Drosophila plus OVA (open squares); and Drosophila $K^b$ plus OVA (solid squares). In 6A, the target is RMA-S cells and ovalbumin peptide; in 6B, the target is RMA-S cells. In both diagrams, percent lysis is plotted against effector/target ratio.

FIG. 7 illustrates response induction after in vitro CD8 stimulation with Drosophila cells in the presence or absence of peptide. In 7, responder C57 B1/6 splenocytes are stimulated with Drosophila cell $K^b$ OVA. Target cells include: EL4 (open squares with center dot); EL4 OVA (solid diamond); EL4+OVA peptide (black squares with white dot in center); RMA-S+OVA peptide (black diamonds with white center dot); and RMA-S (solid squares). Percent lysis is plotted against effector/target ratio.

Figure 8A:
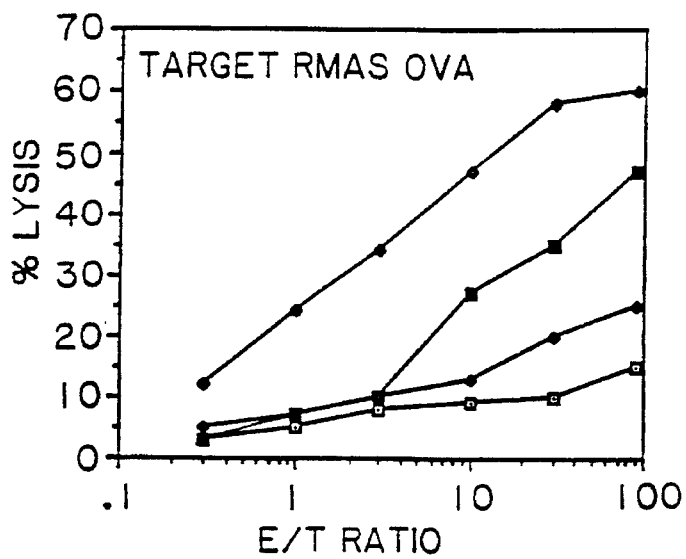
Figure 8B:
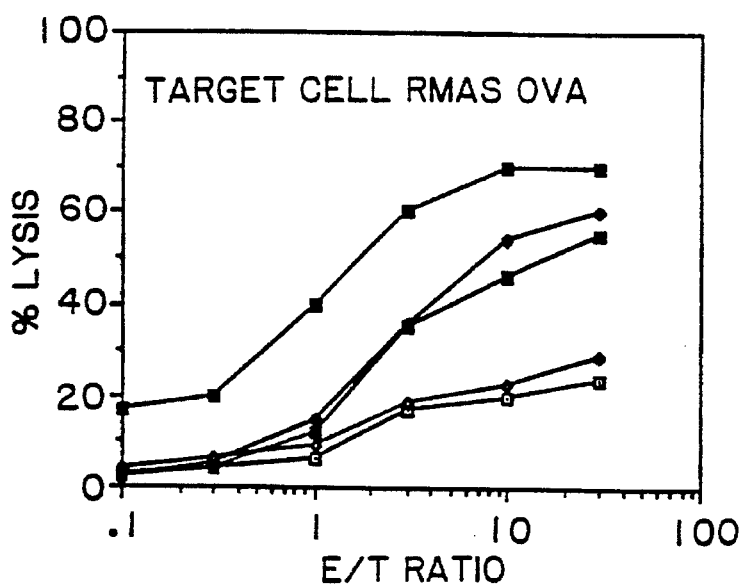

FIG. 8 (A and B) illustrates in vivo priming with transfected Drosophila cells, wherein the responders are C57 B1/6 mouse splenocytes. In 8A, some of the cells are fixed; in 8B, the Drosophila cells are all unfixed. In 8A, stimulator fly cells are as follows: $K^b$ (open squares with center dot); $K^b$ OVA fixed (solid diamonds); $K^b$ OVA fixed+S/N (black square with center white dot); $K^b$ OVA (unfixed) (black diamond with center white dot). In 8B, stimulator fly cells are illustrated as follows: $K^b$ (open squares with center dot); $K^b$/OVA (solid diamonds); $K^b$/OVA in vivo/$K^b$/OVA in vitro (solid squares with white dot in center); $K^b$/OVA in vivo/ $D^b$/OVA in vitro (solid diamonds with white dot in center); and $D^b$/OVA (solid squares). In both A and B, percent lysis is plotted against effector/target ratio.

Figure 9:
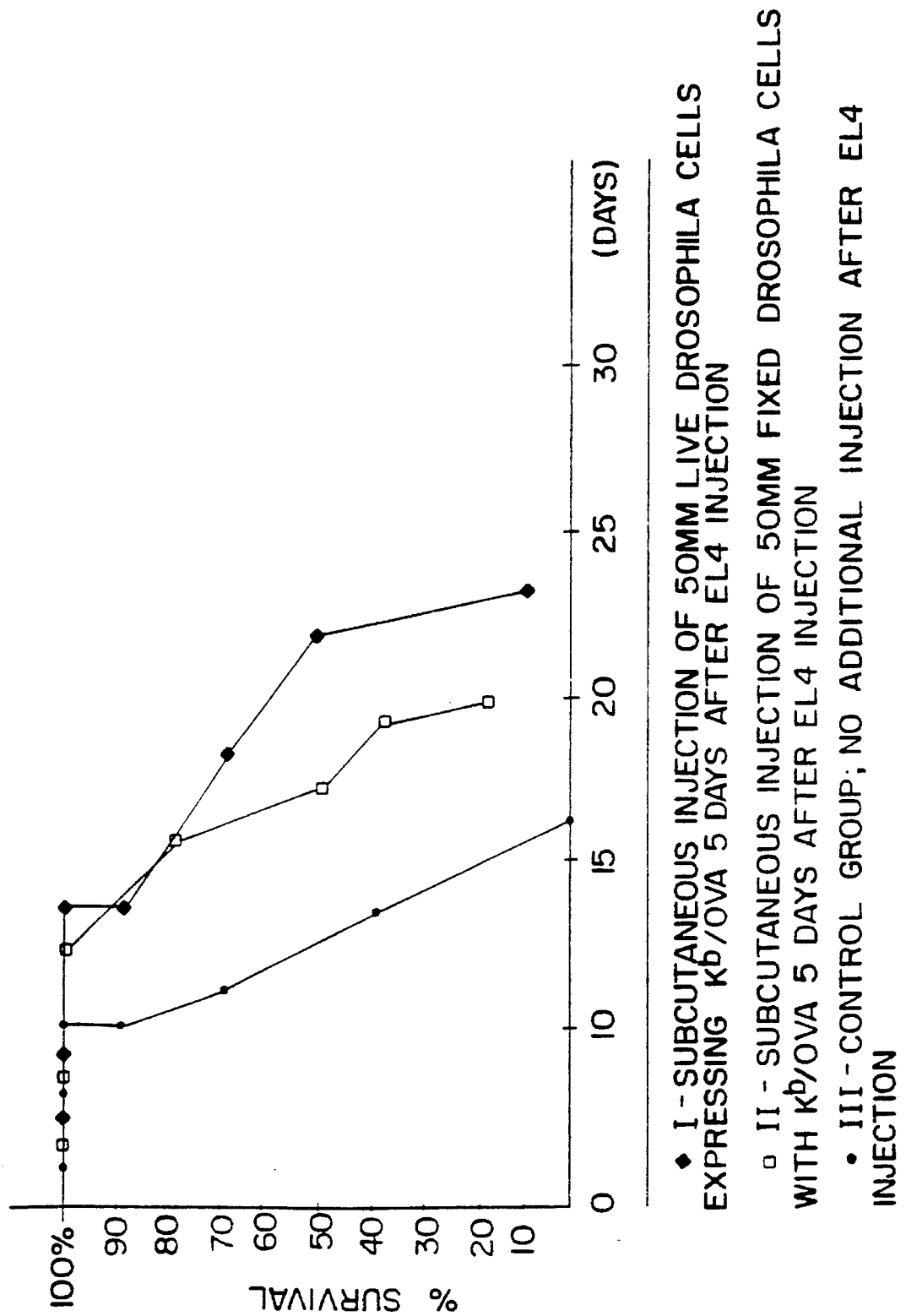

FIG. 9 illustrates the results of an experiment in which C57B1/6 mice were injected with 3 MM EL4 OVA and subsequently with Drosophila cells or no cells. Percent survival of each of the three mouse populations is plotted against the number of days of survival. Group I (solid diamonds) received a subcutaneous injection of 50 MM live Drosophila cells expressing $K^b$/OVA 5 days after EL4 injection; group II (open squares) received 50 MM fixed Drosophila cells expressing $K^b$/OVA 5 days after EL4 injection; and group III (solid circles), the control group, received no additional injections. Group II mice were sacrificed at day 20; group III mice, at day 23.

Figure 10A:
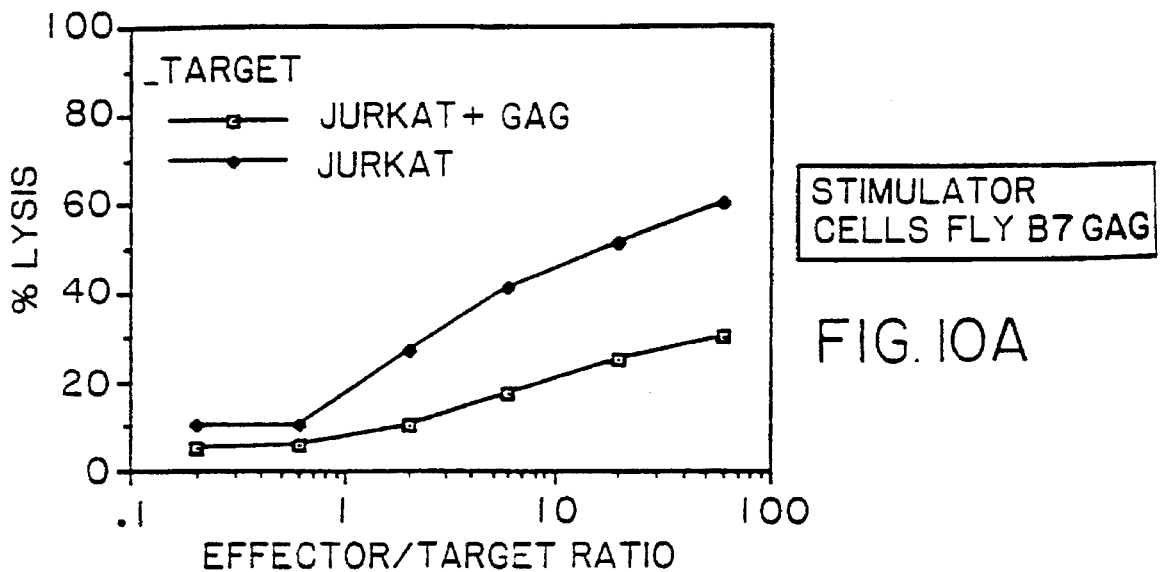
Figure 10B:
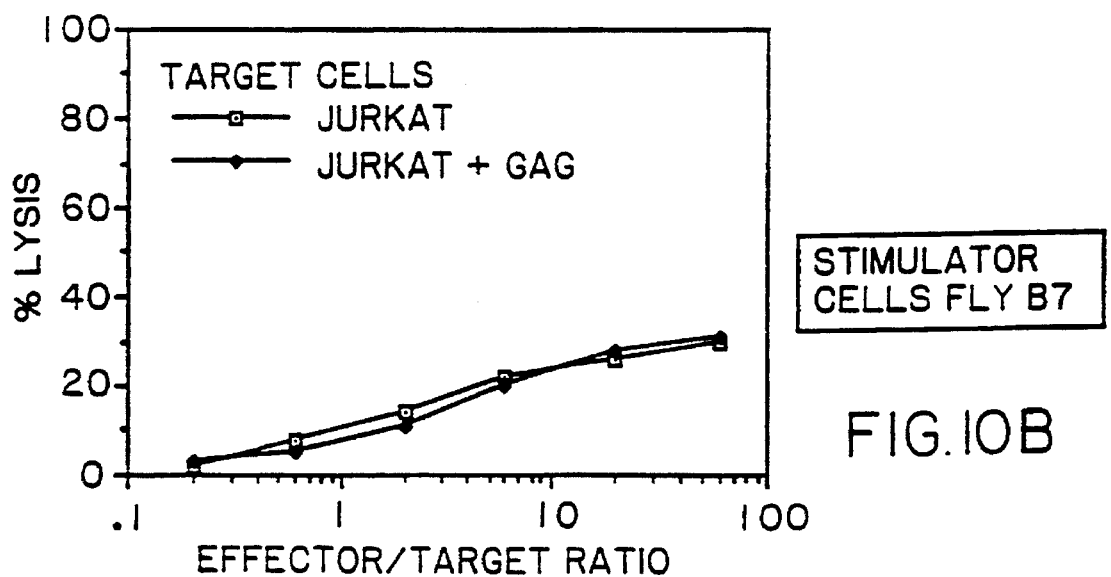

FIGS. 10A, B, and C illustrate in vitro activation with transfected Drosophila cells. In both A and B, the responder cells are transgenic B7/human β2 microglobulin mouse spleen cells. Target cells are Jurkat (open squares with a center dot) and Jurkat coated with HIV GAG peptide A (solid diamonds) as illustrated in both A and B. In 10A, the stimulator cells are Drosophila cells with B7 HIV GAG (A); in 10B, they are Drosophila cells with B7. In 10C, the responder cells are transgenic B7 mouse spleen cells stimulated by Drosophila B7 VPR. Target cells are Jurkat (open squares with center dot); Jurkat/VPR (solid diamonds); RMA-S (solid squares); and RMA-S/VPR (open diamonds with center dot). Percent lysis is plotted against effector/ target ratio in A, B and C.

Figure 11C:
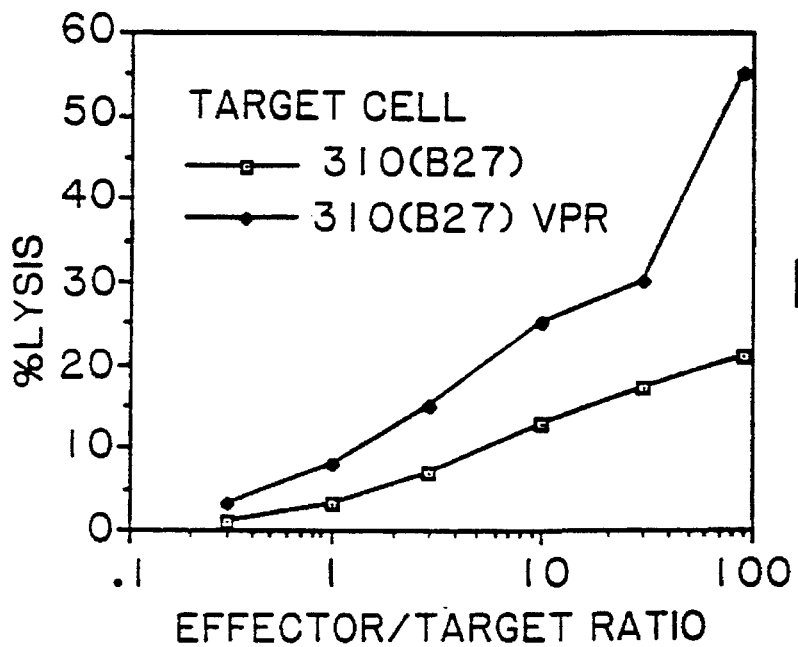

FIGS. 11A, B, and C illustrate in vitro activation with transfected Drosophila cells. In 11A, the responder cells are human PBL HLA B7 stimulated with Drosophila cell B7 VPR. Percent lysis is plotted against effector/target ratio. The target cells are Jurkat VPR (open squares with a center dot); EL4 B7 (solid diamond); Jurkat (solid squares); and EL4 B7 VPR (open diamonds with a center dot). In 11B, the responder cells are human HLA2 PBL stimulated with Drosophila cell A2 GAG (A) (HIV). Percent lysis is plotted against effector/target ratio. The target cells are Jurkat A2 (open squares with a center dot) and Jurkat A2 GAG (A) (solid diamonds). In 11C, the responder cells are human B27 PBL stimulated with Drosophila cell B27 VPR (HIV). The target cells are 310 B27 (open squares with a center dot) or 310 (B27) VPR (solid diamonds). Percent lysis is plotted against effector/target ratio.

Figure 12:
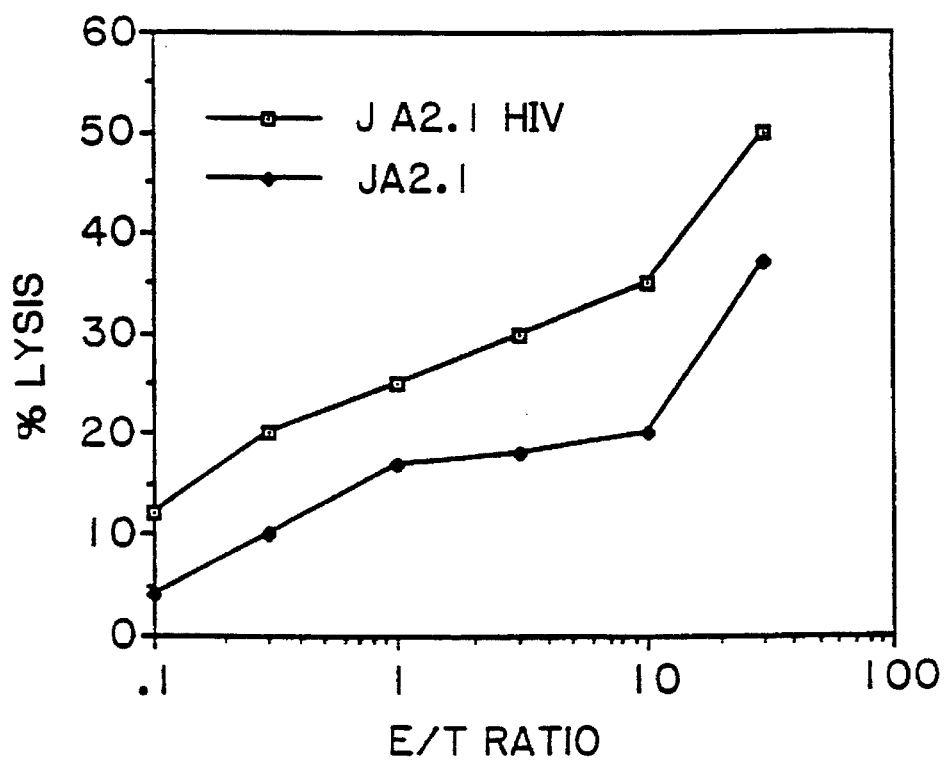

FIG. 12 illustrates in vitro activation with transfected Drosophila cells. The responder cells are human PBL HLA A2.1 stimulated with Drosophila cell A2.1 coated with HIV POL peptide. Percent lysis is plotted against effector/target ratio. The target cells are Jurkat A2.1 HIV (open squares with a center dot) and Jurkat A2.1 (solid diamond).

DETAILED DESCRIPTION OF THE INVENTION

A. Definitions

Amino Acid: All amino acid residues identified herein are in the natural L-configuration. In keeping with standard polypeptide nomenclature, *J. Biol. Chem.*, 243:3557–59, (1969), abbreviations for amino acid residues are as shown in the following Table of Correspondence:

| TABLE OF CORRESPONDENCE | | |
|---|---|---|
| SYMBOL | | |
| 1-Letter | 3-Letter | AMINO ACID |
| Y | Tyr | L-tyrosine |
| G | Gly | glycine |
| F | Phe | L-phenylalanine |
| M | Met | L-methionine |
| A | Ala | L-alanine |
| S | Ser | L-serine |
| I | Ile | L-isoleucine |
| L | Leu | L-leucine |
| T | Thr | L-threonine |
| V | Val | L-valine |
| P | Pro | L-proline |
| K | Lys | L-lysine |
| H | His | L-histidine |
| Q | Gln | L-glutamine |
| E | Glu | L-glutamic acid |
| W | Trp | L-tryptophan |
| R | Arg | L-arginine |
| D | Asp | L-aspartic acid |
| N | Asn | L-asparagine |
| C | Cys | L-cysteine |

It should be noted that all amino acid residue sequences are represented herein by formulae whose left to right orientation is in the conventional direction of amino-terminus to carboxy-terminus.

Base Pair (bp): is a partnership of adenine (A) with thymine (T), or of cytosine (C) with guanine (G) in a DNA double helix.

Clone: describes a large number of identical cells or molecules with a single ancestral cell or molecule.

Complementary Bases: nucleotides that normally pair up when DNA or RNA adopts a double-stranded configuration.

Complementary Nucleotide Sequence: a sequence of nucleotides in a single-stranded molecule of DNA or RNA that is sufficiently complementary to that on another single strand to specifically hybridize to it with consequent hydrogen bonding.

Conserved: a nucleotide sequence is conserved with respect to a preselected (reference) sequence if it non-randomly hybridizes to an exact complement of the preselected sequence.

Downstream: identifies sequences proceeding farther in the direction of expression; for example, the polypeptide coding region for a gene is downstream from the initiation codon.

Expression: the process undergone by a structural gene to produce a polypeptide. It is a combination of transcription and translation.

Gene (Cistron): a nucleic acid whose nucleotide sequence codes for an RNA or a polypeptide. A gene can be either RNA or DNA. It may also include regions preceding and following the coding region (leader and trailer) as well as intervening sequences (introns) between individual coding segments (exons).

Hybridization: the pairing of substantially complementary nucleotide sequences (strands of nucleic acid) to form a duplex or heteroduplex by the establishment of hydrogen bonds between complementary base pairs. It is a specific, i.e., non-random, interaction between two complementary polynucleotides that can be competitively inhibited.

Ligand: Ligand refers to a molecule that contains a structural portion that is bound by specific interaction with a particular receptor protein.

Nucleotide: a monomeric unit of DNA or RNA consisting of a sugar moiety (pentose), a phosphate group, and a nitrogenous heterocyclic base. The base is linked to the sugar moiety via the glycosidic carbon (1' carbon of the pentose) and that combination of base and sugar is a nucleoside. When the nucleoside contains a phosphate group bonded to the 3' or 5' position of the pentose, it is referred to as a nucleotide. A sequence of operatively linked nucleotides is typically referred to herein as a "base sequence" or "nucleotide sequence", and their grammatical equivalents, and is represented herein by a formula whose left to right orientation is in the conventional direction of 5'-terminus to 3'-terminus.

Oligonucleotide or Polynucleotide: a polymer of single or double stranded nucleotides. As used herein, "oligonucleotide" and its grammatical equivalents will include the full range of nucleic acids. An oligonucleotide will typically refer to a nucleic acid molecule comprised of a linear strand of ribonucleotides. The exact size will depend on many factors, which in turn depends on the ultimate conditions of use, as is well known in the art.

Open Reading Frame: a nucleotide sequence, usually a DNA sequence, which is (potentially) translatable into protein.

Polypeptide and Peptide are terms used interchangeably herein to designate a linear series of amino acid residues connected one to the other by peptide bonds between the alpha-amino and carboxy groups of adjacent residues.

Receptor: Receptor and receptor protein are terms used herein to indicate a biologically active proteinaceous molecule that specifically binds to (or with) other molecules.

Recombinant DNA (rDNA) molecule: a DNA molecule produced by operatively linking a nucleic acid sequence, such as a gene, to a DNA molecule sequence of the present invention. Thus, a recombinant DNA molecule is a hybrid DNA molecule comprising at least two nucleotide sequences not normally found together in nature. rDNAs not having a common biological origin, i.e., evolutionarily different, are said to be "heterologous".

Substantially homologous means that a particular subject sequence or molecule, for example, a mutant sequence, varies from a reference sequence by one or more substitutions, deletions, or additions, the net effect of which does not result in an adverse functional dissimilarity between reference and subject sequences. For purposes of the present invention, amino acid sequences having greater than 90 percent similarity, equivalent biological activity, and equivalent expression characteristics are considered substantially homologous. Amino acid sequences having greater than 40 percent similarity are considered substantially similar. For purposes of determining homology or similarity, truncation or internal deletions of the reference sequence should be disregarded, as should subsequent modifications of the molecule, e.g., glycosylation. Sequences having lesser degrees of homology and comparable bioactivity are considered equivalents.

Transfection: is the acquisition of new genetic markers by incorporation of added DNA in eucaryotic cells.

Vector: a nucleic acid, preferably a DNA molecule, capable of autonomous replication in a cell and to which a nucleic acid segment, e.g., a gene or polynucleotide (preferably DNA), can be operatively linked so as to bring about replication of the attached segment. Vectors capable of directing the expression of nucleic acid (preferably DNA) segments (genes) encoding for one or more proteins are referred to herein as "expression vectors". Another variety of important vectors allow cloning of cDNA (complementary DNA) from mRNAs produced using reverse transcriptase.

Cloning Vector: is any plasmid or virus into which a foreign nucleotide sequence (preferably DNA) may be inserted to be cloned.

Expression Vector: is any plasmid or virus into which a foreign nucleotide sequence (preferably DNA) may be inserted or expressed.

B. Detailed Description

1. Human Class I MHC Molecules

A human Class I MHC molecule of the present invention is selected from the group comprising HLA-A, HLA-B, HLA-C, HLA-E, HLA-F, and HLA-G, and more preferably, from the group comprising HLA-A, HLA-B, and HLA-C. The molecules are useful in either soluble or insoluble form. In the soluble ("sol") form, a stop codon is engineered into the nucleotide sequence encoding the HLA molecule of choice preceding the transmembrane domain.

While it is possible to isolate nucleotide sequences encoding human Class I MHC molecules from known, established cell lines carrying the appropriate variants—e.g., transformed cell lines JY, BM92, WIN, MOC, and MG—it is more practical to synthesize the nucleotide sequence from a portion of the gene via polymerase chain reaction (PCR), using the appropriate primers. This method has been successfully used to clone full-length HLA cDNA; for example, the sequences for HLA-A25, HLA-A2, HLA-B7, HLA-B57, HLA-B51, and HLA-B37 are deposited in the GenBank database under accession nos. M32321, M32322, M32317, M32318, M32319 and M32320, respectively. Known, partial and putative HLA amino acid and nucleotide sequences, including the consensus sequence, are published (see, e.g., Zemmour and Parham, Immunogenetics 33:310–320 (1991)), and cell lines expressing HLA variants are known and generally available as well, many from the American Type Culture Collection ("ATCC"). Therefore, using PCR, it is possible to synthesize human Class I MHC-encoding nucleotide sequences which may then be operatively linked to a vector and used to transform an appropriate cell and expressed therein.

Particularly preferred methods for producing the human Class I MHC molecules and human β2 microglobulin molecules of the present invention rely on the use of preselected oligonucleotides as primers in a polymerase chain reaction (PCR) to form PCR reaction products as described herein. MHC and β2 microglobulin gene preparation is typically accomplished by primer extension, preferably by primer extension in a polymerase chain reaction (PCR) format.

If the genes are to be produced by (PCR) amplification, two primers, i.e., a PCR primer pair, must be used for each coding strand of nucleic acid to be amplified. (For the sake of simplicity, synthesis of an exemplary HLA variant sequence will be discussed, but it is expressly to be understood that the PCR amplification method described is equally applicable to the synthesis of β2 microglobulin and all HLA variants, including those whose complete sequences are presently unknown.) The first primer becomes part of the nonsense (minus or complementary) strand and hybridizes to a nucleotide sequence conserved among HLA (plus or coding) strands. To produce coding DNA homologs, first primers are therefore chosen to hybridize to (i.e. be complementary to) conserved regions within the MHC genes, preferably, the consensus sequence or similar, conserved regions within each HLA group—i.e., consensus sequences within HLA-A, HLA-B, HLA-C, and the less-polymorphic groups, HLA-E, -F, and -G. Second primers become part of the coding (plus) strand and hybridize to a nucleotide sequence conserved among minus strands. To produce the HLA-coding DNA homologs, second primers are therefore chosen to hybridize with a conserved nucleotide sequence at the 5' end of the HLA-coding gene such as in that area coding for the leader or first framework region. It should be noted that in the amplification of the coding DNA homologs the conserved 5' nucleotide sequence of the second primer can be complementary to a sequence exogenously added using terminal deoxynucleotidyl transferase as described by Loh et al., *Science* 243: 217–220 (1989). One or both of the first and second primers can contain a nucleotide sequence defining an endonuclease recognition site. The site can be heterologous to the immunoglobulin gene being amplified and typically appears at or near the 5' end of the primer.

The first primer of a PCR primer pair is sometimes referred to herein as the "sense primer" because it hybridizes to the coding or sense strand of a nucleic acid. In addition, the second primer of a PCR primer pair is sometimes referred to herein as the "anti-sense primer" because it hybridizes to a non-coding or anti-sense strand of a nucleic acid, i.e., a strand complementary to a coding strand. A plurality of first primer and/or a plurality of second primers can be used in each amplification, e.g., one species of first primer can be paired with a number of different second primers to form several different primer pairs. Alternatively, an individual pair of first and second primers can be used. In any case, the amplification products of amplifications using the same or different combinations of first and second primers can be combined to increase the diversity of the gene library.

When present, the restriction site-defining portion is typically located in a 5'-terminal non-priming portion of the primer. The restriction site defined by the first primer is typically chosen to be one recognized by a restriction enzyme that does not recognize the restriction site defined by the second primer, the objective being to be able to produce a DNA molecule having cohesive termini that are non-complementary to each other and thus allow directional insertion into a vector.

In one embodiment, the present invention utilizes a set of polynucleotides that form primers having a priming region located at the 3'-terminus of the primer. The priming region is typically the 3'-most (3'-terminal) 15 to 30 nucleotide bases. The 3'-terminal priming portion of each primer is capable of acting as a primer to catalyze nucleic acid synthesis, i.e., initiate a primer extension reaction off its 3' terminus. One or both of the primers can additionally contain a 5'- terminal (5'- most) non-priming portion, i.e., a region that does not participate in hybridization to HLA template.

In PCR, each primer works in combination with a second primer to amplify a target nucleic acid sequence. The choice of PCR primer pairs for use in PCR is governed by considerations as discussed herein for producing human Class I MHC molecules and β2 microglobulin. That is, the primers have a nucleotide sequence that is complementary to a sequence conserved in the gene of choice. Useful priming sequences are disclosed hereinafter.

The strategy used for cloning the HLA genes will depend, as is well known in the art, on the type, complexity, and purity of the nucleic acids making up the various HLA genes. Other factors include whether or not the genes are to be amplified and/or mutagenized.

In general, the HLA genes are comprised of polynucleotide coding strands, such as mRNA and/or the sense strand of genomic DNA. If the HLA is in the form of double stranded genomic DNA, it is usually first denatured, typically by melting, into single strands. An HLA sequence is subjected to a PCR reaction by treating (contacting) the sequence with a PCR primer pair, each member of the pair having a preselected nucleotide sequence. The PCR primer pair is capable of initiating primer extension reactions by hybridizing to nucleotide sequences, preferably at least about 10 nucleotides in length and more preferably at least about 20 nucleotides in length, conserved within the HLA sequence.

The PCR reaction is performed by mixing the PCR primer pair, preferably a predetermined amount thereof, with the nucleic acids of the HLA gene, preferably a predetermined amount thereof, in a PCR buffer to form a PCR reaction admixture. The admixture is maintained under polynucleotide synthesizing conditions for a time period, which is typically predetermined, sufficient for the formation of a PCR reaction product, thereby producing a plurality of different HLA-encoding DNA homologs.

In another strategy, the object is to clone the HLA variant-coding genes from an HLA variant by providing a polynucleotide complement of the HLA, such as the antisense strand of genomic dsDNA or the polynucleotide produced by subjecting mRNA to a reverse transcriptase reaction. Methods for producing such complements are well known in the art.

The PCR reaction is performed using any suitable method. Generally it occurs in a buffered aqueous solution, i.e., a PCR buffer, preferably at a pH of 7–9, most preferably about 8. Preferably, a molar excess (for genomic nucleic acid, usually about $10^6:1$ primer:template) of the primer is admixed to the buffer containing the template strand. A large molar excess is preferred to improve the efficiency of the process.

The PCR buffer also preferably contains the deoxyribonucleotide triphosphates dATP, dCTP, dGTP, and dTTP and a polymerase, typically thermostable, all in adequate amounts for primer extension (polynucleotide synthesis) reaction. The resulting solution (PCR admixture) is heated to about 90° C.–100° C. for about 1 to 10 minutes, preferably from 1 to 4 minutes. After this heating period the solution is allowed to cool to 54° C., which is preferable for primer hybridization. The synthesis reaction may occur at from room temperature up to a temperature above which the polymerase (inducing agent) no longer functions efficiently. Thus, for example, if DNA polymerase is used as inducing agent, the temperature is generally no greater than about 40° C. An exemplary PCR buffer comprises the following: 50 mM KCl; 10 mM Tris-HCl; pH 8.3; 1.5 mM $MgCl_2$; 0.001% (wt/vol) gelatin, 200 μM dATP; 200 μM dTTP; 200 μM dCTP; 200 μM dGTP; and 2.5 units *Thermus aquaticus* DNA polymerase I (U.S. Pat. No. 4,889,818) per 100 microliters of buffer.

The inducing agent may be any compound or system which will function to accomplish the synthesis of primer extension products, including enzymes. Suitable enzymes for this purpose include, for example, *E. coli* DNA polymerase I, Klenow fragment of *E. coli* DNA polymerase I, T4 DNA polymerase, other available DNA polymerases, reverse transcriptase, and other enzymes, including heat-stable enzymes, which will facilitate combination of the nucleotides in the proper manner to form the primer extension products which are complementary to each nucleic acid strand. Generally, the synthesis will be initiated at the 3' end of each primer and proceed in the 5' direction along the template strand, until synthesis terminates, producing molecules of different lengths. There may be inducing agents, however, which initiate synthesis at the 5' end and proceed in the above direction, using the same process as described above.

The inducing agent also may be a compound or system which will function to accomplish the synthesis of RNA primer extension products, including enzymes. In preferred embodiments, the inducing agent may be a DNA-dependent RNA polymerase such as T7 RNA polymerase, T3 RNA polymerase or SP6 RNA polymerase. These polymerases produce a complementary RNA polynucleotide. The high turn over rate of the RNA polymerase amplifies the starting polynucleotide as has been described by Chamberlin et al., *The Enzymes*, ed. P. Boyer, PP. 87–108, Academic Press, New York (1982). Another advantage of T7 RNA polymerase is that mutations can be introduced into the polynucleotide synthesis by replacing a portion of cDNA with one or more mutagenic oligodeoxynucleotides (polynucleotides) and transcribing the partially-mismatched template directly as has been previously described by Joyce et al., *Nuc. Acid Res.* 17:711–722 (1989). Amplification systems based on transcription have been described by Gingeras et al., in *PCR Protocols, A Guide to Methods and Applications*, pp 245–252, Academic Press, Inc., San Diego, Calif. (1990).

If the inducing agent is a DNA-dependent RNA polymerase and therefore incorporates ribonucleotide triphosphates, sufficient amounts of ATP, CTP, GTP and UTP are admixed to the primer extension reaction admixture and the resulting solution is treated as described above.

The newly synthesized strand and its complementary nucleic acid strand form a double-stranded molecule which can be used in the succeeding steps of the process.

After producing HLA variant-encoding DNA homologs for one or a plurality of different genes within the HLA system, the DNA molecules are typically further amplified. While the DNA molecules can be amplified by classic techniques such as incorporation into an autonomously replicating vector, it is preferred to first amplify the molecules by subjecting them to a polymerase chain reaction (PCR) prior to inserting them into a vector. PCR is typically carried out by thermocycling i.e., repeatedly increasing and decreasing the temperature of a PCR reaction admixture within a temperature range whose lower limit is about 10° C. to about 40° C. and whose upper limit is about 90° C. to about 100° C. The increasing and decreasing can be continuous, but is preferably phasic with time periods of relative temperature stability at each of temperatures favoring polynucleotide synthesis, denaturation and hybridization.

PCR amplification methods are described in detail in U.S. Pat. Nos. 4,683,192, 4,683,202, 4,800,159, and 4,965,188, and at least in several texts including "PCR Technology: Principles and Applications for DNA Amplification", H. Erlich, ed., Stockton Press, New York (1989); and "PCR Protocols: A Guide to Methods and Applications", Innis et al., eds., Academic Press, San Diego, Calif. (1990). Various preferred methods and primers used herein are described hereinafter and are also described in Nilsson, et al., *Cell* 58:707 (1989), Ennis, et al., *PNAS USA* 87:2833-7 (1990), and Zemmour, et al., *Immunogenetics* 33:310–20 (1991), for example. In particular, it is preferred to design primers from comparison of 5' and 3' untranslated regions of HLA alleles (e.g., -A, -B, -C, -E, -F, or -G alleles), with selection of conserved sequences. Restriction sites may also be incorporated into the 5' and 3' primers to enable the amplification products to be subcloned into sequencing or expression vectors. It may also be helpful to place a 4-base spacer sequence proximal to the restriction site to improve the efficiency of cutting amplification products with enzymes.

The following primers are preferred for amplification of HLA-A, -B, -C, -E, -F, and -G cDNA, preferably in separate reactions. Resulting cDNAs may then be cloned and sequenced as described herein. These primers are appropriate for use in amplifying all known and presently unknown types of HLA.

HLA A
5' primer: 5' CC ACC ATG GCC GTC ATG GCG CCC 3' (SEQ ID NO 1)
3' primer: 5' GG TCA CAC TTT ACA AGC TCT GAG 3' (SEQ ID NO 2)
HLA B
5' primer: 5' CC ACC ATG CTG GTC ATG GCG CCC 3' (SEQ ID NO 3)
3' primer: 5' GG ACT CGA TGT GAG AGA CAC ATC 3' (SEQ ID NO 4)
HLA C
5' primer: 5' CC ACC ATG CGG GTC ATG GCG CCC 3' (SEQ ID NO 5)
3' primer: 5' GG TCA GGC TTT ACA AGC GAT GAG 3' (SEQ ID NO 6)
HLA E
5' primer: 5' CC ACC ATG CGG GTA GAT GCC CTC C 3' (SEQ ID NO 7)
3' primer: 5' GG TTA CAA GCT GTG AGA CTC AGA 3' (SEQ ID NO 8)
HLA F
5' primer: 5' CC ACC ATG GCG CCC CGA AGC CTC 3' (SEQ ID NO 9)
3' primer: 5' GG TCA CAC TTT ATT AGC TGT GAG A 3' (SEQ ID NO 10)
HLA G
5' primer: 5' CC ACC ATG GCG CCC CGA ACC CTC 3' (SEQ ID NO 11)
3' primer: 5' GG TCA CAA TTT ACA AGC CGA GAG 3' (SEQ ID NO 12)

In preferred embodiments only one pair of first and second primers is used per amplification reaction. The amplification reaction products obtained from a plurality of different amplifications, each using a plurality of different primer pairs, are then combined. However, the present invention also contemplates DNA homolog production via co-amplification (using two pairs of primers), and multiplex amplification (using up to about 8, 9 or 10 primer pairs).

In preferred embodiments, the PCR process is used not only to produce a variety of human Class I-encoding DNA molecules, but also to induce mutations which may emulate those observed in the highly-polymorphic HLA loci, or to create diversity from a single parental clone and thereby provide a Class I MHC molecule-encoding DNA "library" having a greater heterogeneity. First, it should be noted that the PCR process itself is inherently mutagenic due to a variety of factors well known in the art. Second, in addition to the mutation inducing variations described in the above referenced U.S. Pat. No. 4,683,195, other mutation inducing PCR variations can be employed. For example, the PCR reaction admixture can be formed with different amounts of one or more of the nucleotides to be incorporated into the extension product. Under such conditions, the PCR reaction proceeds to produce nucleotide substitutions within the extension product as a result of the scarcity of a particular base. Similarly, approximately equal molar amounts of the nucleotides can be incorporated into the initial PCR reaction admixture in an amount to efficiently perform X number of cycles, and then cycling the admixture through a number of cycles in excess of X, such as, for instance, 2X. Alternatively, mutations can be induced during the PCR reaction by incorporating into the reaction admixture nucleotide derivatives such as inosine, not normally found in the nucleic acids of the HLA variant being amplified. During subsequent in vivo amplification, the nucleotide derivative will be replaced with a substitute nucleotide thereby inducing a point mutation.

A preferred method which may be utilized to clone an expressible nucleotide sequence encoding human Class I MHC is as follows. Cells containing the gene(s) of choice may be grown in an appropriate medium (e.g. RPMI 1640) supplemented as needed (e.g., with fetal calf serum and/or antibiotic). Total cellular RNA is prepared from the culture of choice and first-strand cDNA is then synthesized. cDNA may be synthesized using, for example, oligo(dT) and avian myeloblastosis virus reverse transcriptase. Radiolabeling may also be utilized to assist in isolation and recovery of the cloned product. The product is then preferably extracted, precipitated, and used as the target for PCR amplification using the appropriate PCR primer pair as described herein. Amplification may be carried out using available methods and kits, e.g., GeneAmp kits and a DNA thermal cycler (Perkin-Elmer/Cetus). Various protocols are also useful; one amplification protocol runs for 30 cycles in which each cycle consists of 60 seconds at 94° C., 60 seconds at 65° C., and 90 seconds at 72° C., followed by 10 minutes at 72° C. Another protocol runs for 20 cycles with 60 seconds at 94° C., one second at 65° C., and a variable time at 72° C., which starts at about 50 seconds and increases incrementally by one second in each cycle. Amplification then ends with 10 minutes at 72° C.

Typically, the PCR product is then subcloned and sequenced according to known methods. For example, the product may be extracted and back-extracted (e.g. with phenol/chloroform), precipitated, an digested with an appropriate enzyme—e.g., Hind III—for an appropriate time interval. Double-cut product is isolated and purified (for example, with glass beads) and ligated to similarly-cut vectors. An appropriate vector is then selected based upon the characteristics of the cell line selected to express the MHC molecule. For example, one may express the MHC in *E. coli* for the purpose of recovering the MHC for sequencing analysis. Alternatively, one may express the MHC in a transformed cell line of the present invention for the purpose of activating CD8 cells. The selection of appropriate vectors is thus discussed in greater detail elsewhere in this section.

2. DNA Expression Vectors

A vector of the present invention is a nucleic acid (preferably DNA) molecule capable of autonomous replication in a cell and to which a DNA segment, e.g., gene or polynucleotide, can be operatively linked so as to bring about replication of the attached segment. In the present invention, one of the nucleotide segments to be operatively linked to vector sequences encodes at least a portion of a mammalian Class I MHC molecule. Preferably, the entire peptide-coding sequence of the MHC gene is inserted into the vector and expressed; however, it is also feasible to construct a vector which also includes some non-coding MHC sequences as well. Preferably, non-coding sequences of MHC are excluded. Alternatively, a nucleotide sequence for a soluble ("sol") form of an Class I MHC molecule may be utilized; the "sol" form differs from the non-sol form in that it contains a "stop" codon inserted at the end of the alpha 3 domain or prior to the transmembrane domain. Another preferred vector includes a nucleotide sequence encoding at least a portion of a mammalian β2 microglobulin molecule operatively linked to the vector for expression. It is also feasible to construct a vector including nucleotide sequences encoding both a Class I MHC molecule and a β2 microglobulin.

A preferred vector comprises a cassette that includes one or more translatable DNA sequences operatively linked for expression via a sequence of nucleotides adapted for directional ligation. The cassette preferably includes DNA expression control sequences for expressing the polypeptide or protein that is produced when a translatable DNA sequence is directionally inserted into the cassette via the sequence of nucleotides adapted for directional ligation. The cassette also preferably includes a promoter sequence upstream from the translatable DNA sequence, and a polyadenylation sequence downstream from the mammalian MHC sequence. The cassette may also include a selection marker, albeit it is preferred that such a marker be encoded in a nucleotide sequence operatively linked to another expression vector sequence.

An expression vector is characterized as being capable of expressing, in a compatible host, a structural gene product such as a mammalian Class I MHC polypeptide, a β2 microglobulin, or both. In particular, expression vectors disclosed herein are capable of expressing human Class I MHC molecules and/or human β2 microglobulin.

As used herein, the term "vector" refers to a nucleic acid molecule capable of transporting between different genetic environments another nucleic acid to which it has been operatively linked. Preferred vectors are those capable of autonomous replication and expression of structural gene products present in the nucleotide (DNA) segments to which they are operatively linked.

As used herein with regard to DNA sequences or segments, the phrase "operatively linked" means the sequences or segments have been covalently joined into one piece of DNA, whether in single or double stranded form.

The choice of vector to which a cassette of this invention is operatively linked depends directly, as is well known in the art, on the functional properties desired, e.g., vector replication and protein expression, and the host cell to be transformed, these being limitations inherent in the art of constructing recombinant DNA molecules.

In various embodiments, a vector is utilized for the production of polypeptides useful in the present invention, including MHC variants and antigenic peptides. Such vectors are preferably utilized in conjunction with bacterial "host" cells adapted for the production of useful quantities of proteins or polypeptides. Such vectors may include a prokaryotic replicon i.e., a nucleotide sequence having the ability to direct autonomous replication and maintenance of the recombinant DNA molecule extra-chromosomally in a prokaryotic host cell, such as a bacterial host cell, transformed therewith. Such replicons are well known in the art. In addition, those embodiments that include a prokaryotic replicon may also include a gene whose expression confers a selective advantage, such as drug resistance, to a bacterial host transformed therewith. Typical bacterial drug resistance genes are those that confer resistance to ampicillin or tetracycline. Vectors typically also contain convenient restriction sites for insertion of translatable nucleotide sequences. Exemplary vectors include the plasmids pUC8, pUC9, pUC18, pBR322, and pBR329 available from Bio-Rad Laboratories (Richmond, Calif.), pPL and pKK223 available from Pharmacia (Piscataway, N.J.), and pBS and M13mp19 (Stratagene, La Jolla, Calif.). Other exemplary vectors include pCMU (Nilsson, et al., *Cell* 58:707 (1989)). Other appropriate vectors may also be synthesized, according to known methods; for example, vectors pCMU/K$^b$ and pCMUII used in various applications herein are modifications of pCMUIV (Nilsson, et al., supra).

A sequence of nucleotides adapted for directional ligation, i.e., a polylinker, is a region of the expression vector that (1) operatively links for replication and transport the upstream and downstream nucleotide sequences and (2) provides a site or means for directional ligation of a nucleotide sequence into the vector. Typically, a directional polylinker is a sequence of nucleotides that defines two or more restriction endonuclease recognition sequences, or restriction sites. Upon restriction cleavage, the two sites yield cohesive termini to which a translatable nucleotide sequence can be ligated to the expression vector. Preferably, the two restriction sites provide, upon restriction cleavage, cohesive termini that are non-complementary and thereby permit directional insertion of a translatable nucleotide sequence into the cassette. In one embodiment, the directional ligation means is provided by nucleotides present in the upstream nucleotide sequence, downstream nucleotide sequence, or both. In another embodiment, the sequence of nucleotides adapted for directional ligation comprises a sequence of nucleotides that defines multiple directional cloning means. Where the sequence of nucleotides adapted for directional ligation defines numerous restriction sites, it is referred to as a multiple cloning site.

A translatable nucleotide sequence is a linear series of nucleotides that provide an uninterrupted series of at least 8 codons that encode a polypeptide in one reading frame. Preferably, the nucleotide sequence is a DNA sequence. In addition, there is preferably a sequence upstream of the translatable nucleotide sequence encoding a promoter sequence. Preferably, the promoter is conditional (e.g., inducible). A preferred conditional promoter used herein is a metallothionein promoter or a heat shock promoter.

Vectors may be constructed utilizing any of the well-known vector construction techniques. Those techniques, however, are modified to the extent that the translatable nucleotide sequence to be inserted into the genome of the host cell is flanked "upstream" of the sequence by an appropriate promoter and, in some variations of the present invention, the translatable nucleotide sequence is flanked "downstream" by a polyadenylation site. This is particularly preferred when the "host" cell is an insect cell and the nucleotide sequence is transmitted via transfection. Transfection may be accomplished via numerous methods, including the calcium phosphate method, the DEAE-dextran method, the stable transfer method, electroporation, or via the liposome mediation method. Numerous texts are available which set forth known transfection methods and other procedures for introducing nucleotides into cells; see, e.g., *Current Protocols in Molecular Biology*, John Wiley & Sons, New York (1991).

The vector itself may be of any suitable type, such as a viral vector (RNA or DNA), naked straight-chain or circular DNA, or a vesicle or envelope containing the nucleic acid material and any polypeptides that are to be inserted into the cell. With respect to vesicles, techniques for construction of lipid vesicles, such as liposomes, are well known. Such liposomes may be targeted to particular cells using other conventional techniques, such as providing an antibody or other specific binding molecule on the exterior of the liposome. See, e.g., A. Huang, et al., *J. Biol. Chem.* 255:8015–8018 (1980).

Most useful vectors contain multiple elements including one or more of the following, depending on the nature of the "host" cell—i.e., the cell being transformed: (1) an SV40 origin of replication for amplification to high copy number; (2) an efficient promoter element for high-level transcription initiation; (3) mRNA processing signals such as mRNA cleavage and polyadenylation sequences (and frequently, intervening sequences as well); (4) polylinkers containing multiple restriction endonuclease sites for insertion of "foreign" DNA; (5) selectable markers that can be used to select cells that have stably integrated the plasmid DNA; and (6) plasmid replication control sequences to permit propagation in bacterial cells. In addition to the above, many vectors also contain an inducible expression system that is regulated by an external stimulus. Sequences from a number of promoters that are required for induced transcription have been identified and engineered into expression vectors to obtain inducible expression. Several useful inducible vectors have been based on induction by β-interferon, heat-shock, heavy metal ions, and steroids (e.g. glucocorticoids). (See, e.g., Kaufman, *Meth. Enzymol.* 185:487–511 (1990).)

In a preferred embodiment, the vector also contains a selectable marker. After expression, the product of the translatable nucleotide sequence may then be purified using antibodies against that sequence. One example of a selectable marker is neomycin resistance. A plasmid encoding neomycin resistance, such as phshsneo, phsneo, or pcopneo, may be included in each transfection such that a population of cells that express the gene(s) of choice may be ascertained by growing the transfectants in selection medium.

In a preferred embodiment, the translatable nucleotide sequence may be incorporated into a plasmid with an appropriate controllable transcriptional promoter, translational control sequences, and a polylinker to simplify insertion of the translatable nucleotide sequence in the correct orientation, and may be expressed in a eukaryotic cell, such as Drosophila, or in a prokaryotic cell, such as *E. coli*, using conventional techniques. Preferably, there are 5' control sequences defining a promoter for initiating transcription and a ribosome binding site operatively linked at the 5' terminus of the upstream translatable DNA sequence. To achieve high levels of gene expression in transformed or transfected cells—for example, *E. coli*—it is necessary to use not only strong promoters to generate large quantities of mRNA, but also ribosome binding sites to ensure that the mRNA is efficiently translated. In *E. coli*, for example, the ribosome binding site includes an initiation codon (AUG) and a sequence 3–9 nucleotides long located 3–11 nucleotides upstream from the initiation codon [Shine et al., *Nature*, 254:34 (1975)] The sequence, AGGAGGU, which is called the Shine-Dalgarno (SD) sequence, is complementary to the 3' end of *E. coli* 16S mRNA. Binding of the ribosome to mRNA and the sequence at the 3' end of the mRNA can be affected by several factors, including (1) the degree of complementarity between the SD sequence and 3' end of the 16S tRNA; and (2) the spacing and possibly the DNA sequence lying between the SD sequence and the AUG. (See, e.g., Roberts et al., *PNAS USA* 76: 760 (1979a); Roberts et al., *PNAS USA* 76:5596 (1979b); Guarente et al., *Science* 209:1428 (1980); and Guarente et al., *Cell* 20:543 (1980).) Optimization is generally achieved by measuring the level of expression of genes in plasmids in which this spacing is systematically altered. Comparison of different mRNAs shows that there are statistically preferred sequences from positions −20 to +13 (where the A of the AUG is position 0; see, e.g., Gold et al., *Ann. Rev. Microbiol.* 35:365 (1981)]. Leader sequences have also been shown to influence translation dramatically (Roberts et al., 1979 a, b supra). Binding of the ribosome may also be affected by the nucleotide sequence following the AUG, which affects ribosome binding. (See, e.g., Taniguchi et al., *J. Mol. Biol.* 118:533 (1978).)

One vector which may be used according to the present invention includes a heat shock promoter. Such promoters are known in the art; for example, see Stellar, et al., *EMBO J.* 4:167–171 (1985). If this promoter is used, it is also preferred to add a polyadenylation site.

A preferred vector for use according to the present invention is a plasmid; more preferably, it is a high-copy-number plasmid. It is also desirable that the vector contain an inducible promoter sequence, as inducible promoters tend to limit selection pressure against cells into which such vectors (which are often constructed to carry non-native or chimeric nucleotide sequences) have been introduced. It is also preferable that the vector of choice be best suited for expression in the chosen host. If the host cell population is a Drosophila cell culture, then a compatible vector includes vectors functionally equivalent to those such as p25-lacZ (see Bello and Couble, *Nature* 346:480 (1990)) or pRmHa-1, -2, or -3 (see Bunch, et al., *Nucl. Acids Res.* 16: 1043–1061 (1988)). In the preferred embodiment, the vector is pRmHa-3, which is shown in FIG. 1. This vector includes a metallothionein promoter, which is preferably upstream of the site at which the MHC sequence is inserted, and the polyadenylation site is preferably downstream of said MHC sequence. Drosophila cells are preferred hosts according to the present invention; in particular, Drosophila cells such as Schneider 2 cells have the necessary trans-acting factors required for the activation of the promoter and are thus even more preferred.

Figure 1A:
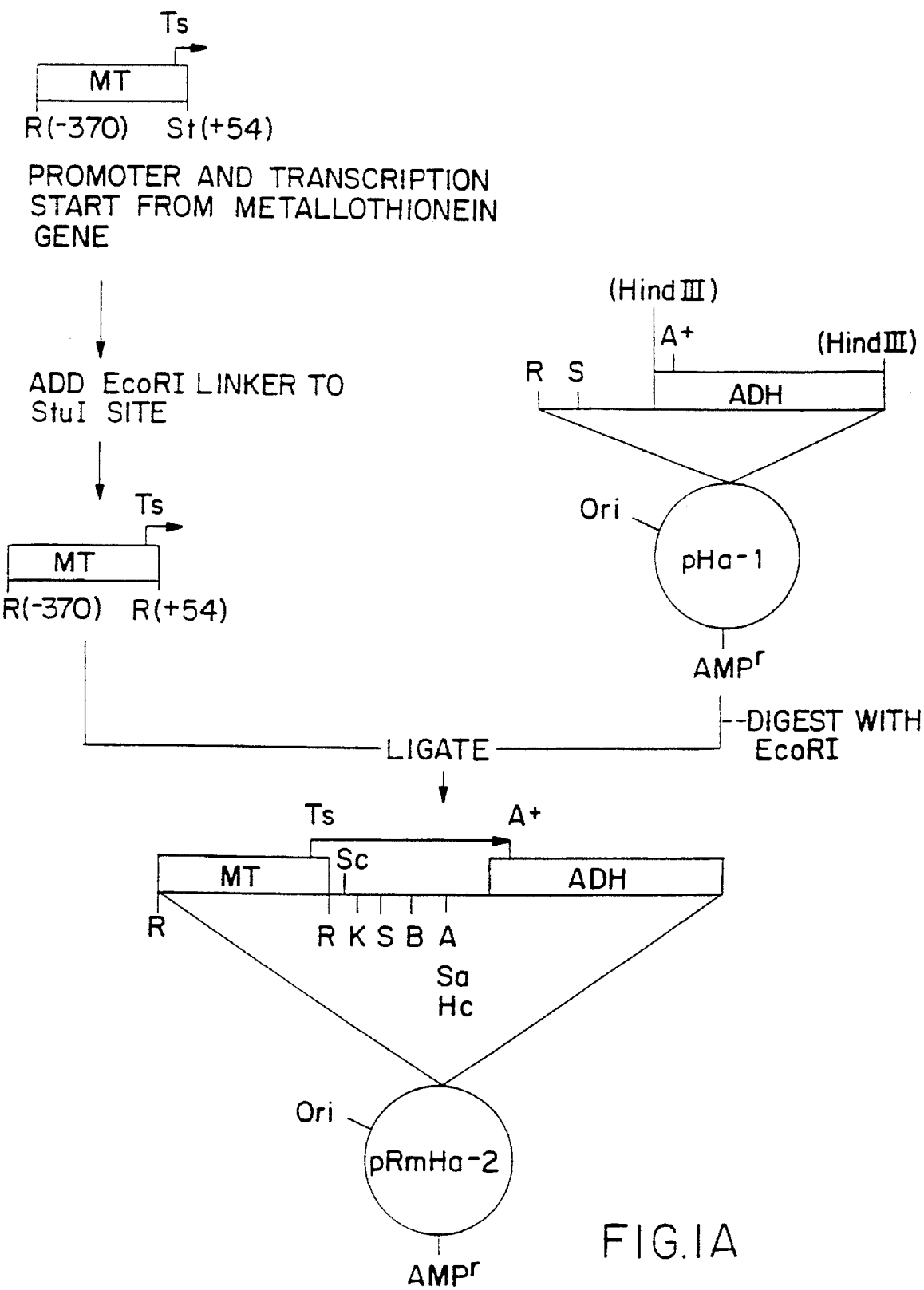
In FIG. 1A, pRmHa-2 construction is shown.

The expression vector pRmHa-3 is based on the bacterial plasmid pRmHa-1, the latter of which is based on plasmid pUC18. The plasmid pUC18 is deposited with the American Type Culture Collection (ATCC, Rockville, Md.), having the accession number 37253. The pRmHa-3 vector contains the promoter, the 5' untranslated leader sequence of the metallothionein gene (sequences 1–421, SEQ ID NO 13) with the R1 and Stu sites removed; see FIG. 1C). It also contains the 3' portion of the Drosophila ADH gene (sequence #6435–7270, SEQ ID NO 14) including the polyadenylation site. Therefore, cloned DNA will be transcriptionally regulated by the metallothionein promoter and polyadenylated. Construction of the pRmHa-1 plasmid is described in Bunch, et al., *Nucl. Acids Res.* 16:1043–1061 (1988). Construction of the pRmHa-3 and pRmHa-2 plasmids (the latter of which has a metallothionein promoter sequence that may be removed as an Eco RI fragment) is illustrated in FIG. 1A, B, and C. With regard to pRmHa-3, a preferred plasmid for use according to the present invention, Pst I, Sph I and Hind III are in the promoter fragment and therefore are not unique. Xba is in the ADH fragment (4 bases from its 3' end) and is also not unique. The following restriction sites are, however, unique in pRmHa-3: Eco RI, Sac I, Kpn I, Sma I, Bam HI, Sal I, Hinc 2, and Acc I.

A cassette in a DNA expression vector of this invention is the region of the vector that forms, upon insertion of a translatable DNA sequence, a sequence of nucleotides capable of expressing, in an appropriate host, a fusion protein of this invention. The expression-competent sequence of nucleotides is referred to as a cistron. Thus, the cassette preferably comprises DNA expression control elements operatively linked to one or more translatable DNA sequences. A cistron is formed when a translatable DNA sequence is directionally inserted (directionally ligated) between the control elements via the sequence of nucleotides adapted for that purpose. The resulting translatable DNA sequence, namely the inserted sequence, is, preferably, operatively linked in the appropriate reading frame.

DNA expression control sequences comprise a set of DNA expression signals for expressing a structural gene product and include both 5' and 3' elements, as is well known, operatively linked to the cistron such that the cistron is able to express a structural gene product. The 5' control sequences define a promoter for initiating transcription and a ribosome binding site operatively linked at the 5' terminus of the upstream translatable DNA sequence.

Thus, a DNA expression vector of this invention provides a system for cloning translatable DNA sequences into the cassette portion of the vector to produce a cistron capable of expressing a fusion protein of this invention.

3. Cell Lines

A preferred cell line of the present invention is capable of continuous growth in culture and capable of expressing mammalian Class I MHC molecules on the surface of its cells. Any of a variety of transformed and non-transformed cells or cell lines are appropriate for this purpose, including bacterial, yeast, insect, and mammalian cell lines. (See, e.g., *Current Protocols in Molecular Biology*, John Wiley & Sons, New York (1991), for summaries and procedures for culturing and using a variety of cell lines, e.g., *E. coli* and *S. cerevisiae*.)

Preferably, the cell line is a eukaryotic cell line. More preferably, the cell line is poikilothermic (i.e., less sensitive to temperature challenge than mammalian cell lines); more preferably, it is an insect cell line. Various insect cell lines are available for use according to the present invention, including moth (ATCC CCL 80), armyworm (ATCC CRL 1711), mosquito larvae (ATCC lines CCL 125, CCL 126, CRL 1660, CRL 1591, CRL 6585, CRL 6586) and silkworm (ATCC CRL 8851). In a preferred embodiment, the cell line is a Drosophila cell line such as a Schneider cell line (see Schneider, *J. Embryol. Exp. Morph.* 27:353–365 (1972)); preferably, the cell line is a Schneider 2 cell line (S2/M3) adapted for growth in M3 medium (see Lindquist, et al., *Drosophila Information Service* 58:163 (1982)).

Schneider cells may be prepared substantially as follows. *Drosophila melanogaster* (Oregon-R) eggs are collected over about a 4 hour interval and are dechorionated in 2.5% aqueous sodium hypochlorite and surface-sterilized by immersion in 70% ethanol for 20 minutes, followed by an additional 20 minutes in 0.05% HgCl$_2$ in 70% ethanol. After being rinsed thoroughly in sterile distilled water, the eggs are transferred to petri dishes containing sterile Metricel black filters backed with Millipore prefilters, both previously wetted with culture medium. The eggs are placed overnight in a 22° C. incubator and removed for culturing when 20–24 hours old. The embryos are each cut into halves or thirds, then placed in 0.2% trypsin (1:250, Difco) in Rinaldini's salt solution (Rinaldini, *Nature (London)* 173:1134–1135 (1954)) for 20–45 minutes at room temperature. From 100–300 embryos are used to initiate each culture.

After the addition of fetal bovine serum (FBS), the fragments are centrifuged at 100 ×g for 2–3 minutes, resuspended in 1.25 ml culture medium and seeded into glass T-9 flasks. The cultures are maintained at about 22°–27° C.±0.5° C., with a gaseous phase of ambient air. Schneider's culture medium (Schneider, *J. Exp. Zool.* 156:91–104 (1964); Schneider, *J. Embryol. Exp. Morph.* 15:271–279 (1966)) containing an additional 500 mg bacteriological peptone per 100 ml medium and supplemented with 15% inactivated FBS is preferably used. The pH (preferably 6.7–6.8) is monitored with 0.01% phenol red. The cell lines are preferably maintained by subculturing every 3–7 days. The cells readily attach to the glass but not so firmly as to require trypsin treatment; typically, simple pipetting is adequate to flush most of the cells from the bottom of the flasks. The morphological appearance of the cells is described in Schneider, *J. Embryol. Exp. Morph.* 27:353–365 (1972). They are essentially epithelial-like in appearance and range from about 5–11 μm in diameter and 11–35 μm in length. Small pockets containing rounded cells may be dispersed randomly throughout the other cells.

Preferably, the Schneider 2 cells are maintained in Schneider's Drosophila medium plus 10% FBS including penicillin (100 unit/ml) and streptomycin (100 mg/ml). It is preferable to keep the cells at a density of more than $0.5 \times 10^5$/ml, and to grow them at a 24°–30° C. temperature range. The cells tend to double in fewer than 24 hours and grow to high cell density, i.e., about $2 \times 10^7$/ml or greater. The cells may also be frozen in 90% FBS and 10% DMSO, for later use or analysis. One may place the cells at –70° C. and then store in liquid nitrogen.

A preferred cell line according to the present invention, identified as Schneider 2 cells, has been deposited pursuant to Budapest Treaty requirements with the American Type Culture Collection (ATCC), Rockville, Md., on Feb. 18, 1992, and was assigned accession number CRL 10974.

In a preferred embodiment, the cell line is a transformed cell line capable of expressing mammalian Class I MHC genes; more preferably, human Class I MHC genes are expressible by the cell line. It is also preferred that the cell line be capable of expressing mammalian $\beta 2$ microglobulin, and more preferably, that the expressed $\beta 2$ microglobulin is human $\beta 2$. An even more preferred cell line is capable of stable or transient expression.

A vector may be utilized to transform/transfect a cell line according to the present invention. Many vectors are available which are useful in the transformation/transfection of cell lines; these vectors are discussed in greater detail above. Briefly, however, in preferred embodiments, cells of the present invention are transfected with cDNAs encoding (human) MHC heavy chains and $\beta 2$ microglobulin, which have each been inserted into (i.e., operatively linked to) an expression vector. In a more preferred embodiment, the vector comprises Drosophila expression plasmid pRmHa-3, into which expressible nucleotide sequences encoding human Class I MHC molecules or human $\beta 2$ microglobulin have been inserted using techniques disclosed herein. Preferably, the cDNAs encoding MHC and those encoding $\beta 2$ microglobulin are operatively linked to separate expression plasmids and are cotransfected into the cultured cells. Alternatively, the cDNAs encoding MHC and $\beta 2$ microglobulin may be operatively linked to the same expression plasmid and cotransfected via that same plasmid. In another variation, cDNAs encoding MHC, $\beta 2$ microglobulin, and a cytokine such as IL2 are operatively linked to expression plasmids and are cotransfected into a cell line of the present invention. Selection of HLA genes, construction of appropriate vectors and primer selection are described in greater detail in sections B.1. and B.2. above.

Successfully transformed cells, i.e., cells that contain an expressible human nucleotide sequence according to the present invention, can be identified via well-known techniques. For example, cells resulting from the introduction of a cDNA or rDNA of the present invention can be cloned to produce monoclonal colonies. Cells from those colonies can be harvested, lysed, and their DNA content examined for the presence of the rDNA using a method such as that described by Southern, *J. Mol. Biol.* 98:503 (1975). In addition to directly assaying for the presence of rDNA, successful transformation or transfection may be confirmed by well-known immunological methods when the rDNA is capable of directing the expression of a subject chimeric polypeptide. For example, cells successfully transformed with an expression vector may produce proteins displaying particular antigenic properties which are easily determined using the appropriate antibodies. In addition, successful transformation/transfection may be ascertained via the use of an additional vector bearing a marker sequence, such as neomycin resistance, as described hereinabove.

It is also preferable that the culture be capable of sustained growth at reduced temperatures. For example, it is preferred that the culture be maintained at about room temperature, e.g., about 24°–27° C. In other embodiments, the culture is maintained at higher temperatures, particularly during the process of activating CD8 cells. It is thus preferred that a culture according to the present invention be capable of withstanding a temperature challenge of about 30° to about 37° C. Addition of $\beta 2$ microglobulin to a culture stabilizes it to at least a 30° C. challenge; addition of $\beta 2$ microglobulin and peptides results in greater thermostability at higher temperatures, i.e., at 37° C.

Therefore, it is even more preferred that a cell line of the present invention be capable of the following: (1) sustained growth at reduced temperatures for a predetermined period of time; (2) transformation by an expression vector; (3) expression of $\beta 2$ microglobulin; (4) expression of one or more types of Class I MHC molecules; (5) loading peptides onto Class I MHC molecules; and (6) expressing empty or peptide-loaded Class I MHC molecules at the cell surface.

In a preferred embodiment of the present invention, a culture of Drosophila cells is established and transfected with vectors operably linked to (1) one or more nucleotide sequences encoding human Class I MHC molecules (2) at least one nucleotide sequence encoding human $\beta 2$ microglobulin. These sequences may be operatively linked to the same vector, but preferably, the sequences for $\beta 2$ microglobulin and for human MHC are in separate vectors. For selection purposes, it is also advantageous to transfect the cell line with a vector operably linked to a selection marker, e.g., neomycin resistance. Subsequently, a population of cells expressing human Class I MHC molecules and $\beta 2$ microglobulin is selected out and maintained in culture.

In order to prepare the culture for expression of empty—or more preferably, peptide-loaded—MHC molecules, the culture may first require stimulation, e.g., via $CuSO_4$ induction, for a predetermined period of time. After a suitable induction period—e.g., about 12–48 hours, peptides may be added at a predetermined concentration (e.g., about 100 μg/ml). Peptides may be prepared as discussed hereinafter in section B.5. After a further incubation period—e.g., for about 12 hours at 27° C.—the culture is ready for use in the activation of CD8 cells. While this additional incubation period may be shortened or perhaps omitted, it is our observation that the culture tends to become increasingly stable to temperature challenge if it is allowed to incubate for a time prior to addition of resting or precursor CD8 cells. For example, cultures according to the present invention to which peptide has been added are capable of expressing significant amounts of peptide-loaded Class I MHC molecules even when incubated for extended periods of time at 37° C.

Nutrient media useful in the culturing of transformed host cells are well known in the art and can be obtained from numerous commercial sources. In embodiments wherein the host cell is mammalian, a "serum-free" medium is preferably used.

4. Human $\beta 2$ Microglobulin

In order to establish a cell line capable of producing therapeutically useful amounts of surface-expressed human Class I MHC molecules, it is preferable to cotransfect a cell line of the present invention with a vector operably linked to a nucleotide sequence encoding $\beta 2$ microglobulin in order to effect appropriate levels of expression of human MHC molecules in the cell line. While the nucleotide sequence encoding mammalian $\beta 2$ microglobulin such as mouse $\beta 2$ microglobulin increases the stability of the human Class I MHC molecules expressed in the cell lines of the present invention, it is preferable to cotransfect the cell line with a vector operably linked to an expressible nucleotide sequence encoding a human β2 microglobulin. As discussed in section B.2. above, a preferred vector according to the present invention includes a nucleotide sequence encoding at least a portion of a mammalian β2 microglobulin molecule operatively linked to the vector for expression. It is also feasible to construct a vector including nucleotide sequences encoding both a Class I MHC molecule and a β2 microglobulin.

A human β2 microglobulin cDNA sequence has been published (see Suggs, et al., PNAS 78:6613–17, 1981) and the sequence was used as a template for a polymerase chain reaction (PCR) using the following primers:

5' primer:
5'         GCTTGGATCCAGATCTACCAT-
GTCTCGCTCCGTGGCCTTAGCTGT-
GCTCGCGCTACTCTC 3' (SEQ ID NO 15)

3' primer
5'         GGATCCGGATGGTTACATGTCGCGATC-
CCACTTAAC 3' (SEQ ID NO 16)

The primers are used in a standard PCR reaction (see section B.1. above and references cited therein). The reaction products are extracted with phenol, purified using a Geneclean kit (Bio 101, San Diego, Calif.), digested with Bam HI and cloned into the Bam HI site of pBS (Stratagene, La Jolla, Calif.). After verification of the sequence, this Bam HI fragment is cloned into the Bam HI site of an appropriate expression vector. In the preferred embodiment, human β2 microglobulin cDNA is synthesized and operably linked to expression vector pRmHa-3.

5. Peptides

Virtually all cellular proteins in addition to viral antigens are capable of being used to generate relevant peptide fragments that serve as potential Class I MHC ligand. In most mammalian cells, then, any particular MHC peptide complex would represent only a small proportion of the total MHC encoded molecules found on the cell surface. Therefore, in order to produce surface-expressed human Class I MHC molecules that have an increased capacity to specifically activate CD8 cells, it is preferable to isolate and load peptide fragments of appropriate size and antigenic characteristics onto Class I molecules.

The peptides of the present invention bind to Class I MHC molecules. The binding occurs under biological conditions which can be created in vivo as well as in vitro. The exact nature of the binding of the peptides need not be known for practice of the invention.

In a preferred embodiment, the peptides to be loaded onto the Class I MHC molecules are antigenic. It is also preferred that the peptides be of a uniform size, preferably 8-mers or 9-mers, and most preferably, 8-mers. It is also preferable that the peptides prepared for loading onto the MHC molecules be of a single species; i.e., that all peptides loaded onto the MHC be identical in size and sequence. In this manner, it is possible to produce monoantigenic peptide-loaded MHC molecules.

Peptides may be presented to the cells via various means. Preferably, peptides are presented in a manner which allows them to enter an intracellular pool of peptides. For example, peptides may be presented via osmotic loading. Typically, peptides are added to the culture medium. The peptides may be added to the culture in the form of an intact polypeptide or protein which is subsequently degraded via cellular processes, e.g., via enzymatic degradation. Alternatively, the intact polypeptide or protein may be degraded via some other means such as chemical digestion (e.g. cyanogen bromide) or proteases (e.g. chymotrypsin) prior to its addition to the cell culture. In other embodiments, the peptides are presented in smaller segments which may or may not comprise epitopic amino acid sequences.

In a preferred embodiment, a sufficient amount of protein(s) or peptide(s) is added to the cell culture to allow the Class I MHC molecules to bind and subsequently present a large density of the peptide—preferably, with the same kind of peptide attached to each MHC—on the surface of human Class I MHC-expressing cells of the present invention. It is also preferred to allow the human Class I MHC and human β2 microglobulin to bind—i.e., to form heterodimers—prior to presenting peptide to the MHC molecules intracellularly.

In another embodiment of the invention, peptides are added to transfected cells of the present invention in order to enhance the thermostability of the MHC molecules expressed by the cells. As noted above, peptides are preferably added to the culture medium. Antigenic peptides that bind to the Class I molecules serve to thermostabilize the MHC molecules and also increase the cell surface expression. Cultures with added peptides which bind to the MHC molecules are thus significantly less susceptible to temperature challenge than cultures without added peptide.

In one embodiment of the present invention, antigenic peptides are presented to the transformed/transfected cell line in various forms. For example, an entire protein or other antigenic polypeptide may be degraded chemically or enzymatically, for example, and added to the cell line in this form. For example, a protein of interest is degraded with chymotrypsin and the resultant mixture of peptide "fragments" is added to a transformed or transfected cell culture; these cells are then allowed to "choose" the appropriate peptides (which are often smaller peptides, preferably 8 mers or 9 mers) to load onto the Class I MHC molecules. Alternatively, an entire protein or polypeptide sequence may be cloned into an appropriate vector and inserted into a procaryotic cell, whereby the cell generates significant amounts of the antigenic polypeptide which are then harvested, purified, and digested into peptides which are then added to the transformed/transfected eukaryotic cell culture; the cells again would be allowed to "choose" the peptides to load onto the expressed MHC.

6. Isolation of Resting or Precursor CD8 cells

Resting (or precursor) CD8 cells—i.e., T cells that have not been activated to target a specific antigen—are preferably extracted from the patient prior to incubation of the CD8 cells with the transformed cultures of the present invention. It is also preferred that precursor CD8 cells be harvested from a patient prior to the initiation of other treatment or therapy which may interfere with the CD8 cells' ability to be specifically activated. For example, if one is intending to treat an individual with a neoplasia or tumor, it is preferable to obtain a sample of cells and culture same prior to the initiation of chemotherapy or radiation treatment.

Methods of extracting and culturing lymphocytes are well known. For example, U.S. Pat. No. 4,690,915 to Rosenberg describes a method of obtaining large numbers of lymphocytes via lymphocytopheresis. Appropriate culturing conditions used are for mammalian cells, which are typically carried out at 37° C.

Various methods are also available for separating out and/or enriching cultures of precursor CD8 cells. Some examples of general methods for cell separation include indirect binding of cells to specifically-coated surfaces. In another example, human peripheral blood lymphocytes (PBL), which include CD8 cells, are isolated by Ficoll- Hypaque gradient centrifugation (Pharmacia, Piscataway, N.J.). PBL lymphoblasts may be used immediately thereafter or may be stored in liquid nitrogen after freezing in FBS containing 10% DMSO (Sigma Chemical Co., St. Louis, Mo.), which conserves cell viability and lymphocyte functions.

Alternative methods of separating out and/or enriching cultures of precursor cells include the following example. After lymphocyte-enriched PBL populations are prepared from whole blood, sub-populations of CD8 lymphocytes are isolated therefrom by affinity-based separation techniques directed at the presence of the CD8 receptor antigen. These affinity-based techniques include flow microfluorimetry, including fluorescence-activated cell sorting (FACS), cell adhesion, and like methods. (See, e.g., Scher and Mage, in *Fundamental Immunology*, W. E. Paul, ed., pp. 767–780, River Press, N.Y. (1984).) Affinity methods may utilize anti-CD8 receptor antibodies as the source of affinity reagent. Alternatively, the natural ligand, or ligand analogs, of CD8 receptor may be used as the affinity reagent. Various anti-T cell and anti-CD8 monoclonal antibodies for use in these methods are generally available from a variety of commercial sources, including the American Type Culture Collection (Rockville, Md.) and Pharmingen (San Diego, Calif.). Depending upon the antigen designation, different antibodies may be appropriate. (For a discussion and review of nomenclature, antigen designation, and assigned antibodies for human leucocytes, including T cells, see Knapp, et al., *Immunology Today* 10:253–258 (1989).) For example, monoclonal antibodies OKT4 (anti-CD4, ATCC No. CRL 8002) OKT 5 (ATCC Nos. CRL 8013 and 8016), OKT 8 (anti-CD8, ATCC No. CRL 8014), and OKT 9 (ATCC No. CRL 8021) are identified in the ATCC Catalogue of Cell Lines and Hybridomas (ATCC, Rockville, Md.) as being reactive with human T lymphocytes, human T cell subsets, and activated T cells, respectively. Various other antibodies are available for identifying and isolating T cell species.

Preferably, the PBLs are then purified. For example, Ficoll gradients may be utilized for this purpose. The purified PBLs would then be mixed with syngeneic Drosophila cells preincubated with the appropriate antigenic peptides.

7. In Vitro Activation of CD8 Cells

In order to optimize the in vitro conditions for the generation of specific cytotoxic T cells, the culture of stimulator cells is maintained in an appropriate medium. In the preferred embodiment, the stimulator cells are Drosophila cells, which are preferably maintained in serum-free medium (e.g. Excell 400), Prior to incubation of the stimulator cells with the cells to be activated, e.g., precursor CD8 cells, an amount of antigenic peptide is added to the stimulator cell culture, of sufficient quantity to become loaded onto the human Class I molecules to be expressed on the surface of the stimulator cells. According to the present invention, a sufficient amount of peptide is an amount that will allow about 200, and preferably 200 or more, human Class I MHC molecules loaded with peptide to be expressed on the surface of each stimulator cell. Preferably, the stimulator cells are incubated with >20 µg/ml peptide.

Resting or precursor CD8 cells are then incubated in culture with the appropriate stimulator cells for a time period sufficient to activate the CD8 cells. Preferably, the CD8 cells shall thus be activated in an antigen-specific manner. The ratio of resting or precursor CD8 (effector) cells to stimulator cells may vary from individual to individual and may further depend upon variables such as the amenability of an individual's lymphocytes to culturing conditions and the nature and severity of the disease condition or other condition for which the within-described treatment modality is used. Preferably, however, the lymphocyte:stimulator cell (e.g. Drosophila cell) ratio is preferably in the range of about 30:1 to 300:1. For example, in one embodiment, $3 \times 10^7$ human PBL and $1 \times 10^6$ live Drosophila cells were admixed and maintained in 20 ml of RPMI 1640 culture medium.

The effector/stimulator culture may be maintained for as long a time as is necessary to stimulate a therapeutically useable or effective number of CD8 cells. In general terms, the optimum time is between about one and five days, with a "plateau"—i.e. a "maximum" specific CD8 activation level—generally being observed after five days of culture. In one embodiment of the present invention, in vitro activation of CD8 cells is detected within a brief period of time after transfection of a cell line. In one embodiment, transient expression in a transfected cell line capable of activating CD8 cells is detectable within 48 hours of transfection. This clearly indicates that either stable or transient cultures of transformed cells expressing human Class I MHC molecules are effective in activating CD8 cells.

8. Separation of CD8 Cells from Drosophila Cells

Activated CD8 cells may be effectively separated from the stimulator (e.g., Drosophila) cells using one of a variety of known methods. For example, monoclonal antibodies specific for the stimulator cells, for the peptides loaded onto the stimulator cells, or for the CD8 cells (or a segment thereof) may be utilized to bind their appropriate complementary ligand. Antibody-tagged molecules may then be extracted from the stimulator-effector cell admixture via appropriate means, e.g., via well-known immunoprecipitation or immunoassay methods.

9. Administration of Activated CD8 Cells

Effective, cytotoxic amounts of the activated CD8 cells can vary between in vitro and in vivo uses, as well as with the amount and type of cells that are the ultimate target of these killer cells. The amount will also vary depending on the condition of the patient and should be determined via consideration of all appropriate factors by the practitioner. Preferably, however, about $1 \times 10^6$ to about $1 \times 10^{12}$, more preferably about $1 \times 10^8$ to about $1 \times 10^{11}$ and even more preferably, about $1 \times 10^9$ to about $1 \times 10^{10}$ activated CD8 cells are utilized for adult humans, compared to about $5 \times 10^6 - 5 \times 10^7$ cells used in mice.

Preferably, as discussed above, the activated CD8 cells are harvested from the Drosophila cell culture prior to administration of the CD8 cells to the individual being treated. It is important to note, however, that unlike other present and proposed treatment modalities, the present method uses a cell culture system (i.e., Drosophila cells) that are not tumorigenic. Therefore, if complete separation of Drosophila cells and activated CD8 cells is not achieved, there is no inherent danger known to be associated with the administration of a small number of Drosophila cells, whereas administration of mammalian tumor-promoting cells may be extremely hazardous.

Methods of re-introducing cellular components are known in the art and include procedures such as those exemplified in U.S. Pat. No. 4,844,893 to Honsik, et al. and U.S. Pat. No. 4,690,915 to Rosenberg. For example, administration of activated CD8 cells via intravenous infusion is appropriate.

10. HLA Typing

As noted previously, HLA haplotypes/allotypes vary from individual to individual and, while it is not essential to the practice of the present invention, it is often helpful to determine the individual's HLA type. The HLA type may be determined via standard typing procedures and the PBLs purified by Ficoll gradients. The purified PBLs would then be mixed with syngeneic Drosophila cells preincubated with the appropriate antigenic peptides—e.g., in therapeutic applications relating to viral infections, cancers, or malignancies, peptides derived from viral- or cancer-specific proteins.

Continuing to use viral or malignant conditions as an example, in those instances in which specific peptides of a particular viral- or cancer-specific antigen have been characterized, the synthesized peptides encoding these epitopes will preferably be used. In cases in which the preferred antigenic peptides have not been precisely determined, protease digests of viral- or cancer-specific proteins may be used. As a source for such antigen, cDNA encoding viral- or cancer-specific proteins is cloned into a bacterial expression plasmid and used to transform bacteria, e.g., via methods disclosed herein.

After HLA typing, if Drosophila cells expressing the preferred HLA are not available, cDNAs encoding the preferred HLA may be cloned via use of the polymerase chain reaction. The primers disclosed in section B.1. above (SEQ ID NO 1 through SEQ ID NO 12) may be used to amplify the appropriate HLA-A, -B,.-C, -E, -F, or -G cDNAs in separate reactions which may then be cloned and sequenced as described in the methods disclosed for HLA A2.1 below. Stable cell lines expressing the cloned HLA may then be established in the Drosophila cells. Alternatively, a population of insect cells transiently expressing a bulk population of cloned recombinant molecules from the PCR reaction may be used for in vitro CD8 activation.

11. Drosophila Mitogen

It has now been found that supernatant from cells cultured according to the present invention augments or restores the ability of cell lines to generate specific, activated CD8 cells. Addition of about 10% Drosophila culture supernatant to a lymphocyte culture, or to fixed cells, efficiently activates CD8. Cultured cells expressing the syngeneic Class I antigens which failed to activate CD8 in primary culture were able to generate specific CD8 after the addition of Drosophila cell culture supernatant.

A factor isolated from the culture which appears to have a significant impact on CD8 activation in Drosophila cell cultures is Drosophila cell mitogen. The mitogen is characterized as a soluble secreted substance with good stability, which maintained its activity even after four months' storage at 4° C. The mitogen has a relatively large molecular weight—i.e., 500 kDa by Superose 6 (Pharmacia, Piscataway, N.J.) gel filtration. It also binds strongly to Mono Q Sepharose (Pharmacia, Piscataway, N.J.). Drosophila cell mitogen apparently induces the proliferation of B cells and activates macrophages.

The mitogen found in Drosophila may be exemplary of other insect mitogens and may provide an effective therapeutic adjuvant. For example, cells from an infected animal may be removed and used to stimulate Drosophila cells subsequently mixed with primary blood lymphocytes and Drosophila mitogen. The mixture may then be used for treatment of the organism.

EXAMPLES

The following examples are intended to illustrate, but not limit, the present invention.

Example 1

Expression of Human Class I MHC Molecules

A. Preparation of pRmHa-3 Expression Vector

The pRmHa-3 expression vector for use in expressing MHC proteins in Drosophila Schneider 2 cells as described in this invention was constructed by ligating a Sph I linearized pRmHa-1 DNA expression vector with a DNA fragment resulting from a Sph I restriction digest of a pRmHa-2 expression vector as described below. The ligating of pRmHa-1 with the pRmHa-2 fragment in this manner was performed to remove one of two Eco RI restriction endonuclease cloning sites present in pRmHa-1. Thus, the resultant pRmHa-3 expression vector contained only one Eco RI restriction site in the multiple cloning site (polylinker) into which various MHC-encoding DNA fragments were inserted as described in the Examples.

1. Preparation of pRmHa-1 Expression Vector

Figure 1B:
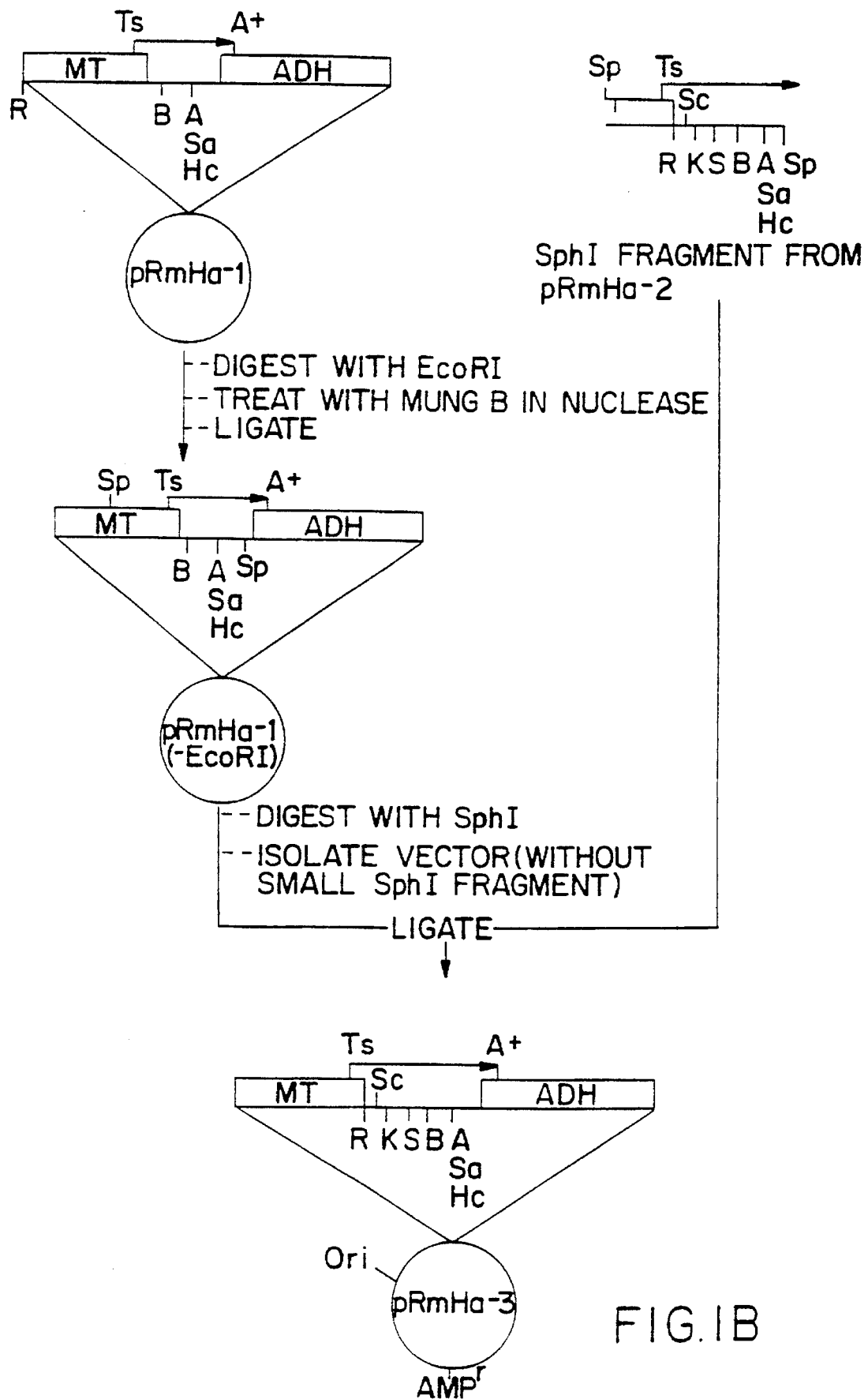
in FIG. 1B, pRmHa-3 construction is shown; and in FIG. 1C, the pRmHa-3 vector is illustrated, showing the restriction, polylinker, promoter, and polyadenylation sites, as well as a site at which a nucleotide sequence may be inserted for expression.

The pRmHa-1 expression vector, containing a metallothionein promoter, metal response consensus sequences (designated MT) and an alcohol dehydrogenase (ADH) gene containing a polyadenylation signal isolated from *Drosophila melanogaster*, was constructed as described by Bunch et al., *Nucl. Acids Res.* 16:1043–61 (1988). A schematic of the final pRmHa-1 construct is shown in FIG. 1B. The plasmid expression vector, pUC18, having the ATCC accession number 37253, was used as the source vector from which subsequent vectors described herein were derived. The pUC18 plasmid contains the following restriction sites from 5' to 3' in the multiple cloning site, all of which are not illustrated in the schematic representations of the pUC18-derived vectors in FIG. 1: Eco RI; Sac I; Kpn I; Sma I and Sma I located at-the same position; Bam HI; Xba I; Sal I, Acc I and Hinc II located at the same position; Pst I; Sph I and Hind III. The pUC18 vector was first digested with Hind III to form a linearized pUC18. Blunt ends were then created by filling in the Hind III ends with DNA polymerase I large fragment as described by Maniatis et al., *Molecular Cloning: A Laboratory Manual*, eds. Cold Spring Harbor Laboratory, New York (1082).

The resultant linearized blunt-ended pUC18 vector was ligated with a 740 base pair (bp) Hinf I fragment from the *Drosophila melanogaster* ADH gene containing a polyadenylation signal. The ligated ADH allele was first isolated from the plasmid pSACI, described by Goldberg et al., *PNAS USA* 77:5794–5798 (1980), by digestion with Hinf I fragment followed by blunt ending with Klenow resulting in the nucleotide sequence listed in SEQ ID NO 14. The pSACI vector containing the ADH allele was constructed by subcloning into pBR322 (ATCC accession number 31344) a 4.7 kilobase (kb) Eco RI fragment of Drosophila DNA selected from a bacteriophage lambda library containing random, high molecular weight (greater than 15 kb). The 5' Hinf I restriction site occurred naturally in the ADH gene at position 1770 as described by Kreitman, *Nature* 304:412–417 (1983). The 3' Hinf I site was derived from the pUC18 vector into which the ADH gene had been cloned. This position was four bases 3' to the Xba I site at position 2500 of the ADH gene. The ADH segment extended from the 35 bp upstream of the polyadenylation/cleavage sequence in the 3' untranslated portion of the ADH mRNA to 700 bp downstream of the polyadenylation signal. The resultant pUC18-derived vector containing the ADH gene fragment was designated pHA-1 as shown in FIG. 1A.

The 421 bp Eco RI/Stu I MT gene fragment was obtained from a clone containing DNA of approximately 15.3 kb in a *Drosophila melanogaster* genomic DNA library. The library, prepared with a Mbo I partial digestion of imaginal DNA, was cloned in the lambda derivative EMBL4. The fragment contained the MT promoter and metal response consensus elements of the Drosophila MT gene (Maroni et al., *Genetics* 112:493–504 (1986)). This region, containing the promoter and transcription start site at nucleotide 1+, corresponded to position −370 to nucleotide position +54 of the MT gene (SEQ ID NO 13). The resultant fragment was then ligated into pHA-1 expression vector prepared above that was previously linearized with Eco RI and Sma I. The 3' blunt end in MT created by the Stu I digest was compatible with the blunt end in pHA-1 created by the Sma I digest. The resultant pUC18-derived vector containing a 5' Drosophila MT gene fragment and a 3' ADH gene fragment was designated pRmHa-1. The pRmHa-1 expression vector, shown in FIG. 1B, contained the origin of replication (ori) and the beta-lactamase gene conferring resistance to ampicillin (Amp$^r$) from pUC18 as shown in FIG. 1A on the pHa-1 vector. The diagram of pRmHa-1 also shows the 5' to 3' contiguous positions of the MT gene fragment, the multiple cloning site and the ADH gene fragment. The pRmHa-1 vector was used as described in c. below in the construction of the pRmHa-3 expression vector.

2. Preparation of pRmHa-2 Expression Vector

The construction of pRmHa-2 is shown in FIG. 1A. For constructing the pRmHa-2 expression vector, the MT fragment prepared above was inserted into the pUC18-derived vector pHA-1 as described for constructing pRmHa-1 above with a few modifications. An Eco RI linker was added to the Stu I site of the Eco RI/Stu I-isolated MT gene fragment prepared above to form a metallothionein fragment having Eco RI restriction sites on both ends. The resultant fragment was then ligated into the ADH fragment-containing pUC18 expression vector that was previously linearized with Eco RI. The resultant pUC18-derived vector containing a 5' Drosophila MT gene fragment and a 3' ADH gene fragment having two Eco RI restriction sites 5' to the multiple cloning site was designated pRmHa-2. The pRmHa-2 expression vector, shown in FIG. 1A, contained the origin of replication (ori) and the beta-lactamase gene conferring resistance to ampicillin (Amp$^r$) from pUC18. The diagram of pRmHa-2 also shows the 5' to 3' contiguous positions of the MT gene fragment, the multiple cloning site and the ADH gene fragment. The pRmHa-2 vector was used along with pRmHa-1 as described in c. below in the construction of the pRmHa-3 expression vector.

3. Preparation of pRmHa-3 Expression Vector

To prepare the pRmHa-3 expression vector that had only one Eco RI restriction site, a fragment from pRmHa-2 was ligated into pRmHa-1. For this construction, pRmHa-2, prepared in b. above, was first digested with Sph I. The resultant Sph I fragment beginning in the middle of the MT gene and extending to the Sph I site in the multiple cloning site was first isolated from the pRmHa-2 vector and then ligated into pRmHa-1 prepared in A.1. above. The pRmHa-1 vector was previously modified to remove the Eco RI restriction site 5' to the MT gene fragment then linearized with Sph I. This process is schematically illustrated in FIG. 1B. To remove the Eco RI site in pRmHa-1, the vector was first digested with Eco RI to form a linearized vector, then blunt ended with Mung Bean nuclease and religated.

Figure 1C:
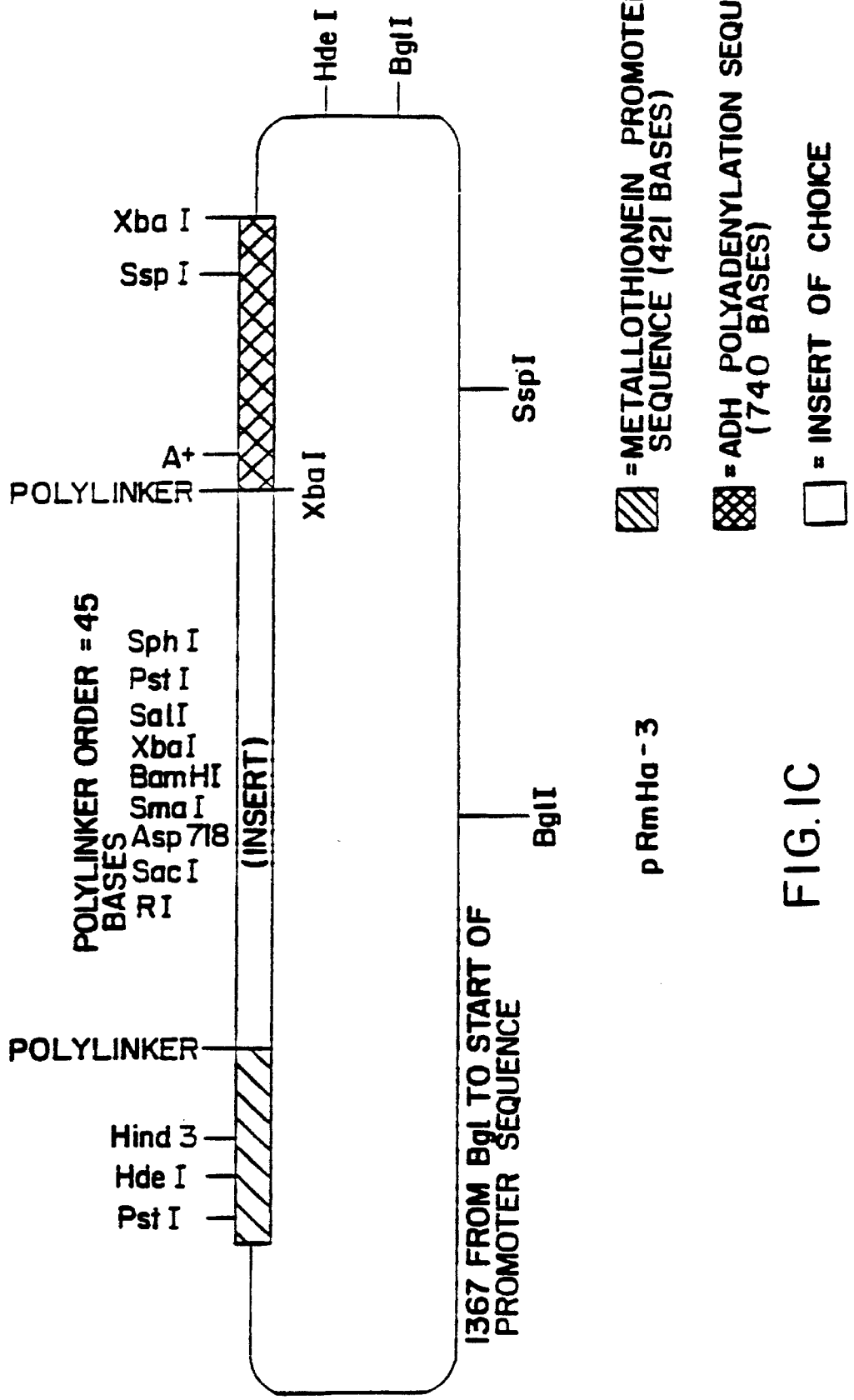
FIG. 1 diagrams the construction of expression plasmids pRmHa-2 and pRmHa-3.

The pRmHa-1 vector lacking an Eco RI site was then digested with Sph I to remove the region corresponding to the Sph I fragment insert from pRmHa-2 and form a linearized pRmHa-1 vector. The Sph I fragment from pRmHa-2 was then ligated into the Sph I linearized pRmHa-1 to form the pRmHa-3 expression vector. A schematic of the pRmHa-3 vector is shown in FIG. 1C. The relative positions of the various restriction sites from the pUC18 vector from which pRmHa-3 was derived are indicated on the figure. In addition, the relative positions and lengths of the MT and ADH gene fragments separated by the multiple cloning site (polylinker) into which the MHC gene of interest is cloned are indicated on the figure. The pRmHa-3 vector, being derived from pUC18, contains the pUC18 origin of replication and beta-lactamase gene conferring ampicillin resistance. Thus, MHC encoding DNA fragments as prepared in this invention and cloned into the multiple cloning site of pRmHa-3 were transcriptionally regulated by the MT promoter and polyadenylated via the ADH gene.

B. cDNA Synthesis

To synthesize HLA A2.2, cDNA encoding a complete A2.2 (see Holmes, et al., *J. Immunol.* 139:936–41 (1987), for the published sequence) is cloned into an M13mp19 plasmid, a commercially available bacteriophage vector (Stratagene, La Jolla, Calif.). cDNA is synthesized by PCR using primers derived from the published sequence of A2. The cDNA is released from an M13mp19 clone as a Not I (overhang filled with Klenow)/EcoRI fragment. (Klenow fragments are part of the *E. coli* DNA polymerase I molecule, produced by the treatment of *E. coli* DNA pol I with subtilisin. They are used to "fill out" 5' or 3' overhangs at the ends of DNA molecules produced by restriction nucleases.) The Not I/Eco RI fragment is inserted into pSP64T digested with Bg III (ends filled with Klenow) and Eco RI. pSP64T is an SP6 cloning vector designed to provide 5' and 3' flanking regions from an mRNA which is efficiently translated (β-globin) to any cDNA which contains its own initiation codon. This translation SP6 vector was constructed by digesting pSP64-Xβm with Bal I and Bst EII, filling in the staggered ends with T4 DNA polymerase and adding a Bgl II linker by ligation. Bal I cuts the β-globin cDNA two bases upstream of the ATG (start codon) and Bst EII cuts eight bases upstream of the TAA (stop codon). There is only one Bgl II site in pSP64T so that restriction enzymes cutting in the polylinker fragment, from Pat I to Eco RI can still be used to linearize the plasmid for transcription. (See Kreig and Melton, *Nucleic Acid Res.* 12:7057–7070, (1984), which also describes the construction of the plasmid pSP64-Xβm.) The resulting plasmid is cleaved with EcoRI (end filled with Klenow) and Hind III which is cloned into the pCMUII polylinker between Hind III (5') and Stu I (3'). (See Paabo, et al., *EMBO J.* 5:1921–1927 (1986).) The entire cDNA is removed as a Hind III (end filled with Klenow) Bam HI fragment which is cloned into pRmHa-3 cleaved with Sma I and Bam HI.

HLA A2.2 sol was prepared by engineering a stop codon into the above-described A2.2 cDNA immediately preceding the transmembrane domain. The mutagenesis is achieved by cleaving the A2.2 cDNA cloned in the eukaryotic expression vector pCMUII between Hind III 5' and Stu I 3' (see above) with Mbo II and Bam HI inserting the following oligonucleotides:

5' primer: 5' GGAGCCGTGACTGACTGAG 3' (SEQ ID NO 17)

3' primer: 5' CCCTCGGCACTGACTGACTCCTAG 3' (SEQ ID NO 18)

The resulting recombinant plasmid is cleaved with Hind III, the overhanging end filled with Klenow, then cut with Bam HI releasing a restriction fragment which is cloned into pRmHa-3 in the same way as A2.2 full length.

HLA A2.1 cDNA is prepared as follows. A truncated HLA A2.1 cDNA sequence is synthesized by PCR using the following primers derived from the published sequence of A2.1 (Koller and Orr, *J. Immunol.* 134:2727–2733 (1985)) and the reaction conditions described by Nilsson, et al., *Cell* 58:707–718 (1989).

5' primer: 5' GCGGATCCATGGCCGTCATGGCGCCC 3' (SEQ ID NO 19)

3' primer: 5' CGGAATTCTCATCAGGGCTTCGGCAGCCC 3' (SEQ ID NO 20)

The resulting PCR fragment is cloned into pBS (Stratagene, La Jolla, Calif.) and the sequence verified by dideoxy sequencing. An 800 bp fragment encoding the majority of the coding sequence of HLA A2.1 is excised from this plasmid with Ava I and Stu I and used to replace the same fragment in the HLA A2.2 transmembrane sequence which had previously been cloned into pRmHa-3 (see above).

HLA B7 is synthesized by PCR using primers derived from the published sequence of B7 (see, e.g., Zemmour and Parham, *Immunogenetics* 33:310–320 (1991)), flanked by Bam HI sites cloned directly into the Bam HI site of pRmHa-3. (See Sood, et al., *Immunogenetics* 22:101–121 (1988).)

HLA B27 cDNA is synthesized by PCR using primers derived from the published sequence of B27 (see, e.g., Zemmour and Parham, *Immunogenetics* 33:310–320 (1991)). Further details are given immediately below.

HLA B27 sol cDNA is prepared as the above B27 cDNA but incorporating the stop codon at the end of the alpha 3 domain of clone pB1 (see Szotz, et al., *PNAS* 83:1428 (1986)). Both truncated and full length B27 cDNAs are obtained in the vector pDS5, with a modified 5' end (see Stueber, et al., *EMBO J.* 3:3143–3148 (1986)). Site-directed mutagenesis is carried out to extend the 5' end of the cDNA. The following sequence (in capital letters) is added to the published B27 cDNA clone; the sequence after the slash mark (/) is the beginning of the published sequence:

GGATCCTCTCAGACGCCGAGATGCGGGTC/acgcgccc . . . (SEQ ID NO 21)

The complete B27 and B27 sol cDNAs are excised from the pDS5 plasmid by first cutting with Apa LI (end filled with Klenow) and Bam HI. The resulting fragments are directionally cloned into pRmHa-3 cleaved with Sal I (filled with Klenow) and Bam HI.

cDNAs encoding any preferred HLA may be cloned via use of the polymerase chain reaction. The primers disclosed in section B.1. above (SEQ ID NO 1 through SEQ ID NO 12) may be used to amplify the appropriate HLA-A, -B, -C, -E, -F, or -G cDNAs in separate reactions which may then be cloned and sequenced as described in the methods disclosed for HLA A2.1 above. Preparation of cDNA from human cells is carried out as described in Ennis, et al., *PNAS USA* 87:2833–2837 (1990). Briefly, a blood sample is obtained from the individual and cells are collected after centrifugation and used to prepare total RNA. First strand cDNA is synthesized by using oligo(dT) and avian myeloblastosis virus reverse transcriptase. The resulting cDNA is used in a PCR amplification reaction utilizing the appropriate primer(s) as noted in section B.1. above, and a GeneAmp kit and thermal cycler (Perkin-Elmer/Cetus). Reaction conditions are preferably as follows. 100 ng cDNA template and 50 picomoles of each oligonucleotide primer are used. Thirty cycles are run as follows: (a) one minute at 94° C.; (b) one minute at 60° C.; and (c) one minute, 30 seconds at 72° C. The PCR reaction is then heated to 100° C. for 10 minutes to kill the Taq polymerase and the ends of the DNA made blunt by T4 polymerase (Stratagene, San Diego, Calif.).

Human β2 microglobulin cDNA is prepared using a published partial cDNA sequence (see Suggs, et al., *PNAS* 78:6613–17, 1981) is used as a template for a polymerase chain reaction (PCR) with the following primers:

5' primer

5' GCTTGGATCCAGATCTACCATGTCTCGCTCCGTGGCCTTAGCTGTGCTCGCGCTACTCTC 3' (SEQ ID NO 15)

3' primer

5' GGATCCGGATGGTTACATGTCGCGATCCCACTTAAC 3' (SEQ ID NO 16)

The primers are used in a standard PCR reaction (see Nilsson, et al., *Cell* 58:707 (1989)). The reaction products are extracted with phenol, purified using a Geneclean kit (Bio 101, San Diego, Calif.), digested with Bam HI and cloned into the Bam HI site of pBS (Stratagene, La Jolla, Calif.). After verification of the sequence, this Bam HI fragment is cloned into the Bam HI site of pRmHa-3.

As noted in the Examples, murine Class I cDNA was utilized in various instances. Murine Class I cDNA was prepared as follows.

H-2$K^b$: cDNA encoding a complete $K^b$ molecule is obtained from an expression plasmid pCMU/$K^b$ constructed as follows. A partial H-2$K^b$ cDNA missing the leader sequence and most of the alpha I domain is prepared according to the method of Reyes, et al., *PNAS* 79:3270–74 (1982), producing pH202. This cDNA is used to generate a full-length molecule. The missing sequence is provided using a genomic clone encoding H-2$K^b$ (Caliban, et al., *Nature* 291:35–39, 1981) as a template in a PCR reaction, using a 5' primer flanked by a Not I site, followed by 21 nucleotides encoding the last seven amino acids of the leader sequence and 18 nucleotides complementary to the beginning of the alpha I domain and a 3' primer complementary to the region encompassing the Sty I site. The resulting fragment is ligated with pH202 at the Sty I site. The 5' sequence encoding the remainder of the signal sequence is obtained form the $D^b$ cDNA (see below) as a Bam HI/Not I fragment. The entire coding sequence is cleaved from the expression plasmid as a Bam HI fragment and cloned into pRmHa-3 cleaved with Bam HI.

H-2$L^d$: cDNA encoding a complete $L^d$ molecule is obtained from an expression plasmid pCMUIV/$L^d$ (see Joly and Oldstone, *Gene* 97:213, 1991). The complete cDNA is cleaved from a eukaryotic expression vector pCMU IV/$L^d$ as a Bam HI fragment and cloned into pRmHa-3 as $K^b$.

H-2$D^b$: cDNA encoding a complete $D^b$ molecule is obtained from expression plasmid pCMUIV/$D^b$ (see Joly and Oldstone, *Science* 253:1283–85, 1991). The complete cDNA is cleaved from a eukaryotic expression vector pCMUIV/$D^b$ as a Bam HI fragment and cloned into pRmHa-3 as $K^b$.

Murine β2 microglobulin: full-length murine β2 microglobulin cDNA is obtained as a Hind III (5') (filled with Klenow)/Bgl II (3') fragment from pSV2neo (ATCC No. 37149) mouse β2 microglobulin cDNA and cloned into pRmHa-3 cleaved with Sma I and Bam HI.

As noted previously, the pCMU vector (pCMUIV) is derived from eukaryotic expression vector pC81G as described in Nilsson, et al., supra. Vector pC81G, in turn, is derived from pA81G (Paabo, et al., *Cell* 33:445–453 (1983)) according to the method disclosed in Paabo, et al., *EMBO J.* 5: 1921–7 (1986). Briefly, these vectors were constructed as follows.

The 220 bp-long leader sequences of vector pA81G are shortened by deleting an 80 bp Hind III to Dde I fragment (nt 1286–1366 of the sequence published by Herisse, et al., *NAR* 8: 2173–2192 (1980)); this construct is called pB81G. A Hinf I fragment of the alpha-globin gene, spanning the region from nt-112 to +19 respective to the site of transcription initiation, was subcloned into the Pst I site of pUC9 and the SV40 72 bp repeat enhancer was inserted upstream of the promoter. This promoter-enhancer element was first tested by cloning it in front of the SV40 T-antigen coding region and the resulting construct was transfected into HeLa cells (ATCC CCL 185). The cells were fixed after two days and stained for T-antigen by indirect immunofluorescence. a large number of stained nuclei was found, indicating strong promoter activity of the alpha-globin fragment. The SV40 promoter in vector pB81G was then replaced by this efficient promoter element leading to construct pC81G.

pCMUIV was constructed by digesting pC81G with Hind III and Bam HI and inserting oligonucleotides encoding the 5' untranslated sequence of *Xenopus laevis* β-globin cDNA, used to generate pSP64T (Krieg, et al., *NAR* 12: 7057–7070 (1984)). However, a Bam HI site was chosen rather than the Bgl II site used in pSP64T. The sequence inserted between Hind III and Bam HI of pC81G was: 5' AGCTTGAGCACT-TGTTCTTTTTGCAGAAGCTCA-GAATAAACGCTCAACTTTG 3' (SEQ ID NO 22).

Vector phshsneo confers neomycin (G418) resistance and is a derivative of phsneo (pUChsneo) with an additional heat-shock promoter (hs) sequence, which may be synthesized from commercially-available pUC8 as described in Steller, et al., *EMBO J.* 4: 167 (1985). The heat shock promoter contained in these vectors is the hsp70 promoter. Other useful vectors conferring neomycin resistance (G418 resistance) include cosmid vector smart2 (ATCC 37588), which is expressed under the control of Drosophila hsp70 promoter, and plasmid vector pcopneo (ATCC 37409).

C. Insertion of Genes into Expression Vectors

The restriction products are subjected to electrophoresis on a 1% agarose gel (Maniatis, et al., *Molecular Cloning: A Laboratory Manual*, Cold Spring Harbor Laboratory (1982)). The restriction fragments encoding the cDNAs are excised from the gel and purified away from the agarose using "Geneclean", according to manufacturers' directions (Bio 101, San Diego, Calif.). The Drosophila expression plasmid pRmHa-3 (see Bunch, et al., *Nucl. Acids Res.* 16: 1043–61, 1988) is cleaved with the appropriate restriction enzymes in One Phor All buffer according to the manufacturer's directions (Pharmacia, Piscataway, N.J.) and treated with alkaline phosphatase as described in the manufacturer's literature (Boehringer Mannheim, Indianapolis, Ind.). One hundred ng of cleaved and phosphatased pRmHa-3 vector is mixed with 300 ng of agarose gel purified Class I MHC heavy chain cDNA or β2 microglobulin cDNA and ligated using T4 DNA ligase and One Phor all buffer as described in the manufacturers' literature. After incubation at 16° C. for five hours, the ligation mixture is used to transform competent *E. coli* JM83 (Maniatis, et al., supra (1982)).

Methods disclosed in Maniatis, et al., supra are used to prepare the cDNA needed; briefly, the methods are as follows. Transformants are selected by plating the *E. coli* on agar plates containing ampicillin. Ampicillin-resistant colonies are individually grown in liquid culture and DNA prepared using the alkaline lysis miniprep method. The presence of the MHC heavy chain cDNA and its orientation in the vector is determined by restriction mapping. Bacteria containing the vector with the cDNA in the correct orientation relative to the metallothionein promoter are used for large scale preparation of DNA using the alkaline lysis method and cesium chloride gradient purification. The amount of DNA obtained is determined spectrophotometrically.

D. Transfection and Labeling of Schneider Cells

Schneider II cells are grown in Schneider medium (Gibco/BRL, Grand Island, N.Y.) supplemented with 10% fetal calf serum (heat treated for one hour at 55° C.), 100 units/ml penicillin, 100 mg/ml streptomycin, and 1 mM glutamine. (For convenience, this supplemented medium is hereinafter referred to as Schneider medium.) Cells are grown at 27° C. and typically passaged every seven days by diluting 1:17 in fresh medium. Cells are converted to growth in serum free media (Excell 400 or 401 supplemented with 100 units/ml penicillin, 100 mg/ml streptomycin, 1 mM glutamine, and 500 µg/ml G418 (JRH Biosciences, Lenexa, Kans.) by initial dilution at 50% Schneider/50% Excell 401. One week later, cells may be passaged into 10% Schneider medium/90% Excell 401 and one week later into 100% Excell 401. Cells are maintained in this medium and passaged every seven days by diluting 2:17 in fresh medium.

$15 \times 10^6$ Schneider cells at a concentration of $10^6$ cells per ml are plated out in 85 mm petri dishes. Twelve hours later, calcium phosphate/DNA precipitates, prepared as described below (1 ml) are added dropwise to the cells. After 48 hours, the supernatant is carefully removed and the cells transferred to a 175 cm$^2$ flask in a total volume of 50 ml in Schneider medium containing 500 µg/ml Geneticin (G418) (Gibco/BRL, Grand Island, N.Y.). After 21 days, 20 ml of the culture is removed to a fresh flask containing 30 ml of Schneider medium containing 500 µg/ml G418. Ten days later, a stable population of cells that weakly adhered to the flask and grew with a doubling time of approximately 24 hours is obtained and these cells are subsequently cultured and passaged in the selection media as described above. Frozen aliquots of these cells are prepared by collecting $5-20 \times 10^6$ cells by centrifugation and resuspending them in 1 ml of cell freezing media (93% fetal calf serum/7% dimethylsulfoxide). Aliquots are then placed at $-70°$ C. for one week and subsequently transferred to liquid nitrogen storage.

Calcium phosphate precipitates are prepared as described by Paabo, et al. (*EMBO J.* 5:1921–27 (1986)), except that 25 µg of DNA is used per transfection. The following combinations of DNA are used to prepare the indicated transfectant:

(a) MHC Class I heavy chain alone: 23 µg heavy chain expression vector DNA+2 µg of phshsneo DNA.

(b) MHC Class I heavy chain +β2 microglobulin: 11.5 µg heavy chain expression vector DNA+11.5 µg of β2 microglobulin (human or mouse) expression vector DNA+2 µg of phshsneo DNA.

Twenty-four hours prior to metabolic labeling, cells are plated out at a cell density of $3-5 \times 10^6$ cells/ml (10 ml/85 mm petri dish) in Schneider medium containing 1 mM CuSO$_4$. Thirty minutes prior to labelling the medium is aspirated from the dishes and the cells are washed with 2×10 ml of PBS and then incubated in Graces insect medium minus methionine and cysteine (special order from Gibco/BRL, Grand Island, N.Y.) for 20 minutes, and then in 1 ml of this medium containing 0.1 mCi 35S Trans label (New England Nuclear; duPont, Boston, Mass.). After the labelling period, the labelling solution is aspirated and the cells are either lysed immediately on ice, with ice cold PBS/1% Triton X100 (1 ml) or after a chase period in the presence of methionine containing Schneider or Excell 400 medium (5 ml) (JRH Biosciences). The chase medium is collected if soluble Class I MHC molecules are being analyzed.

The following operations are all carried out with the lysates kept cold (less than 8° C.). The lysates were collected into Eppendorf tubes, centrifuged in a microfuge tube for 15 minutes at 13,000×g, transferred to a fresh tube containing 100 μl of a 10% slurry of protein A sepharose and placed on an end-over-end rotator for two hours. Following a further centrifugation in the microfuge for 15 minutes, the cell lysates are ready for analysis.

In experiments utilizing murine MHC, Schneider 2 cells were transfected with the murine MHC recombinants described above using the $CaPO_4$ precipitation method; each heavy chain is transfected either alone or as a 50:50 mix with the vector encoding β2 microglobulin. A plasmid encoding neomycin resistance, phshsneo DNA, is included in each transfection such that a population of cells that stably expressed MHC Class I could be obtained by growing the transfectants in selection medium (Geneticin G418-sulphate, Gibco/BRL, Grand Island, N.Y.).

E. Peptide Generation

Antigenic peptides according to the present invention may be obtained from naturally-occurring sources or may be synthesized using known methods. In various examples disclosed herein, peptides are synthesized on an Applied Biosystems synthesizer, ABI 431A (Foster City, Calif.) and subsequently purified by HPLC. Antigenic peptides used in various experiments disclosed herein include those listed below.

---

Ovalbumin (8)[1]   1-letter code: SIINFEKL;
3-letter code: SerIleIleAsnPheGluLysLeu
(SEQ ID NO 23) (residues 5–12)
Ovalbumin (24)[1]   1-letter code: EQLESIINFEKL-TEWTSSNVMEER;
3-letter code: GluGlnLeuGluSerIleIleAsnPheGluLysLeu-ThrGluTrpThrSerSerAsnValMetGluGluArg
(SEQ ID NO 23)
VSV NP[2]   1-letter code: RGYVYQGL
3-letter code: ArgGlyTyrValTyrGlnGlyLeu
(SEQ ID NO 24)
Influenza NP[2]   1-letter code: ASNENMETM
3-letter code: AlaSerAsnGluAsnMetGluThrMet
(SEQ ID NO 25)
LCMV NP[3]   1-letter code: SERPQASGVYMGNL
3-letter code: SerGluArgProGlnAlaSerGlyValTyrMetGlyAsnLeu
(SEQ ID NO 26)
LCMV GP2[4]   1-letter code: DSSGVENPGGYCTK
3-letter code: AspSerSerGlyValGluAsnProGlyGlyTyrCysThrLys
(SEQ ID NO 27)
HIV GAG A (9)[5]   1-letter code: QMKDCTERQ
3-letter code: GlnMetLysAspCysThrGluArgGln
(SEQ ID NO 28)
HIV GAG B (9)[5]   1-letter code: KRWIILGLN
3-letter code: LysArgTrpIleIleLeuGlyLeuAsn
(SEQ ID NO 29)
HIV Vpr (9)[5]   1-letter code: FRIGCRHSR
3-letter code: PheArgIleGlyCysArgHisSerArg
(SEQ ID NO 30)
HIV POL (9)[5]   1-letter code: ILKEPVHGV
3-letter code: IleLeuLysGluProValHisGlyVal
(SEQ ID NO 31)
INF Matrix (10)[6]   1-letter code: ILGFVFTLTV
3-letter code: IleLeuGlyPheValPheThrLeuThrVal
(SEQ ID NO 32)

---

[1]Carbone, et al., J. Exp. Med. 169: 603–12 (1989)
[2]Van Bleek, et al., Nature 348: 213–216 (1990)
[3]Whitton, et al., J. Virol. 63: 4303–10 (1989)
[4]Oldstone, et al., J. Exp. Med. 168: 559–570 (1988).
[5]Nixon and McMichael, AIDS 5: 1049 (1991); see also Nixon, et al., AIDS 4: 841–5 (1990).
[6]Gotch, et al., J. Exp. Med. 168: 2045–57 (1988).

Isolation or synthesis of "random" peptides may also be appropriate, particularly when one is attempting to ascertain a particular epitope in order to load an empty MHC molecule with a peptide most likely to stimulate precursor CD8 cells. One may produce a mixture of "random" peptides via use of proteasomes (see, e.g., Example 2.B.6) or by subjecting a protein or polypeptide to a degradative process—e.g., digestion with chymotrypsin—or peptides may be synthesized. While we have observed that the cell lines of the present invention are able to degrade proteins and polypeptides into smaller peptides capable of being loaded onto human Class I MHC molecules, it is preferable to introduce smaller peptides—e.g., 8 mers and 9-mers—directly into the cell culture to facilitate a more rapid loading and expression process.

If one is synthesizing peptides, e.g., random 8-, 9- and 18-amino acid peptides, all varieties of amino acids are preferably incorporated during each cycle of the synthesis. It should be noted, however, that various parameters—e.g., solvent incompatibility of certain amino acids—may result in a mixture which contains peptides lacking certain amino acids. The process should thus be adjusted as needed—i.e., by altering solvents and reaction conditions—to produce the greatest variety of peptides.

In order to determine "preferences" in peptide selection by MHC molecules, a series of peptides of differing lengths have therefore been synthesized, as shown in Table 3. These include peptides 8 and 9 amino acids in length, as well as longer peptides. In order to quantitate the amount of thermostability imparted by peptides of different length and by different β2 microglobulins, the stability of these various molecules in cell lysates has been examined. Radioactive cell lysates were prepared from Drosophila cells expressing $K^b$/β2, $L^d$/β2 and Db/β2 with either murine or human β2 microglobulin as previously described. The lysates were then aliquoted and additions made as described. For each treatment, five tubes were prepared; these were then incubated at different temperatures between 4° and 47° C. for one hour, after which the Class I was immunoprecipitated and analyzed by SDS-PAGE. The autoradiograms were then scanned using a laser densitometer and the amount of signal plotted against the temperature of the incubation to which that sample had been subjected. The temperature at which 50% of the molecules are Stable was calculated from the graph and was used as a measure of the relative thermostabilities of the different species. As noted hereinabove, murine heavy chains complexed with human β2 microglobulin were stable at temperatures approximately 6–8 degrees higher than if complexed with murine β2. It was also observed that the stabilities imparted by peptide and xenogeneic β2 microglobulin are additive. A large increase in the thermostability of the Class I molecules occurs if 8–9 mers are used, as compared to 12–25 mers; indeed, the difference between the stabilization imparted by the 8–9 mers compared with the larger peptides might be even greater than what was observed previously, for even though the peptides have been purified by HPLC, it is likely that there is some contamination of the larger peptides by 8–9 mers.

It is now shown that the thermostability of a Class I molecule is apparently dependent on: (1) the origin of β2 microglobulin; (2) the presence of peptide; and (3) the length and sequence of this peptide.

F. Generation of Thermostable Surface-Expressed MHC

1. Refining the Parameters using Murine MHC

Prior to experimentation with human Class I MHC molecule-expressing cells, optimization of various parameters using murine MHC was performed. First, it was verified that murine MHC Class I molecules expressed in Drosophila cells have the characteristics of peptide-free or "empty" Class I molecules.

Figure 2B:
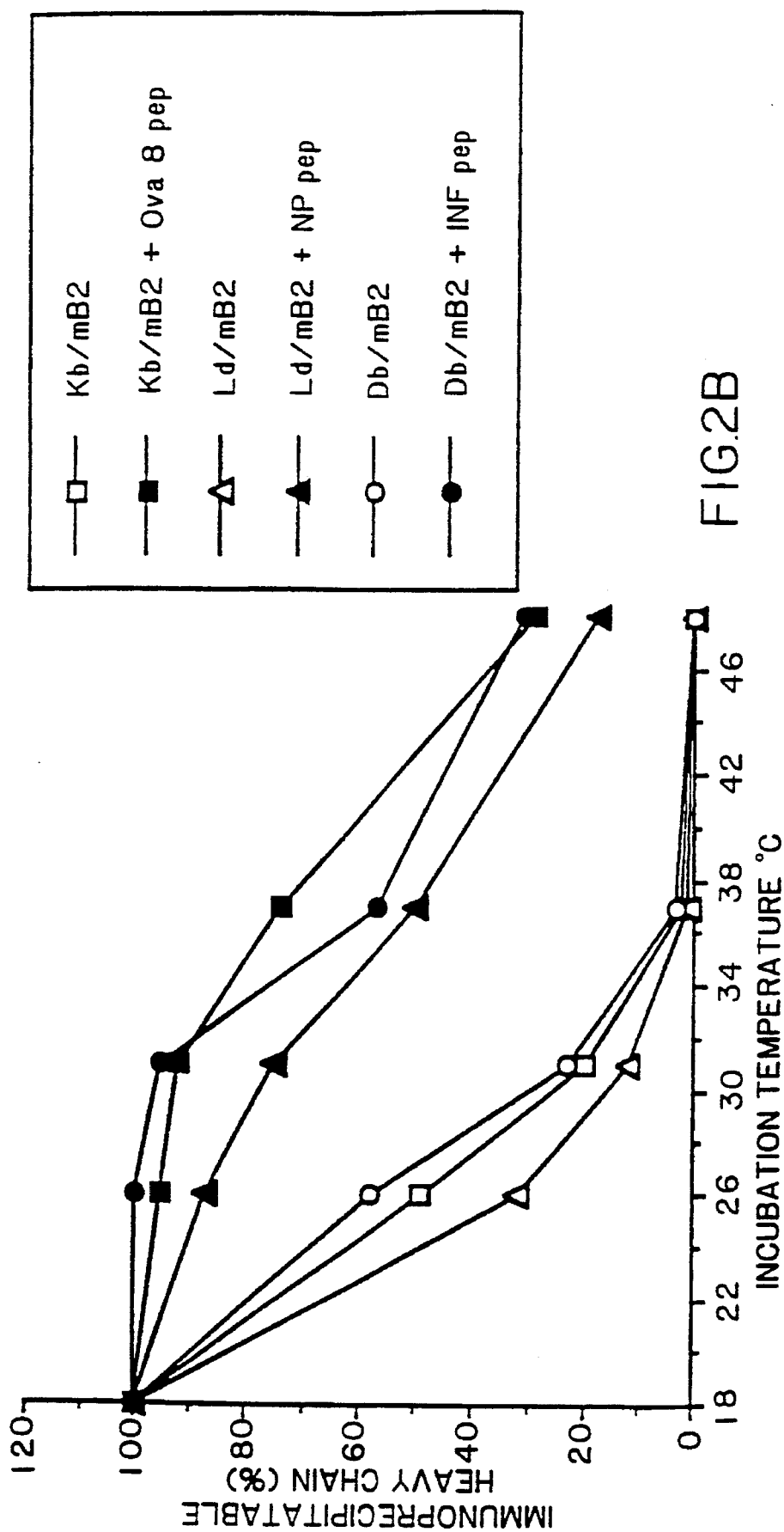
FIG. 2B illustrates results of an assay of radioactive cell lysates prepared from Drosophila cells expressing $K^b$/β2, $L^d$/β2 and $D^b$/β2 with either murine or human β2 microglobulin. Incubation temperature (in °C.) is plotted against immunoprecipitable heavy chain (in %). $K^b$/mβ2 (open squares), $K^b$/mβ2+OVA-8 (solid squares), $L^d$/mβ2 (open triangles), $L_d$/mβ2+NP (solid triangles), $D^b$/mβ2 (open circles), and $D^b$/mβ2+INF (solid circles) are shown.

For example, FIGS. 2A and B illustrate results of assays prepared from Drosophila cells expressing $K^b$/β2, $L^d$/β2 and Db/β2 with either murine or human β2 microglobulin.

Drosophila cells expressing $K^b/\beta 2$, $L^d/\beta 2$, and Db/β2 were labelled for 45 minutes with 35S methionine and lysates prepared as described above. Each lysate was divided into four aliquots, to which was added either OVA, NP or GP2 peptide, or no peptide at all. After incubation of one hour at 4° C., the other was incubated for one hour at 30° C. Class I molecules were then immunoprecipitated from the lysates and analyzed by SDS-PAGE. Dramatic stabilization of $K^b/\beta 2$ to the temperature challenge occurred when either OVA or NP peptide were added to the lysates; similarly, $L^d/\beta 2$ was stabilized by the addition of the NP peptide. $D^b/\beta 2$ does not seem to be as temperature labile as the other two molecules; nevertheless, an increase in stability of the molecule is seen upon addition of the GP2 peptide to the lysate, whereas addition of OVA or NP peptide does not achieve this. Two bands can be seen immunoprecipitated for each Class I, representing the Golgi processed (lower) or unprocessed forms, both molecules appear to be equally well stabilized by the addition of peptide to the lysate. The small amount of "30° C. resistant" protein observed in the $K^b/\beta 2$ untreated or GP2 lysates is background, as addition of Y3 to a lysate of labelled $L^d/\beta 2$ cells resulted in the isolation of this band (not shown).

Figure 3A:
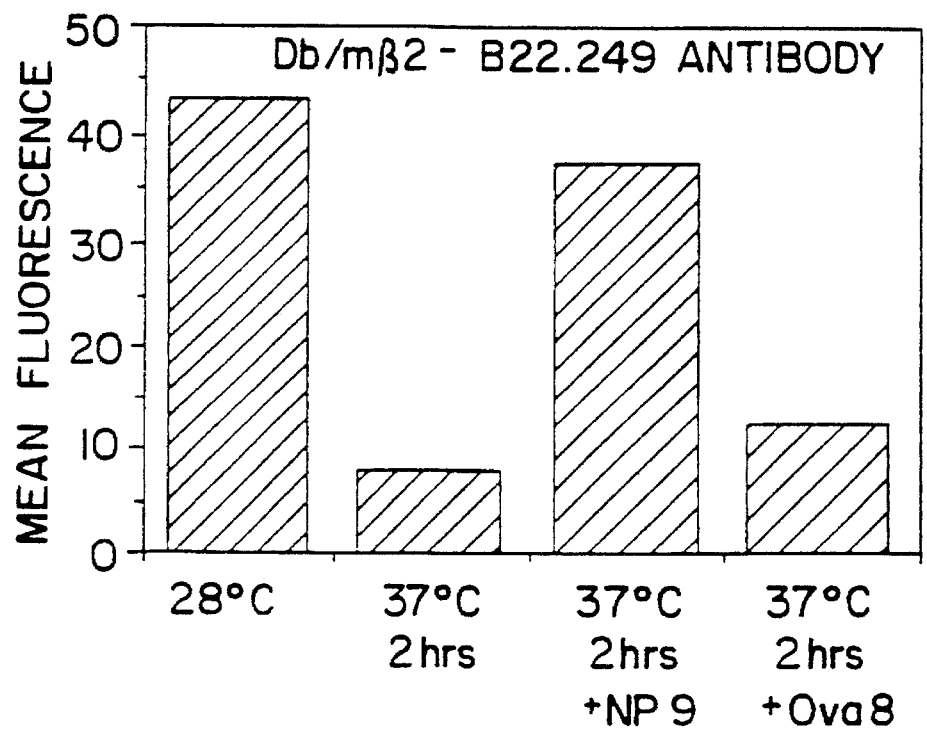
FIG. 3A shows that mouse Class I molecules expressed on the surface of Drosophila cells are rapidly denatured at 37° C. such that they can no longer be recognized by anti-Class I antibodies.
Figure 3B:
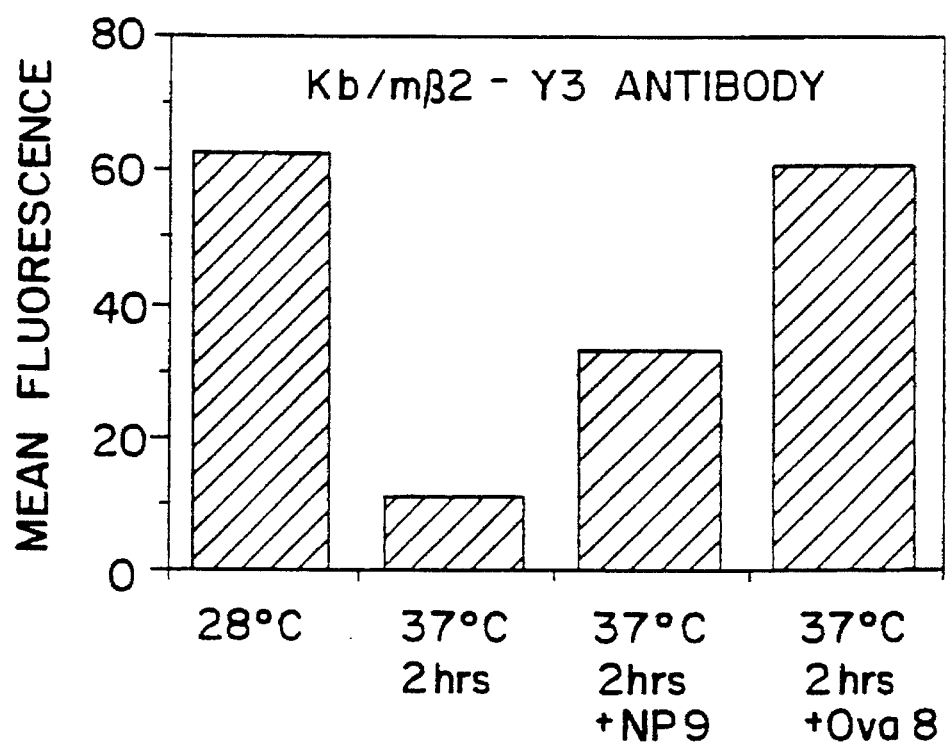
FIG. 3B shows that Class I MHC molecules expressed in Drosophila cells are thermolabile in Triton X100 lysates unless they are preincubated in the presence of peptide known to specifically bind to the Class I.

Next, the possibility that human β2 microglobulin was better than murine β2 microglobulin at thermostabilizing murine heavy chains was investigated. It was found that addition of human β2 to Drosophila cells grown in Excell 400 medium not only increased the steady-state level of all three murine Class I molecules, it also rendered the molecules stable at 37° C. for at least three hours. The increased stability of the murine Class I upon addition of human β2 could have been the result of increasing the β2 concentration in the medium; this possibility was ruled out. cDNA encoding human β2 microglobulin was cloned into Drosophila expression vector pRmHa-3 and cotransfected with expression plasmids containing the various murine Class I heavy chain cDNAs and the resistance marker plasmid as described previously. After G418 selection, the cells were stained with the appropriate anti-Class I antibodies for surface expression, strongly expressing cells were selected using the FACS. Stable populations of cells were obtained (data not shown). Cells were then conditioned to growth in Excell 400 and incubated for different lengths of time at 37° C. The mouse Class I molecules synthesized with human β2 microglobulin were stable to a 3-hour incubation at 37° C. without addition of exogenous β2 to the Excell medium (data not shown). Our results indicate that the thermostability of murine Class I molecules is dependent on the presence of peptide and on the origin of the β2 microglobulin. (See FIGS. 3A and 3B.)

In addition, it has now been determined that the Class I molecules expressed on the cell surface are further stabilized by the addition of peptides of appropriate size. (See FIGS. 5A–C.) A series of peptides of differing lengths were synthesized, as shown in Table 3 (see Example 5.2.). These include a peptide that is 8 amino acids in length; RGYVYQGL (SEQ ID NO 24) has been characterized as the epitope in the vesicular stomatitis virus (VSV) G protein. Similarly, OVA 8 mer peptide SIINFEKL (SEQ ID NO 23, residues 5–12) has been identified as the peptide in ovalbumin that is presented by $K^b/\beta 2$, and the 9-amino-acid-long peptide ASNENMETM (SEQ ID NO 25) has been characterized as the epitope of the influenza virus nuclear protein presented by $D^b/\beta 2$. Addition of these "parent" peptides to Drosophila cells cultured in Excell and expressing murine Class I resulted in 37° C. thermostability of $K^b/\beta 2$ by the OVA peptide and $D^b/\beta 2$ by the NP peptide.

In order to quantitate the amount of thermostability imparted by peptides of different length and by different β2 microglobulins, the stability of these various molecules in cell lysates has been examined. Radioactive cell lysates were prepared from Drosophila cells expressing $K^b/\beta 2$, $L^d/\beta 2$ and $D^b/\beta 2$ with either murine or human β2 microglobulin as previously described. The lysates were then aliquoted and additions made as described in Example 1.D. For each treatment, five tubes were prepared; these were then incubated at different temperatures between 4° and 47° C. for one hour, after which the Class I was immunoprecipitated and analyzed by SDS-PAGE. The autoradiograms were then scanned using a laser densitometer and the amount of signal plotted against the temperature of the incubation to which that sample had been subjected. The temperature at which 50% of the molecules are stable was calculated from the graph and was used as a measure of the relative thermostabilities of the different species. As previously observed, murine heavy chains complexed with human β2 microglobulin were stable at temperatures approximately 6–8 degrees higher if complexed with murine β2. Interestingly, the stabilities imparted by peptide and xenogeneic β2 microglobulin are additive. A large increase in the thermostability of the Class I molecules occurs if 8–9 mers are used, as compared to 12–25 mers; indeed, the difference between the stabilization imparted by the 8–9 mers compared with the larger peptides might be even greater than what was observed previously, for even though the peptides have been purified by HPLC, it is likely that there is some contamination of the larger peptides by 8–9 mers.

The following table shows the temperatures (in °C.) at which 50% of the Class I MHC heavy chains (indicated) are stable in the TX100 lysates, when co-expressed with murine or human β2 in the presence or absence of peptides.

TABLE 1

| MHC Class I | Peptide | Mouse β2 | Human β2 |
| --- | --- | --- | --- |
| H2-$K^b$ | — | 24 | 32 |
| | OVA 8 | 45 | 47 |
| | OVA 9 | 46 | 48 |
| | VSV 8 | 26 | 34 |
| H2-$D^b$ | — | 27 | 34 |
| | INF NP9 | 42 | 44 |
| H2-$L^d$ | — | 23 | 29 |

In order to address the question of whether peptide could bind to empty Class I molecules in the absence of β2 microglobulin, detergent lysates were prepared from Drosophila cells expressing $K^b$ or $D^b$ Class I heavy chains labelled with 35S methionine for one hour and treated. The $K^b$ molecule was immunoprecipitated with the Y3 antibody and $D^b$ with the B22.249 antibody. Only low levels of immunoreactive $K^b$ heavy chain could be detected in the untreated lysates. Addition of either peptide that binds to the Class I or human β2 microglobulin results in an increase in the amount of immunoreactive material; addition of both resulted in a much greater amount of immunoreactive heavy chain. Similar results were obtained for $D^b$. Thus, it appears that heavy chain can bind peptide in the absence of β2 microglobulin; however, either this binding does not result in a very stable conformation, or the antibodies used do not bind this conformation well. Addition of β2 microglobulin also leads to an increase in the number of immunoreactive molecules presumably for the same reason. The effects of these two reagents are additive, suggesting that the triple complex is the most stable form of the molecule and/or that this molecule is the best recognized by the antibody.

These results raise the question of whether one can "rebuild" heavy chain/β2 complexes from the lysates after the 30° C. temperature treatment. Lysates from Drosophila cells expressing $K^b$/β2 were treated for one hour at 30° C., after which NP peptide and human β2 microglobulin were added. After incubation at 4° C. for hours, Class I heavy chains were immunoprecipitated with either Y3 or the anti-cytoplasmic tail antibody K193. Preparation of the antisera is described in Example 2.1.

As previously reported, it was found that temperature treatment of empty Class I molecules in Triton TX-100 lysates did not result in their degradation (the $K^b$ molecule can be immunoprecipitated equally well after the 30° C. treatment with an anti-cytoplasmic tail antibody K193), rather it resulted in their denaturation. Furthermore, the conformation assumed by these heat denatured molecules is such that they no longer bind β2 microglobulin or can be recovered into molecules that are recognized by Y3 by addition of peptide and human β2 microglobulin. Thus, it is reasonable to conclude that Class I heavy chains can bind peptide either alone or when they are complexed with β2 microglobulin.

Surface expression of peptide-loaded human Class I MHC, however, appears to be best facilitated by loading the molecules with peptide after the heavy chains have complexed with β2 microglobulin.

2. Expression of Human MHC

Once we determined that the thermostability of a Class I molecules is dependent on the origin of β2 microglobulin, the presence of peptide, and the length and sequence of this peptide, we utilized this information in the creation of cell lines capable of specifically activating CD8 cells via the expression of peptide-loaded human Class I MHC molecules.

Thermolability appears to be an inherent property of Class I molecules; it has presumably evolved to ensure that Class I molecules which contain either no peptide or a peptide of poor binding properties (that confers little thermostability) self-destruct. In this way, the cell minimizes the number of empty Class I molecules on its-surface, for such a situation would presumably be dangerous in that exogenously derived peptides could be bound and presented. Human Class I molecules (B27 and A2.1) expressed in insect cells with human β2 are not stable to extended incubation at 37° C.; neither are human Class I molecules expressed in the mutant cell line T2 which has been shown to be deficient in peptide loading onto the Class I molecules (Hosken and Bevan, *Science* 248:367–70 (1990); Cerundolo, et al., *Nature* 345:449–452 (1990)). Thus, it seems that the affinity between the heavy chain and β2 microglobulin has been carefully conserved through co-evolution of the molecules such that empty Class I molecules, or those carrying poorly-binding peptides, self-destruct at the body temperature of the "host" organism.

Human Class I MHC molecules were expressed in Schneider cells. Cell lines co-expressing human β2 microglobulin and HLA A2.2Y, HLA A2.1, HLA B7, or HLA B27 were established using previously-described methods. Briefly, cDNAs encoding the above proteins were cloned into the Drosophila expression vector pRmHa-3 and cotransfected with a human β2 microglobulin-containing plasmid and phshsneo plasmid into Schneider cells via methods disclosed herein. Three to four weeks later, the population of G418-resistant cells was diluted 1:5 with fresh selection media. Once a healthy growing population of cells was obtained, $CuSO_4$ was added to an aliquot of cells and 24 hours later, cells were analyzed via flow cytometry using a monoclonal antibody W6/32 (ATCC HB95, Bethesda, Md.) which recognizes a monomorphic determinant of human Class I heavy chains when they are in association with β2 microglobulin. (See Barnstable, et al., *Cell* 14:9 (1978).) High levels of surface expression of each of the human Class I molecules were induced by the addition of $CuSO_4$ (data not shown). These stable populations were sorted for high expressing cells using cytofluorimetry as described below. It is these sorted populations of cells which were used for all subsequent experiments.

Twenty-four hours prior to FACS analysis, $CuSO_4$ is added to the stably transfected Schneider cells ($3-4 \times 10^6$ cells/ml) to a final concentration of 1 mM, thereby "switching on" expression from the transfected genes. Cells are plated out in 24-well cluster dishes (2 ml per well). Eight hours prior to FACS analysis, the $CuSO_4$ medium is replaced with fresh medium (1 ml) with or without peptide at a concentration of 50 μg/ml. 37° C. temperature challenges are carried out by transferring the dishes onto a flat surface in a 37° C. room at various time intervals prior to harvesting the cells for analysis.

To analyze surface expression of Class I MHC on the Schneider cells, aliquots of cells ($5 \times 10^5$) are transferred into tubes on ice, collected by centrifugation (1,000×g for 4 minutes), resuspended in 3 ml of PBS/1% BSA, 0.02% sodium azide, collected by centrifugation and resuspended in PBS/BSA (0.5 ml) containing the appropriate primary antibody (ascites fluids Y3, 28:14:8S, 30.5.7, W6/32, diluted 1:200). Rabbit antisera are diluted 1:500 and B22.293 hybridoma supernatant is used directly. After a one hour incubation on ice, cells are washed twice in 3 ml of PBS/BSA and resuspended in 0.5 ml of PBS/BSA containing FITC labelled secondary antibody (Cappell, Durham, N.C.) and 1 mg/ml propidium iodide. After a 30 minute incubation on ice, cells are washed once with PBS/BSA and resuspended in this buffer at a concentration of $1 \times 10^6$/ml. Samples are then analyzed by FACS 440 (Becton Dickinson). Dead cells stained with propidium iodide, are excluded by including a live gate in the analysis.

For cell sorting, the same procedure outlined above is used, except that all staining operations are carried out in a sterile hood. Solutions, including antibodies, are filter-sterilized, and Schneider media or Excell 400 is used in place of PBS/BSA. Cells that specifically bound the primary antibody are sorted using a Becton Dickinson cell sorter. Sorted cells ($2- 8 \times 10^5$) are washed once in medium before plating out at a concentration of $2 \times 10^5$ cells/mi.

In order to demonstrate that the human Class I molecules expressed on the surface of the Drosophila cells were empty, the cells were incubated at 37° C. for two hours and the cell surface expression was analyzed by cytofluorimetry. The surface expression of both HLA B27 and A2.1 is greatly reduced if cells are incubated at 37° C. for 2 hours; however, preincubating the cells in HIV peptides known to bind to the Class I molecules affords significant thermal stability to the Class I, while peptides that do not bind have little effect (see FIG. 5A). (A 9-amino acid peptide ILKEPVHGV (SEQ ID NO 31) from the POL protein of HIV binds and stabilizes HLA A2.1. A nine-amino-acid peptide from the Vpr protein of HIV binds and stabilizes B27 (FRIGCRHSR; SEQ ID NO 30). These data show that the human Class I molecules expressed on the surface of Drosophila cells are empty and can be stabilized by binding specific HIV peptides.

FIG. 5A shows peptide-induced thermostabilization of HLA B27 and HLA A2.1 expressed on the surface of Drosophila cells by HIV peptides. Drosophila cells expressing either HLA B27 or A2.1 were incubated with peptides where indicated and then either maintained at 28° C. or incubated at 37° C. for two hours prior to analysis of the surface expression of the Class I molecules by use of the antibody W6/32 (from ATCC HB95) and cytofluorimetry. The mean fluorescence of each cell population is shown plotted against the incubation conditions The HIV POL peptide (ILKEPVHGV, SEQ ID NO 31) stabilizes A2.1 but not B27, while the HIV Vpr peptide (FRIGCRHSR, SEQ ID NO 30) stabilizes B27, but not A2.1.

FIG. 5B illustrates that HLA A2.2Y expressed in Drosophila cells has the characteristics of empty Class I molecules in Triton X100 lysates. Radioactive Triton X100 lysates prepared from Drosophila cells expressing A2.2Y were aliquoted and peptide additions made as follows: A and B: no additions; C: an HIV GAG (B) peptide KRWIILGLN (SEQ ID NO 29); D: Influenza peptide ILGFVFTLTV (SEQ ID NO 32); E: random 8 mer peptide; F: random 9 mer peptide. Aliquots B–F were incubated at 37° C. for one hour prior to immunoprecipitation with W6/32 and SDS PAGE analyses.

FIG. 5C shows that HLA B7 expressed in Drosophila cells has the characteristics of empty Class I molecules in Triton X100 lysates. Lysates were prepared as in FIG. 5B, in Drosophila cells expressing HLA B7. Aliquots received no peptide (–P) or random 18 mer or 9 mer peptide as indicated. Half of the aliquots were incubated at 39° C. for one hour prior to immunoprecipitation with W6/32 and SDS PAGE.

HLA B7 and A2.2Y expressed in Drosophila cells were also shown to be empty in that they were found to be thermolabile in Triton TX100 cell lysates (see FIG. 5B and 5C); however, they could be stabilized by addition of peptides to the lysates prior to the temperature challenge. In particular, a 10 mer derived from influenza matrix, ILGFVFTLTV (SEQ ID NO 32) (Gotch, et al., *J. Exp. Med.* 168:2045–57 (1988)), can be seen to stabilize HLA A2.2 as does a random 9 mer peptide which also stabilizes HLA B7.

The temperature challenge assay of Triton TX100 cell lysates was carried out as previously described herein for murine Class I. The conclusion from these studies is that human Class I molecules expressed in Drosophila cells have all the characteristics of the empty molecules expressed in the mutant human cell line T2 (Salter, et al., supra (1985); Hosken and Bevan, supra (1990)).

Example 2

Generation of Peptides with Optimal Binding Characteristics for Class I Molecules A. Discussion and Overview Recent data have demonstrated that Class 1 molecules bind peptides, which contain consensus sequence motifs. (See Falk, et al., *Nature* 351:290–6 (1991); Van Bleek and Nathenson, *Nature* 348:213–6 (1990).) Thus, the amino- and carboxyl-terminal residues of peptides bound to a given allelic form of Class I molecule seem to be restricted to a few types of amino acids and one or more internal residues may have to occupy specific positions. In addition, the overall lengths of Class I-bound peptides seem to be confined to 8 or 9 amino acid residues. Falk, et al., supra (1991); Van Bleek and Nathenson, supra (1990). Examination of the binding of peptides to the murine $K^b$ molecule confirms that an ovalbumin peptide, OVA-8 with the sequence SIINFEKL (SEQ ID NO 23, residues 5–12), which binds to $K^b$ molecules in vivo, contains an optimal binding motif and binds strongly to $K^b$ molecules in vitro. As this peptide sequence in the ovalbumin molecule is flanked by the sequences ... QLE and TEW ..., it is apparent that either several proteases, a protease with very broad substrate specificity, or an enzyme complex with multiple proteolytic activities must be responsible for generating the OVA-8 peptide from intact ovalbumin.

To examine whether isolated proteasomes can generate the optimal peptide for binding to $K^b$ molecules, it was helpful to make use of the finding that "empty" Class I $K^b$ molecules, i.e., those without bound peptide, are very thermolabile (Ljunggren, et al., supra (1990)). Incubation of "empty" $K^b$ molecules in detergent at 30° C. for one hour renders the β 2M-dependent, $K^b$-specific antibody Y3 unable to react with the $K^b$ molecule because β 2M dissociates rapidly from the heavy chain. The binding of a suitable peptide such as OVA-8 prevents the subunit dissociation permitting Y3 to bind the Class I complex. Peptides of the same length as OVA-8, which cannot be presented by $K^b$ molecules in vivo (e.g., the peptide SNENMETM (SerAsnGluAsnMetGluThrMet) (SEQ ID NO 25, residues 2–9) which binds to $D^b$, Townsend, et al., *Cell* 44:959–968 (1986)) was unable to prevent the heat-induced. dissociation of the $K^b$ Class I molecules (see FIG. 3). The peptide OVA-24 with the sequence EQLESIINFEKLTEWTSSNVMEER (SEQ ID NO 23) (which encompasses the sequence of OVA-8, shown underlined) binds weakly to $K^b$ molecules. However, the weak binding of OVA-24 was not sufficient to prevent the $K^b$ β 2M complex from dissociating at 30° C.

The various antisera used were prepared as follows. Antiserum K193 is generated by immunizing rabbits with Keyhole Limpet Lymphocyanin (Calbiochem, La Jolla, Calif.) conjugated to synthetic peptide corresponding to the COOH terminal sequence of H-2$K^b$ (LPDCKVMVHDPSLA or LeuProAspCysLysValMetValHisAspProSerLeuAla) (SEQ ID NO 33). Y3 ascites is prepared using hybridoma HB176 (ATCC, Rockville, Md.). (See also Hammerling, et al., *PNAS USA* 79:4737–4741 (1982).) Ascites 28-14-8S is prepared from hybridoma HB 27 (ATCC, Rockville, Md.). (See Ozato and Sachs, *J. Immunol.* 126: 317–321 (1980); Myers, et al., *J. Immunol.* 142: 2751–58 (1989).) Ascites 30-5-7 is prepared from culture supernatant from hybridoma B22.249 (See Hammerling, et al., *Immunogenetics* 8:433–445 (1979); Allen, et al., *Nature* 309:279–81 (1984).) Polyclonal antisera against purified murine MHC are prepared according to Kvist, et al., *Scand. J. Immunol.* 7:265–76 (1978). FITC labelled secondary antibodies (affinity purified goat anti-mouse and goat anti-rabbit IgG) are obtained from Cappell (Durham, N.C.).

Using this assay system, biosynthetically labeled, "empty" $K^b$ molecules from RMA-S cells, which fail to load peptides onto Class I molecules, were incubated with the β 2M-dependent, $K^b$-specific monoclonal antibody Y3. Antibody-bound molecules were separated by SDS-PAGE and visualized by autoradiography. SDS-PAGE analysis is carried out as follows. Immunoprecipitates collected by protein A sepharose beads are washed five times with 1 ml of 0.1% TX100/PBS and immediately boiled in SDS PAGE sample buffer or where indicated after digestion of half of the sample with Endoglycosidase H (see Jackson, et al., *EMBO J.* 9:3153–3162 (1990)). Samples are then analyzed on 10–15% gradient SDS PAGE gels which are treated with Amplify (Amersham, Arlington Heights, Ill.) prior to autoradiography at –70° C. using Kodak (Rochester, N.Y.) XOmat AR film.

The bands corresponding to the $K^b$ chain were quantitated by densitometry. To generate the data (not shown), "empty" Class I $K^b$ molecule-containing lysate of RMA-S cells was incubated with peptide and/or purified proteasomes before incubation at either 4° C. or 30° C. for one hour. $K^b$ molecules were immunoprecipitated with the monoclonal antibody Y3 and analyzed by SDS-PAGE. "Empty" $K^b$ molecules were incubated with OVA-24; proteasomes alone; OVA-24 and proteasomes; OVA-24, proteasomes, and p-hydroxymercuribenzoate; and OVA-8. "Empty" $K^b$-containing lysate alone was analyzed (data not shown). Prior to immunoprecipitation, samples were heat challenged at 30° C. for one hour or kept at 4° C. for the same time period (data not shown). The OVA-8 peptide was used at a final concentration of 75 μM and the OVA-24 peptide at a concentration of 75 μM.

$K^b$ molecules incubated overnight at 4° C. dissociated almost completely as judged by their lack of reactivity with the antibody, but were quantitatively recovered from the incubation mixture, which contained the OVA-8 peptide.

Densitometric scans of the even-numbered lanes (not shown) permitted a determination of the amount of $K^b$ recovered after the heat challenge. The data were expressed as percentages of the amount of $K^b$/OVA-8 complexes recovered after the heat challenge. The majority of the $K^b$ molecules, which had been incubated with OVA-8, remained intact after the 30° C. treatment. The longer peptide, OVA-24, was not as efficient as OVA-8 in stabilizing the $K^b$ molecules, and in accordance with our previous data on the weak binding of OVA-24, only about 30% of the $K^b$ molecules remained after the heat treatment. When the incubation mixture contained the OVA-24 peptide and purified proteasomes, an increased amount of $K^b$ molecules could be immunoprecipitated and approximately 80% of the $K^b$ molecules survived the exposure to 30° C. That the increased stability of the $K^b$ molecules was due to peptide(s) derived from OVA-24 was apparent from the fact that proteasomes alone failed to generate peptides in the lysate that could prevent dissociation of the $K^b$-β 2M complex. This conclusion is also supported by the fact that proteasomes treated with the inhibitor p-hydroxymercuribenzoate (Rivett, *Arch. Bioch. Biophys.* 268:1–8 (1989)) failed to generate peptides from OVA-24, which could stabilize the $K^b$ molecules at 30° C.

These data demonstrated that isolated proteasomes could generate peptide(s) from a weakly $K^b$-binding precursor peptide, such that the Class I molecule was stabilized to the same extent as by endogenous peptides. Consequently, the peptide(s) derived from OVA-24 must have been about 8 amino acids long and must have encompassed the sequence of the OVA-8 peptide. In addition, similar experiments in which denatured, reduced, and alkylated ovalbumin was incubated with proteasomes also resulted in the recovery of thermostable $K^b$ molecules (data not shown).

B. Procedures
1. Cell Cultures

HeLa cells (ATCC No. CCL 185) were grown in Dulbecco's modified Eagle's medium (DMEM, Gibco, Grand Island, N.Y.) supplemented with 8% fetal calf serum, 2 mM glutamine, penicillin (100 μg/ml), and streptomycin (100 μg/ml). Splenocytes of four different H-2 haplotypes (H-$2^k$, $^{s,d}$, and $^q$), RMA-S, T1, T2 and murine astrocytes were grown in RPMI 1640 medium (Gibco, Grand Island, N.Y.). RMA-S, a murine mutant H-$2^b$ lymphoma cell line (Ljunggren and Karre, *J. Exp. Med.* 162:1745–59 (1985); Karre, et al., *Nature* 319:675–8 (1986)), is unable to present endogenous antigens (Townsend, et al., *Nature* 340:443–8 (1989); Townsend and Bodmer, *Ann. Rev. Immunol.* 7:601–24 (1989)). T1 and T2 are derivatives of the human mutant B lymphoblastoid cell line LBL 721.174 (0.174) fused to the T cell lymphoma CEM (Salter et al., *Immunogenetics* 21:235–7 (1985)). T1, the 0.174-CEM hybrid, expressed high levels of Class I MHC derived from 0.174. T2, selected for loss of both copies of human chromosome 6, has the low Class I expression phenotype of 0.174 (Hosken and Bevan, *Science* 248:367–70 (1990)).

2. Metabolic Radiolabeling, Immunoprecipitation, and Densitometry

Metabolic labeling of cells was carried out as described in Jackson, et al. (*EMBO J.* 9:3153–3162 (1990)), with the following modifications. Unless otherwise stated, cells were treated with interferon gamma (IFN-gamma; Boehringer Mannheim, Indianapolis, Ind.) (2500 U/ml) for 96 hours prior to the metabolic labeling. Pulse-media contained 0.15 mCi/ml of L[35S]methionine-deficient and cysteine-deficient DMEM. Cells were routinely labeled for 4 hours followed by chase periods of different lengths of time (up to 36 hours) in the presence of normal culture medium. Immunoprecipitation, SDS-PAGE (Blobel and Dobberstein, *J. Cell. Biol.* 67:835–51 (1975)) and fluorography (Bonner and Laskey, *Eur. J. Biochem.* 46:83–88 (1974)) were carried out as described (Jackson, et al., *EMBO J.* 9:3153–3162 (1990)). First dimension nonequilibrium pH gradient gel electrophoresis (using ampholines pH 3.5–10) was performed as described in Jones, in *Selected Methods in Cellular Immunology*, Mishell and Shigii, eds., Freeman, San Francisco, 1980, pp. 398–400. To quantify radioactivity incorporated into protein, band intensities on the fluorographs were determined by scanning densitometry using an LKB Ultroscan XL (Brouma, Sweden). The radioactive marker proteins, bovine serum albumin (67 kD), ovalbumin (46 kD), carbonic anhydrase (30 kD) and lactoglobulin A (18.4 kD) were purchased from New England Nuclear (duPont, Boston, Mass.).

For pulse chase analysis, lysates from the various time points are aliquoted into tubes depending upon the number of antibodies being used to analyze transport. Antibody is added to the lysate (1 μl of ascites fluid, Y3, 30.5.7, 28:14:8S; W6/32), or antiserum (K193, K270), 100 μl of hybridoma culture supernatant (antibody B22.293); the mixture is then left for 2–12 hours prior to collection of the antibody by incubation with protein A sepharose for one hour and a 5-second spin in the microfuge.

3. Antisera, Monoclonal Antibody and Peptides

Rabbit anti-human and anti-rat proteasome sera were kindly provided by Dr. A. Ichihara (Tanaka, et al., *J. Cell. Physiol.* 139:34–41 (1986)). Y3 ascites, a monoclonal antibody against mouse H2-$K^b$, was prepared by using hybridoma no. HB 176 from ATCC (Hammerling, et al., *PNAS USA* 79:4737–4741 (1982)). IFN-gamma from human T-lymphocytes was obtained from Boehringer Mannheim (Indianapolis, Ind.). Mouse IFN-gamma was obtained from Genentech (South San Francisco, Calif.) and Amgen Biologicals (Thousand Oaks, Calif.). Peptides were synthesized by solid-phase techniques on an Applied Biosystems 430A peptide synthesizer and further purified on a $C_{18}$ reversed phase chromatography column (VyDac).

4. Ammonium Sulfate Fractionation of HeLa Cell Homogenates

Homogenized HeLa cells, untreated and IFN-gamma-treated, were centrifuged to remove nuclei and cell debris, and the resultant supernatants were subjected to ammonium sulfate fractionation as described (Rivett, *J. Biol. Chem.* 260:12600–12612 (1985)). 26S proteasome complexes present in the supernatant were selectively precipitated with ammonium sulfate at 38% saturation while 19S proteasome complexes present in the supernatant after the 38% fractionation step were precipitated at 60% ammonium sulfate (Waxman, et al., *J. Biol. Chem.* 262:2451–57 (1987)).

5. Fractionation of Microsomes and Cytosol

Untreated and IFN-gamma-treated HeLa cells were labeled for 4 hours, homogenized, and subjected to differential centrifugation. The homogenates were first spun at 15,000 rpm for 30 minutes to remove nuclei and cell debris. The resulting supernatants were then spun at 100,000×g for 30 minutes to pellet microsomes. The proteasomes in the supernatant fractions (cytosolic fraction) and in the pellets (crude microsomal fraction) were separately immunoprecipitated and analyzed by two-dimensional gel electrophoresis.

6. Purification of Proteasomes

Proteasomes were purified from fresh bovine liver using a modification of the procedure described by Skilton, et al. (1991). Briefly, fresh bovine liver was homogenized in 10 mM Tris-HCl (pH 7.2), 50 mM KCL, 0.1 mM EDTA, 0.1 mM DTT, and 20% glycerol (v/v) ("buffer A"). The homogenate was centrifuged at 105,000×g for one hour. The supernatant was first treated with ammonium sulfate to 38% saturation in order to remove large protein aggregates as well as the 26S form of the proteasome (Waxman, et al., *J. Biol. Chem.* 262:2451–57 (1987)). The remaining supernatant was then treated with ammonium sulfate to 60% saturation in order to selectively precipitate the 19S form of the proteasome. The pellet was resuspended in a small volume of buffer A. The resuspended 60% ammonium sulfate fraction was subjected to three sequential chromatography steps: DEAE-Sepharose, anion-exchange chromatography on Mono Q 10/10, and finally gel filtration on a Superose 6 column. After each chromatography step, proteasome-containing fractions were identified by SDS-PAGE and by analysis of peptidase activity as described in Hough, et al., *J. Biol. Chem.* 262:8303–8313 (1987). The peptide substrates used were: N-succinyl-ala-ala-phe-MCA, N-succinyl-leu-leu-val-tyr-MCA, and t-butoxycarbonyl-phe-ser-arg-MCA.

7. Peptide Binding Assay

"Empty" Class I $K^b$ molecule-containing lysate of RMA-S cells was prepared using a modified procedure (Ljunggren, et al., *Nature* 346:476–80 (1990)). Briefly, RMA-S cells were cultured in RPMI 1640 at 26° C. for 8 hours. The cells were then rinsed once in PBS and again incubated at 26° C. in medium containing 0.25 mCi/ml of L-[$^{35}$S]methionine and 0.25 mCi/ml of L-[$^{35}$S]cystine in methionine-deficient and cystine-deficient RPMI 1640 and normal RPMI 1640 medium at a ratio of 10:1 for 16 hours. Cells were rinsed in PBS and lysed as described above. "Empty" Class I $K^b$ molecules-containing lysate was then incubated with peptides and/or purified proteasomes at 26° C. for 1 hour before being subjected to incubation at 30° C. for an additional hour. This mixture was then subjected to immunoprecipitation with the monoclonal antibody Y3 and analyzed by SDS-PAGE.

Example 3

Induction of Cytotoxic Effectors In Vitro

A. Osmotic Loading

Osmotic loading of SC2 and 3T3 cells with ovalbumin protein was carried out as described by Moore, et al., *Cell* 54:777–785 (1988). The assay procedure is as follows. In a 96-well dish, 1×10$^5$ Drosophila cells (with or without peptide/protein loaded) or 3T3 cells were cocultured with 1×10$^5$ B3/CD8 T cell hybridoma cells in 200 µl of RPMI media supplemented with 10% fetal bovine serum. After 24 hours of incubation, 100 µl of the supernatant from these cultures was added to 100 µl of RPMI containing 5,000 CTLL cells. The cells were cocultured for 24 hours at 37° C. when 1 µCi of $^3$H thymidine (Amersham) was added. After a further incubation of 15 hours at 37° C., the incorporation of radiolabel into the CTLL cells was determined by scintillation counting.

Assays conducted with murine MHC also verified that the insect cells are capable of loading peptide onto the Class I molecules. Cells expressing as few as 200–500 MHC molecules containing a particular antigen can be detected by a T cell. As the Drosophila cells do not accumulate chromium, an antigen presentation assay based on B3/CD8, a T cell hybridoma, was used. B3/CD8 is a hybridoma between B3, cytotoxic T cell specific for ovalbumin peptide 253–276 presented by H-2K$^b$ Class I molecules, and CD8- bearing IL-2 -secreting cell line (see Carbone, et al., supra, 1989). Upon antigenic stimulation, B3/CD8 produces IL-2, measured by $^3$H thymidine incorporation in IL-2 -dependent cell line CTLL (Gillis, et al., *J. Immunol.* 120:2027 91978)). Thus, by measuring the amount of IL-2 produced, one can assay for T cell recognition.

Figure 4:
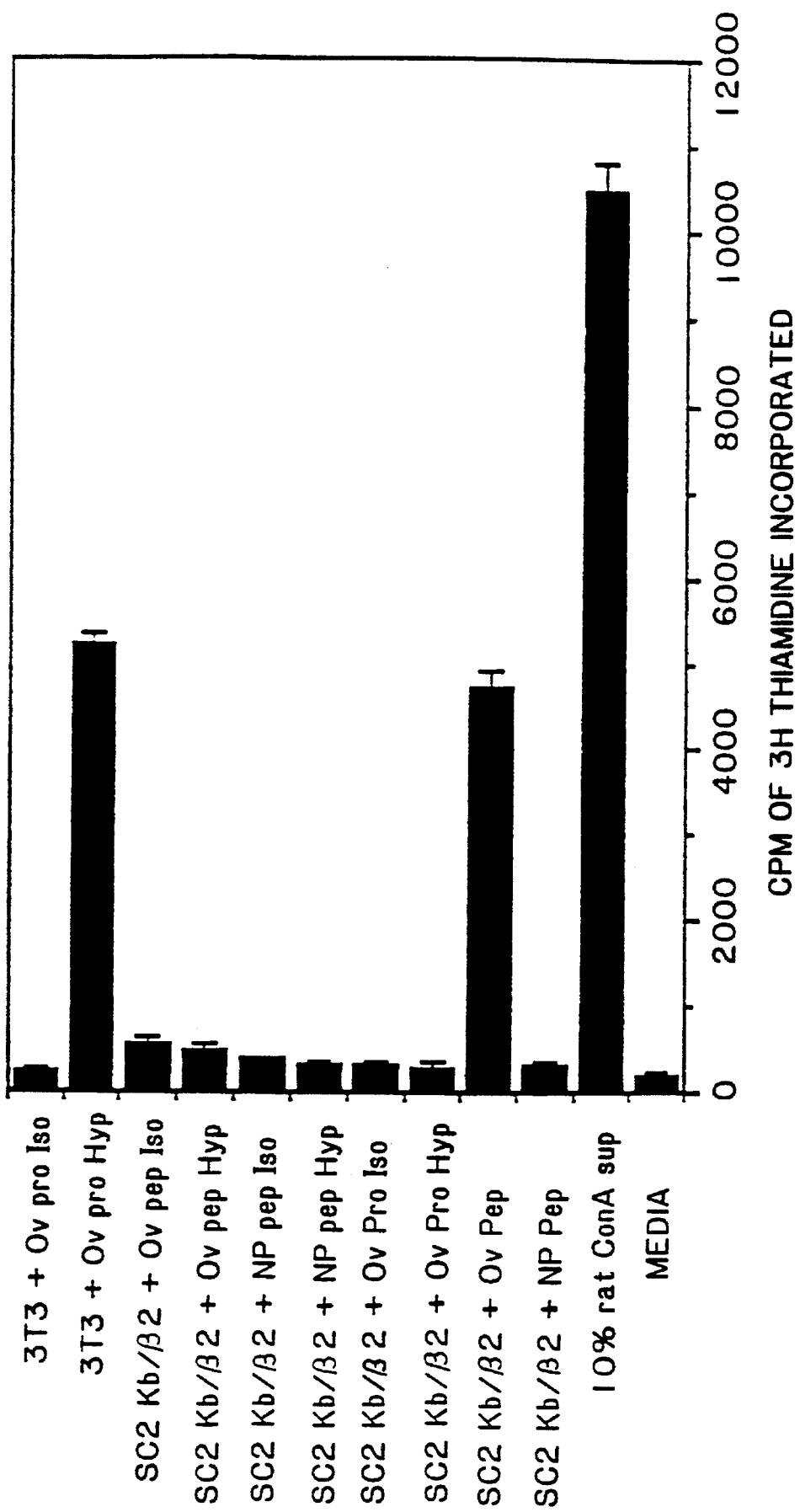
FIG. 4 illustrates data from an experiment designed to determine whether insect cells can process antigen and load it onto the Class I molecules, and whether the latter can present either endogenously or exogenously derived antigen to T cells. Schneider 2 (SC2) or 3T3 cells transfected with $K^b$/β2 were incubated with ovalbumin protein (OvPro) or ovalbumin peptide, OVA 24 (OvPep) in isotonic (Iso) or hypertonic (Hyp) media. (Murine cell line BALB/3T3 is available from the ATCC under accession number CCL 163.) After treatment, cells were cocultured with the T cell hybridoma B3/CD8. B3/CD8 is a T cell hybridoma between B3 (Carbone, et al., *J. Exp. Med.* 169: 603–12 (1989)), cytotoxic T cell specific for ovalbumin peptide 253–276 presented by H-2$K^b$ Class I molecules, and CD8-bearing IL-2-secreting cell line. Upon antigenic stimulation, B3/CD8 produces IL-2, measured by $^3$H thymidine incorporation in IL-2-dependent cell line CTLL (Gillis, et al., *J. Immunol.* 120:2027 91978)). Thus, by measuring the amount of IL-2 produced, one can assay for T cell recognition.

In order to provide an intracellular pool of ovalbumin protein from which OVA peptides can be derived, ovalbumin (Sigma Chem. Co., Mo.) was osmotically loaded into the cells as described by Moore, et al, supra (1988). Immediately after loading, the cells were mixed with the T cell hybridoma. After two days' incubation, the medium was removed and assayed for IL-2. The amount of IL-2 was determined by the ability of the medium to support the growth of the IL-2 -dependent cell line CTLL (Gillis, et al., supra, 1978), and growth was quantitated by the amount of radioactive thymidine incorporated into the cells. It can be seen in FIG. 4 that the T cells responded well to the Drosophila cells if the ovalbumin peptide was added to the culture medium, but no recognition occurred if the cells were loaded with the ovalbumin protein. The MHC Class I molecules expressed on the cell surface of the insect cell are fully functional in that they can bind peptide if it is added to the culture medium and can present it in the correct context for it to be recognized by a T cell.

B. Optimization of In Vitro Conditions

For the optimization of in vitro conditions for the generation of specific cytotoxic T cells, the culture of Drosophila cell stimulator cells is preferably maintained in serum-free medium (e.g. Excell 400). Drosophila cell stimulator cells are preferably incubated with >20 µg/ml peptide. The effector:stimulator ratio (lymphocyte:Drosophila cell ratio) is preferably in the range of about 30:1 to 300:1. The maximum specific CD8 is generally observed after five days of culture. The culture of target cells for killing assay is preferably maintained in a serum-free medium.

C. $^{51}$Cr Release Cytotoxic Assay

Cell mediated cytolytic activity was detected with a Cr$^{51}$ or release assay. The percentage of specific lysis of 10$^4$ $^{51}$Cr-labeled target cells in 200 µl was determined for various lymphocyte to target cell ratios and dose-response curves for each lymphocyte population by plotting specific cytotoxicity versus the log 10 of the viable effector number. Spontaneous $^{51}$Cr release values varied between 5% and 15% of the total incorporated label. The percentage of specific $^{51}$Cr release was calculated according to the following formula: (ER-MR) (MR-SR)×100, where ER is the observed experimental $^{51}$Cr release, SR is the spontaneous release detected by incubating the target cells in culture medium alone, and MR is the maximum of radioactivity released from the target cells after incubation in 200 μl in HCl for the duration of the assay.

D. Induction of Cytotoxic Effectors by Primary in Vitro Stimulation with Drosophila Cells Expressing Murine Class I and Peptides Peptide OVA, NP (influenza) and NP (LcMV) were used as a source of peptides to assess their ability to generate a primary in vitro CD8 response. (See FIGS. 6A and B.) A five day incubation of spleen cells from immunized C57BL/6 and Balb/c mice with respective Drosophila cells expressing H2-$K^b$+antigen and H2-$L^d$+antigen generated effectors that efficiently lysed the tumor EL4 and P815 in the presence of peptides.

P815 (ATCC TIB 64) (H-$2^d$) is a mastocytoma from DBA/2 mice. EL4 (ATCC TIB 39) is a thymoma from C57BL/6 (H-2b). EL4 is transfected with OVA cDNA in a plasmid construct with the human β actin promoter to derive the OVA production cell line EL4-OVA. These tumors are maintained as stationary suspension cultures in RPMI 1640 supplemented with 10% fetal bovine serum FBS (see Moore, et al., *Cell* 54:777–785 (1988)). Jurkat (ATCC CRL 8163) is a human cell line expressing HLA B7. Jurkat A2 is a transfected cell line produced by transfecting Jurkat cells with HLA A2-1, e.g., via methods disclosed herein. (See also Irwin, et al., *J. Exp. Med.* 170:1091–1101 (1989).)

Synthetic peptides can substitute for endogenously synthesized viral proteins during CD8 recognition. The specific CD8 generated could recognize endogenously synthesized peptides presented by Class I at the surface of EL4 (transfected with an ovalbumin cDNA). (See Moore, et al., *Cell* 54:777–785 (1988).) Similarly, the CD8 generated in vitro against $D^b$ loaded with influenza NP peptide recognized EL4 target cells infected with influenza virus strain A/PR/8 (See FIG. 7.) (See Carbone, et al., *J. Exp. Med.* 167:1767–1779 (1988); strain A/PR/8/34 is also available from the American Type Culture Collection and has accession no. ATCC VR-95).

E. Characterization of Antipeptide Cytotoxic Cells

To determine whether peptide specific recognition was indeed due to T cell activity, these lines were treated with anti-CD8 (OKT8, ATCC No. CRL 8014) or anti-CD4 (OKT4, ATCC No. CRL 8002) and/or complement, before their addition to assay culture. Only anti-CD8 treatment abolished the cytotoxicity.

These specific CD8s were tested on 3T3/$D^b$ and 3T3/$K^b$ cells, produced by transfection of BALB 3T3 (ATCC, CCL 163) cells with either $D^b$ or $K^b$, respectively. (Other readily-available 3T3 cultures are also available for use, including ATCC CCL 163.2.) Preferably, stable transfectants are prepared via cotransfection of 3T3 by pCMU/$K^b$ or pCMU/$D^b$ and pSV2neo and selected with G418. (See also Joly and Oldstone, supra (1991). The anti-OVA CD8 response was $D^b$ or $K^b$ restricted, confirming that these activities show classical Class I MHC restriction.

The ability to elicit CD8 by peptide stimulation affords one a relatively simple technique with which to study Class I restricted recognition. Since T cells are specific for denatured rather than natural forms or foreign antigens, peptides clearly represent a potential means of effective vaccination.

F. Generation of Specific CD8 Cells

Drosophila cell peptide Class I complexes were fixed with glutaraldehyde 0.001% and were then washed and used as stimulators in lymphocyte co-culture. A very weak cytotoxic activity was detected after 5 days of co-culture, confirming that live (i.e., unfixed) Drosophila cells are superior in generating specific CD8. Addition of 10% Drosophila culture supernatant to the fixed cells restores the generation of specific CD8. (See FIGS. 8A and B.)

Cultured cells expressing the syngeneic Class I antigens, which ordinarily failed to activate CD8 in primary culture, were able to generate specific CD8 after the addition of Drosophila cell culture supernatant.

Removal of CD4+ and Class II+ cells from the responder population diminishes the CD8 activity generated with peptide loaded on Drosophila cells. Thus, primary responses induced by peptide-loaded Drosophila cells appear to be CD4+ cell and Class II dependent.

Example 4

In Vivo Efficacy of Treatment

A. Rejection of Tumors

Using the within-disclosed methods, it is now possible to specifically kill target cells in humans using the specific, activated CD8 cells of the present invention. Essentially, the treatment methodology includes the following steps:(1) obtaining a fluid sample containing T cells from an individual to be treated; (2) loading empty Class I MHC molecules with at least one species of antigenic peptide, wherein the peptide is substantially homologous to at least a portion of a peptide derived from the target cell; (3) admixing the T cells in vitro with an amount of peptide-loaded Class I MHC molecules sufficient to produce activated CD8 cells; (4) harvesting the activated CD8 cells from the culture; and (5) administering the activated CD8 cells to the individual to be treated.

This methodology is already showing promising results in a mouse model. For example, in one study, C57BL/6 female mice (about 6–8 weeks old) were injected subcutaneously with three million (3 MM) EL4/OVA tumor cells just behind the ears. The tumor cells were rendered tumorigenic by a single passage in C57BL/6 mice. On the day of subcutaneous inoculation with EL4/OVA tumor cells, the mice were injected with Drosophila/$K^b$/OVA stimulated CD8 cells either next to (proximal to) the tumor cell injection site, or intravenously.

On day 8, the tumor dimensions were measured. The five control mice that received only the 3 MM tumor cells had tumors measuring 12 mm×12 mm in size. Three mice that received tumor cells and 24 MM CD8 cells injected IV were examined; the tumor sizes were (a) 2 mm×2 mm, (b) 5 mm×5 mm, and (c) 12 mm×12 mm in those mice. Five mice that received tumor cells and 24 MM CD8 cells next to the tumor injection site were examined. The results were as follows: (i) three mice had no detectable tumors on day 8; (ii) one mouse had a tumor measuring 1 mm×1 mm; and (iii) one mouse had a tumor measuring 5 mm×5 mm.

On day 11, the tumor sizes were determined to be as follows:

| Group | # Mice | Tumor Size |
| --- | --- | --- |
| Control | 3 | 15 mm × 12 mm |
| " | 2 | 20 mm × 12 mm |
| 3 MM tumor + 24 MM CD8 IV | 1 | 5 mm × 5 mm |
| " | 1 | 10 mm × 5 mm |
| " | 1 | 13 mm × 8 mm |
| 3 MM tumor + 24 MM CD8 IP | 2 | NO TUMOR |
| " | 1 | 0.5 mm × 1.0 mm |

-continued

| Group | # Mice | Tumor Size |
|---|---|---|
| " | 1 | 1 mm × 1 mm |
| " | 1 | 1.5 mm × 1.5 mm |

In a subsequent experiment, the volume of tumors in mice were measured after various regimens were applied. The mice were injected with three million (3 MM) EL4/OVA tumor cells as described above. On the day of subcutaneous inoculation with EL4/OVA tumor cells, the mice were preinjected with Drosophila/$K^b$/OVA stimulated CD8 cells either intraperitoneally, subcutaneously or intravenously, as described in Table 2 below. Tumor volume was measured on days 6, 8, 10, 12, and 20, following injection. Five mice were included in each experimental and control group. The results are set out in Table 2 below.

TABLE 2

| Mouse | #CD8/ Method | TUMOR VOLUME MEASURED, DAY | | | | |
|---|---|---|---|---|---|---|
| | | 6 | 8 | 10 | 12 | 20 |
| 1 | 30 MM, IP | 0 | 0 | 0 | 0 | 0 |
| 2 | " | 0 | 0 | 0 | 0 | 0 |
| 3 | " | 0 | 0 | 0 | 0 | 0 |
| 4 | " | 0 | 0 | 0 | 0 | 0 |
| 5 | " | 0 | 1 | 2 | 1 | 0 |
| 1 | 30 MM, IV | 0 | 0 | 0 | 0 | 0 |
| 2 | " | 0 | 0 | 0 | 0 | 0 |
| 3 | " | 0 | 0 | 0 | 0 | 0 |
| 4 | " | 0 | 2 | 3 | 2 | 0 |
| 5 | " | 2 | 3.5 | 5 | 3 | 0 |
| 1 | 15 MM, IV | 0 | 0 | 0 | 0 | 0 |
| 2 | " | 0 | 0 | 0 | 0 | 0 |
| 3 | " | 5 | 8 | 13 | 20 | +* |
| 4 | " | 5 | 10 | 20 | 25 | + |
| 5 | " | 6 | 14 | 25 | 35 | + |
| 1 | 30 MM, SC | 0 | 0 | 0 | 0 | 0 |
| 2 | " | 0 | 0 | 0 | 0 | 0 |
| 3 | " | 0 | 0 | 0 | 0 | 0 |
| 4 | " | 2 | 4 | 5 | 2 | 0 |
| 5 | " | 2 | 7 | 10 | 3 | 0 |
| 1 | $K^b$/OVA alone | 0 | 0 | 0 | 0 | 0 |
| 2 | " | 0 | 0 | 0 | 0 | 0 |
| 3 | " | 0 | 6 | 12 | 5 | 10 |
| 4 | " | 3 | 8 | 18 | 10 | 20 |
| 5 | " | 2 | 10 | 20 | 20 | 30 |
| 1 | Control | 3 | 10 | 20 | >50 | + |
| 2 | " | 4 | 18 | 30 | >50 | + |
| 3 | " | 6 | 18 | 30 | >50 | + |
| 4 | " | 7 | 24 | 35 | >50 | + |
| 5 | " | 7 | 24 | 40 | >50 | + |

IP = intraperitoneal; IV = intravenous; SC = subcutaneous; * = measurement difficult due to size, or death of animal B. Treatment of Influenza Influenza-specific CD8 populations, for example, may be generated according to the within-disclosed techniques and prove effective in protecting individuals against lethal influenza infection. The virus-reactive CD8 derived from in vitro peptide priming is capable of providing protection in vivo and suggests that primary in vitro CD8 stimulation may prove useful in the design of a wide variety of antiviral and antiretroviral vaccines.

C. In vivo Priming of Mice with Drosophila Cells Transfected with Class I

Injection of 50×10$^6$ Drosophila cells intraperitoneally (IP) led to the induction of specific CD8. Detection of this priming was carried out using limiting dilution analysis. The frequency of CD8 specific for OVA was about 10$^6$ in naive mice. After injecting Drosophila cells coated with peptide, the frequency is about 10$^3$ (data not shown).

FIG. 8 (A and B) illustrates in vivo priming with transfected Drosophila cells, wherein the responders are C57 B1/6 mouse splenocytes. In 8A, some of the cells are fixed; in 8B, the Drosophila cells are all unfixed.

For a secondary CD8 response, C57BL/6 mice were primed by one injection of Drosophila cells IP (5×10$^7$) and tested 5–15 days after immunization. (See FIG. 8B.) Induction of activated CD8 in vivo apparently stimulates the rejection of tumors.

In another experiment, C57BL/6 mice were injected subcutaneously with 3 MM EL4 OVA. Five days later, group I mice received a subcutaneous injection of 50 MM (live) Drosophila cells expressing $K^b$/OVA; group II mice received a subcutaneous injection of 50 MM fixed Drosophila cells with $K^b$/OVA; group III mice were the control group and received no additional injection on day 5. The results of the experiment are illustrated in FIG. 9, which shows that the group I mice survived the longest and survived in greater numbers.

Primary CD8 were induced by peptide-loaded Class I in Drosophila cells in B6 unprimed mice. CD8 cells were stimulated once in vitro with Drosophila cells cultured for 36 hours at 22° C. incubated with different concentrations of OVA peptides. The final minimum amount of peptide is about 20 μg/ml. The effectors were harvested and tested on RMA-S cells with 50 μg of peptides. CD8 cell populations were able to recognize RMA-S OVA-8. (See FIGS. 6A and B.)

In another experiment, ovalbumin protein was degraded with endoproteinase Glu-C (from *Staph. aureus*; Boehringer Mannheim, Indianapolis, Ind.). The mixture was added to a Drosophila cell culture with murine MHC. After about 5 days, CD8 cells were exposed to the effectors; a number of CD8 cells were able to recognize RMA-S OVA-8.

D. Peptide Titration at Target Cell Level

Recent studies have demonstrated that peptides of 9 amino acids in length are present as a minor species in preparations of synthetic peptides. Those longer than 9 amino acids bind with low affinity to the H-2$K^b$ Class I MHC molecule. Peptide titration experiments showed that a 50-fold lower concentration of a 9 mer peptide than of a 16 mer peptide is sufficient for induction of T cell response. The same peptide titration was performed for sensitization of target cells. The results indicate that target cell sensitization is accomplished with about a 1000-fold lower peptide concentration than required for in vitro response induction.

E. Generation of CD8 in Transgenic Mice

In this study, transgenic mice expressing HLA A2.1, HLA B7, and HLA B27 were used. The splenocytes of the mice were cultured with Drosophila cells expressing the syngeneic HLA (A2.1, B7, and B27, respectively). Specific CD8 responses were generated against three peptides of HIV. (See FIGS. 10A, B and C.)

Inbred mice C57BL/6y (H2$^b$) and Balb/c (H2$^d$) mice are used in these studies, as well as various transgenic mice. Transgenic mice included the following. B7 transgenic mice are produced in the laboratory as follows. Briefly, a genomic HLA-B7 clone (including several hundred base pairs of 5' and 3' flanking regions) is microinjected into B6×SJL mouse embryos (Scripps Research Institute Transgenic Facility, La Jolla, Calif.). The B7 transgenic line has been back-crossed to C57BL/6 (H2$^b$) (Scripps Research Institute Transgenic Facility, La Jolla, Calif.). B27 transgenic mice may be produced according to known methods; ours were produced by injecting genomic clones into B6×SJL embryos and back-crossing same to C57BL/6 (Scripps Research Institute Transgenic Facility, La Jolla, Calif.). (See also Krimpenfort, et al., *EMBO J.* 6(8):1673 (1987), for another method of generating B27 transgenic mice.) β2 microglobulin transgenic mice and transgenic A2-1 mice are produced in similar fashion using known techniques (see, e.g., Irwin, et al., *J. Exp. Med.* 170:1091–1101 (1989)).

F. Generation of Specific HIV CD8s in Humans

PBL from seronegative donors were tested for their ability to generate CD8s specific against two HIV peptides. These donors are HLA A2, HLA B7 or HLA B27. After 5 days of culture, a very strong CD8 activity could be detected in the culture against both HIV peptides. (See FIGS. 11 A, B, & C.)

Human PBL are isolated by Ficoll-Hypaque gradient centrifugation (Pharmacia, Piscataway, N.J.). PBL lymphoblasts are stored in liquid nitrogen after freezing in FBS containing 10% DMSO. Cell viability and lymphocyte functions are conserved.

Peptide-specific CD8 cells are generated in syngeneic primary culture with Drosophila cells expressing the syngeneic peptide Class I complex. These cultures, are established with $3 \times 10^7$ responding spleen cells of mouse or human PBL and live $10^6$ Drosophila cells in 20 ml of RPMI 1640 culture medium supplemented with $5.10^{-5}$M β mercaptoethanol 5% FBS in an upright 25 cm² flask at 37° C. in 7% $CO_2$. CD8 cells are harvested after 5 days in culture.

In another experiment, human PBL were harvested and stimulated over a 5-day period with Drosophila cells expressing human HLA A2.1 and loaded with HIV POL peptide. The stimulated PBL were then tested on Jurkat A2.1 cells infected with HIV. The results of the experiment are illustrated in FIG. 12. Human PBL stimulated in vitro were clearly able to recognize A2.1 POL on infected cells and to kill said cells.

Example 5

Direct Binding of Peptide to Soluble, Empty Class I MHC Molecules In Vitro

A. Procedures $H-2K^b$: prepared as described above in Example 1.B.

$H-2K^b$ sol: $K^b$ sol cDNA is a derivative of $K^b$, and may be mutated by PCR according to known methods, such as those described in Ennis, et al., *PNAS USA* 87:2833–7 (1990) and Zemmour, et al., *Immunogenetics* 33:310–20 (1991). Specifically, cDNA encoding a truncated $K^b$ molecule with a stop codon inserted at the end of the alpha 3 domain at amino acid position +275 is excised from the pCMU expression plasmid as a Bam HI fragment and cloned into pRmHa-3 as $K^b$ cDNA. The $K^b$ sol cDNA is a derivative of the complete $K^b$ cDNA (see above) which is used as a template in a PCR reaction using a 5' oligonucleotide that encompassed the Sty I site, and the following 3' oligonucleotide:

5' ATATGGATCCTCACCATCTCAGGGTGAGGGGC 3' (SEQ ID NO 34)

The resulting PCR fragment is blunt-end cloned into the Sma I site of pBS (Stratagene, La Jolla, Calif.), sequenced, and the remaining 5' sequence of $K^b$ cloned into the Sty I site. A cDNA encoding the complete $K^b$sol protein could be obtained as a Bam HI restriction fragment.

$H-2D^b$ and $H-2L^d$ are prepared as discussed in Example 1.B. above.

The cDNAs encoding $K^b$ α1α2α3 domains (274 residues) and murine β2 microgulin (99 residues) were respectively cloned into the unique Bam HI site of an expression vector harboring the metallothionein promoter pRMHa-3 (Bunch, et al., *Nucleic Acid Res.* 16:1043–1061 (1988)). Drosophila S2/M3 cells were transformed with these recombinant plasmids in addition to plasmid phshsneo (containing a neomycin-resistance gene) by the calcium-phosphate precipitation method described previously. The transformed cells selected against neomycin-analog antibiotics G418 were grown at 27° C. in serum-free medium and soluble heavy-chain $K^b$ and β2 microglobulin were co-expressed by the addition of 0.7 mM $CuSO_4$. The soluble, assembled heterodimer of $K^b$ was purified from the culture supernatants by affinity chromatography using anti-$K^b$ monoclonal antibody Y3, followed by ion-exchange chromatography on a Pharmacia Mono Q FPLC column according to the instructions of the manufacturer (Pharmacia, Piscataway, N.J.). SDS-polyacrylamide gel electrophoresis (SDS-PAGE) of the $K^b$ preparation followed by staining with Coomassie blue showed only one band of relative molecular mass (Mr) at about 32,000 and one band of Mr at about 12,000 with no detectable impurities. The highly-purified $K^b$ was dialyzed against phosphate-buffered saline (PBS), filter-sterilized, and used for further study. Extinction coefficient of the soluble $K^b$ ("$K^b$sol") protein (43.2 kDa) is 69,200 $M^{-1}cm^{-1}$ at 280 nm.

The purified $K^b$sol (0.3 μM) in PBS with or without 1% TX-100 were exposed to varying temperatures (i.e., 4°, 23°, 32°, 37°, 42°, and 47° C.) for one hour. The proteins were then immunoprecipitated by incubating with the monoclonal antibody Y3 and protein A sepharose beads (Pharmacia, Piscataway, N.J.) at 4° C. for two hours, respectively. The samples were analyzed by 12.5% SDS-PAGE, followed by staining with Coomassie blue. The two thick bands on the gel are heavy and light chains of antibody Y3. In another procedure, $K^b$sol (0.3 μM) were incubated with 50 μM of peptides in PBS at 23° C. for two hours to allow for $K^b$sol-peptide complex formation. After the addition of 1% TX-100, the samples were exposed to 12° C., 37° C., or 47° C. temperatures for one hour. The complexes were immunoprecipitated and analyzed by SDS-PAGE as described above. In a third procedure, $K^b$sol (2.7 μM) were incubated with 50 μM of OVA-8, VSV-8 or SEV-9 peptides, respectively, at 23° C. for two hours. The samples were applied on a 5% polyacrylamide IEF gel. IEF was run from pH 5–7 and the gel was stained with silver.

Next, VSV-8 peptide was radioiodinated using the chloramine-T method (Hunter, et al., *Nature* 194:495–6 (1962)) and free $^{125}$I was removed by $C_{18}$ column (OPC cartridge, Applied Biosystems, Foster City, Calif.). The labelled peptide was further purified by $C_{18}$ reverse-phase HPLC. After elution, the labelled peptide was lyophilized and resuspended in PBS. The specific activity of [$^{125}$I] VSV-8 (about 250 Ci/mmole) was determined spectrophotometrically by using extinction coefficient of tyrosine at 274 nm (1420 $M^{-1}$ $cm^{-1}$). First, $K^b$sol (0.5 μM) was mixed with [$^{125}$I]VSV-8 (1.5 nM) and unlabelled VSV-8 (50 nM) at 23° C. for 16 hours to allow for complex formation. A portion of the sample was analyzed by gel filtration (Superose 12, Pharmacia, Piscataway, N.J.) in PBS. After elution, radioactivity contained in each fraction (0.05 ml) was measured. Protein was monitored by absorbance at 280 nm. In a second procedure, [$^{125}$I]VSV-8 (0.39 nM) was mixed with various concentrations of $K^b$sol in PBS containing 1% bovine serum albumin (BSA). After incubation at 23° C. for 2–16 hours, $K^b$sol-peptide complexes were separated from free peptide by small gel filtration (Bio-Gel P30, BioRad, Richmond, Calif.) in PBS. P30 gel filtration permitted over 95% separation of bound and free peptide within about 5 minutes. Radioactivity of bound and free peptides was measured and the data were analyzed by linear regression. At maximal levels of K$^b$sol offered, about 65% of the total labelled peptides were bound. This maximal binding capacity of labelled peptide to K$^b$sol protein deteriorated over time, presumably due to radiation by $^{125}$I bound to VSV-8. In a third procedure, each sample contained 0.39 nM of [$^{125}$I]VSV-8 (about 18,000 cpm), unlabelled peptides at the indicated concentration, and 30 nM of K$^b$sol that gives about 50% of the [$^{125}$I]VSV-8 binding in the absence of unlabelled peptide at a final volume of 72μl. All components were dissolved and diluted in PBS containing 1% BSA. After incubation for 2–16 hours at 23° C., 50 μl samples were analyzed by P30 gel filtration as described above. The dissociation constants for unlabelled peptides were determined from molar concentrations of [$^{125}$I]VSV-8 and unlabelled peptides giving 50% inhibition of [$^{125}$I]VSV-8 binding to K$^b$sol as described. (See Muller, et al., *Meth. Enzymol.* 92:589–601 (1983).)

K$^b$sol (0.3 μM) and [$^{125}$I]VSV-8 (0.39 nM) were then incubated at 4° C., 23° C., and 37° C., and the association was determined at various times by P30 gel filtration. Murine β2 microglobulin was added, when necessary, before the incubation at the indicated concentration. The murine β2 microglobulin was prepared by affinity chromatography using anti-β2 microglobulin polyclonal antibody K355 from culture supernatants of the recombinant Drosophila cells. (See also Logdberg, et al., *Molec. Immun.* 14:577–587 (1979).) In another experiment, K$^b$sol (0.3 μM or 18 μM) and [$^{125}$I]VSV-8 (2.4 nM) were incubated at 23° C. for two hours, and the peptide-K$^b$sol complexes were isolated by P30 gel filtration. The samples contained very small amounts of [$^{125}$I]VSV-8 and K$^b$sol complexes (at the maximum, 2.4 nM) and empty K$^b$sol at final concentration of about 50 to 300 nM. To some samples, 3 μM of β2 microglobulin, 3 μM of β2 microglobulin plus 20 μM of unlabelled VSV-8, 20 μM of unlabelled VSV-8, or 1% TX-100 were added. The samples were incubated for various times at 37° C. and the degree of dissociation was determined by passage over P30 columns.

B. Discussion

Class I MHC molecules present antigenic peptides to cytotoxic T lymphocytes. Direct binding of peptide to Class I molecules in vitro has been hampered by either the presence of previously bound peptides at the binding site (Chen and Perham, *Nature* 337:743–5 (1989)) or the lack of binding specificity. (See, e.g., Frelinger, et al., *J. Exp. Med.* 172:827–34 (1990); Choppin, et al., *J. Exp. Med.* 172:889–99 (1990); Chen, et al., *J. Exp. Med.* 172:931–6 (1990).) In vitro analysis of peptide binding to soluble, empty Class I molecules purified from Drosophila cells transformed with truncated H-2K$^b$sol and murine β2 microglobulin genes is disclosed herein. The results demonstrate that peptide binding is very rapid and naturally processed peptides (octapeptides; see, e.g., Van Bleek, et al., *Nature* 348:213–6 (1990); Falk, et al., *Nature* 351:290–6 (1991)) have the highest affinities to K$^b$sol of the nanomolar range and indicate that K$^b$sol complexed with octapeptides are stable, whereas those complexed with slightly shorter or longer peptides are short-lived. Interactions between free heavy chain and β2 microglobulin is basically reversible in the absence of detergent. Peptides spontaneously bind to empty Class I molecules without dissolution of β2 microglobulin. However, excess β2 microglobulin apparently promotes the binding of peptide to empty Class I as a consequence of reassociation of free heavy chain with β2 microglobulin under conditions where the heterodimers are unstable.

Soluble H-2K$^b$ molecules (composed of the α1α2α3 domain of heavy chain) and murine β2 microglobulin, were purified from the culture supernatants of Drosophila cells which were concomitantly transformed with the truncated heavy chain and 2 microglobulin genes. Preliminary experiments suggested that Drosophila cells express Class I MHC molecules devoid of endogenous peptides on the cell surface. Some of the properties of empty Class I molecules include the observation that they are less stable at 37° C. and their structure is stabilized by the binding of peptide. (See, e.g., Schumacher, et al., *Cell* 62:563–7 (1990); Ljunggren, et al., *Nature* 346:476–80 (1990).) To confirm that purified soluble K$^b$ are also empty, their thermal stability in detergent-free solution was examined (data not shown). Surprisingly, the proteins heated for one hour at 47° C. were well recovered by immunoprecipitation using a conformational antibody, Y3. This unexpected result led us to add detergent, 1% Triton X-100 (polyoxyethylene (9) octyl phenyl ether), to the protein solution, since similar experiments to test the stability of Class I molecules have always been conducted in detergent lysates (See Schumacher, et al., cited supra). The results obtained in the presence of detergent show that the purified K$^b$sol is now unstable at 37° C. (data not shown). This and other lines of evidence suggest that K$^b$sol heterodimer disassembles into the heavy chain and β2 microglobulin at elevated temperatures and that detergent may prevent β2 microglobulin from reassociating with dissociated free heavy chain (see below). Second, the possibility of stabilizing purified K$^b$sol with peptides was studied. The results of the first-described experiment demonstrated that the proteins can be stabilized only when they are mixed with octapeptide (vesicular stomatitis virus nucleocapsid protein [VSV-8], see Table 3 below) which is shown to be a naturally processed peptide (see Van Bleek, et al., cited supra). These observations are consistent with the characteristics of empty Class I molecules mentioned above.

Independent support that the purified K$^b$sol molecules are empty is provided by isoelectric focusing (IEF) under native conditions (data not shown). The soluble K$^b$ purified from Drosophila cells exhibited a much simpler pattern than HLA-A2 molecules purified from human lymphoblastoid cell lines (see FIG. 3 in Silver, et al., *Nature* 350:619–22 (1991)). The complicated pattern of HLA-A2 on IEF is presumed to be the result of the presence of heterogeneous peptides bound to the molecules. The simple band of purified K$^b$sol indicates the absence of endogenous peptides. In addition, the incubation of K$^b$sol with antigenic peptides caused the distinct shifts of band on IEF gel, reflecting the change in isoelectric point of K$^b$sol due to the peptide binding. It should be noted that such band-shifting was not observed in HLA-A2 molecules when they were simply mixed with peptides, unless HLA-A2 are incubated with peptides in "reconstituting conditions" after removal of previously bound endogenous peptides. Taken together, these observations on native IEF also indicate that soluble K$^b$ purified from Drosophila cells are empty.

The association of $^{125}$I-labelled VSV-8 with K$^b$sol was demonstrated by gel filtration (not shown). The radioactivity of high molecular weight materials corresponds to peptide-K$^b$sol complexes, while that of low molecular weight materials represents free peptides. Unlabelled VSV and ovalbumin (OVA) peptides could compete with the labelled VSV-8 (see below), arguing that [$^{125}$I]VSV-8 is bound specifically to K$^b$sol molecules. Reversed-phase HPLC revealed that K-bound [$^{125}$I]VSV-8 has the identical retention time to the input peptide. The binding to K$^b$sol of the labelled VSV-8 was saturable, exhibiting a dissociation constant (K$_D$) of about 33 nM (not shown). From the x-axis of the Scatchard plot, it was noted that about 65% of the labelled VSV-8 is able to bind to $K^b$.

To determine affinities of various peptides to $K^b$, competitive radioimmunoassays (RIA) using [$^{125}$I]VSV-8 were carried out (data not shown). The inhibitory peptides used for the RIA are listed in Table 3. $K_D$ for each peptide is summarized in Table 3 as well.

TABLE 3

Various Antigenic Peptides* Used in Present Studies

| Code | Sequence | $K_D$(M) |
|---|---|---|
| VSV-7 | GYVYQGL | $5.3 \times 10^{-8}$ |
| VSV-8 | RGYVYQGL | $3.7 \times 10^{-9}$ |
| VSV-9N | LRGYVYQGL | $7.3 \times 10^{-9}$ |
| VSV-10N | DLRGYVYQGL | $3.9 \times 10^{-7}$ |
| VSV-9C | RGYVYQGLK | $6.9 \times 10^{-9}$ |
| VSV-10C | RGYVYQGLKS | $2.1 \times 10^{-8}$ |
| OVA-8 | SIINFEKL | $4.1 \times 10^{-9}$ |
| OVA-9N | ESIINFEKL | $8.9 \times 10^{-8}$ |
| OVA-10N | LESIINFEKL | $2.8 \times 10^{-7}$ |
| OVA-9C | SIINFEKLT | $1.1 \times 10^{-8}$ |
| OVA-10C | SIINFEKLTE | $1.4 \times 10^{-8}$ |
| OVA-24 | EQLESIINFEKLTEWTSSNVMEER | $7.1 \times 10^{-5}$ |
| SEV-9 | FAPGNYPAL | $2.7 \times 10^{-9}$ |

VSV-8: Vesicular stomatitis virus nucleocapsid protein 52-59 (Van Bleek, et al., Nature 348: 213–216 (1990))
OVA-8: Ovalbumin 257–264 (Carbone, et al., J. Exp. Med. 169: 603–12 (1989));
SEV-9: Sendai virus nucleoprotein 324–332 (Schumacher, et al., Nature 350: 703–706 (1991))
*All peptides were purified by $C_{18}$ reversed-phase HPLC to exclude contaminating shorter peptides with different binding properties. The 3-letter code designations and SEQ ID NO for each peptide are given below.

| VSV-7 | GlyTyrValTyrGlnGlyLeu (SEQ ID NO 24, residue nos. 4–10) |
| VSV-8 | ArgGlyTyrValTyrGlnGlyLeu (SEQ ID NO 24, residue nos. 3–10) |
| VSV-9N | LeuArgGlyTyrValTyrGlnGlyLeu (SEQ ID NO 24, residue nos. 2–10) |
| VSV-10N | AspLeuArgGlyTyrValTyrGlnGlyLeu (SEQ ID NO 24) |
| VSV-9C | ArgGlyTyrValTyrGlnGlyLeuLys (SEQ ID NO 35, residue nos. 1–9) |
| VSV-10C | ArgGlyTyrValTyrGlnGlyLeuLysSer (SEQ ID NO 35) |
| OVA-8 | SerIleIleAsnPheGluLysLeu (SEQ ID NO 23, residue nos. 5–12) |
| OVA-9N | GluSerIleIleAsnPheGluLysLeu (SEQ ID NO 23, residue nos. 4–12) |
| OVA-10N | LeuGluSerIleIleAsnPheGluLysLeu (SEQ ID NO 23, residue nos. 3–12) |
| OVA-9C | SerIleIleAsnPheGluLysLeuThr (SEQ ID NO 23, residue nos. 5–13) |
| OVA-10C | SerIleIleAsnPheGluLysLeuThrGlu (SEQ ID NO 23, residue nos. 5–14) |
| OVA-24 | GluGlnLeuGluSerIleIleAsnPheGluLysLeuThrGlu-TrpThrSerSerAsnValMetGluGluArg (SEQ ID NO 23) |
| SEV-9 | PheAlaProGlyAsnTyrProAlaLeu (SEQ ID NO 36) |

The peptides of naturally processed size (8 mer for VSV and OVA, and 9 mer for sendai virus nucleoprotein [SEV]) had the highest and remarkably similar affinities from the range of 2.7 to 4.1 nM. this exceedingly high affinity of the natural peptides is consistent with recent observations. (See, e.g., Schumacher, et al., Nature 350:703–6 (1991); Christnick, et al., Nature 352:67–70 (1991).) However, peptides that were shorter or longer by as little as one or two residues lowered the affinity by a factor of from 2 to 100. This reduction of the affinity is even more drastic for a much longer peptide; i.e., the affinity of 24 mer peptide (OVA-24) is more than 10,000-fold lower than that of OVA-8. These results help to explain why earlier reports using longer peptides claim the affinity of micromolar range. (See, e.g., Frelinger, et al. and Choppin, et al., both cited supra.) It is of particular interest that the extension of peptides at the carboxyl terminus is much less destructive of the affinity than extension at the amino terminus. According to the three-dimensional structure of HLA-A2, the peptide-binding groove is formed by two long α helices on the antiparallel β strands, and the cleft is about 25 angstroms long, which is proposed to accommodate an extended peptide chain of about eight residues (see, e.g., Bjorkman, et al., Nature 329:506–12 (1987)). At one end of the cleft, the 1 and 2 helices come close together tightly, while at the other end, the cleft is fairly open. It is now speculated that both VSV and OVA peptide bind to the cleft in the same orientation and the carboxyl terminus of the peptides might interact with the relatively open end of the cleft so that the extension of peptide at the carboxyl terminus does not cause severe steric hindrance.

Experiments were then performed to examine the rate of peptide binding to $K^b$ at 4° C. and 23° C., respectively (not shown). Binding was very rapid, especially at 23° C., with a half-time of about 5 minutes even in extremely low concentrations of labelled peptides (about 0.4 nM). This contrasts with previous observations, which show a half-time of association of about two hours. (See, e.g., Choppin, et al., cited supra.) Again, only 65% of the total labelled peptide was able to bind. The addition of excess β2 microglobulin did not affect the peptide-binding kinetics at such low temperatures that $K^b$ heterodimer is stable (remained to be assembled). This implies that exchange of β2 microglobulin is not a prerequisite for peptide binding; i.e., peptides can spontaneously bind to empty Class I molecules without dissociation of β2 microglobulin. In contrast, excess free β2 microglobulin apparently promotes peptide binding at 37° C. (data not shown). As the concentration of added β2 microglobulin increased, more peptides bound to $K^b$ molecules. Since empty $K^b$ are unstable at 37° C., a fraction of heterodimers must be dissociated to the heavy chain and β2 microglobulin and thereby, the heterodimer must be in equilibrium with free heavy chain and free β2 microglobulin. Then, the addition of β2 microglobulin should shift the equilibrium toward the formation of heterodimer that can bind peptides. This view is supported by recent observations that there are substantial numbers of Class I free heavy chains on the normal cell surface and exogenously added β2 microglobulin facilitates peptide binding to empty Class I molecules on cells as a consequence of the reassociation of β2 microglobulin with free heavy chain. (See, e.g., Rock, et al., Cell 65:611–620 (1991); Kozlowski, et al., Nature 349:74–77 (1991); Vitiello, et al., Science 250:1423–6 (1990).)

The dissociation kinetics of peptide at 37° C. were then observed. Immediately after isolating [$^{125}$I]VSV-8 and $K^b$ complexes by gel filtration, the samples containing either 50 or 300 nM $K^b$ were exposed to 37° C. temperatures. Some samples were supplemented with 3 μM β2 microglobulin and/or 20 μM unlabelled VSV-8, or 1% TX-100. The dissociation of labelled peptides from $K^b$ was measured at various times (not shown). In the presence of a large excess of unlabelled peptides, the dissociation rate of peptide followed first-order kinetics with a half-time dissociation of about 36 minutes (a dissociation rate constant of $3.2 \times 10^{-4}$ s$^{-1}$). This unexpected, relatively rapid dissociation of labelled peptide does not agree with some current views of stable peptide-Class I complexes. In fact, the results ascertained (not shown) demonstrated that $K^b$ and VSV-8 complexes are stable. This discrepancy must arise from the 10-fold lower affinity of radiolabelled VSV-8 (33 nM) compared with that of unlabelled VSV-8 (3.7 nM).

The first-order kinetics were also observed when the detergent was added instead of unlabelled peptide, indicating that the detergent makes the peptide dissociation process irreversible. In contrast, the peptide dissociation profile did not follow the first-order kinetics in the absence of unlabelled peptide or the detergent. This suggests that the peptide association/dissociation is reversible and the binding of peptide is dependent on the concentration of heterodimer (compare the kinetics between 50 nM and 300 nM of Kb). This became more evident when excess β2 microglobulin was added. These results support the previous argument that interaction between the heavy chain, β2 microglobulin and peptide are basically reversible at 37° C., if not entirely, in the absence of detergent. It is probable that a detergent such as TX100 may prevent β2 microglobulin from reassociating with free heavy chain at 37° C. This could reasonably explain why $K^b$ once heated to elevated temperatures in the absence of detergent can be efficiently immunoprecipitated by conformational antibody (not shown). Interestingly, the addition of β2 microglobulin did not suppress the peptide dissociation in the presence of excess unlabelled peptides, indicating that labelled peptides are released from the complexes without dissociation of β2 microglobulin. It should be remembered, however, that the affinity of $[^{125}I]$VSV-8 is about 10-fold lower than that of the natural peptides. Therefore, this is not necessarily the case for the natural peptides.

The study using in vitro peptide-binding assay systems suggests that peptide binding to Class I molecules is a simple mass action and a ligand-receptor interaction. The approach used herein allows characterization of the peptide binding specificity to Class I molecules and of the interaction of peptide-Class I complexes with the T cell receptor.

Example 6

Therapeutic Applications

A. Class I Molecule Bank

A reservoir or "bank" of Drosophila cell lines may be established and maintained, with each cell line expressing one of the 50 to 100 most common Class I molecules. cDNAs encoding these proteins may be cloned based on HLA variants obtained from cell lines containing same— e.g., via the polymerase chain reaction (see Ennis, et al., *PNAS USA* 87:2833–7 (1990))—and inserted into the appropriate vector, such as an insect expression vector, to generate cell lines expressing each HLA variant. Testing according to the following protocol, for example, can be used to determine which peptides derived from the virus of choice bind the best to the different Class I molecules. The various cultures may appropriately be labeled or catalogued to indicate which Class I molecules are best for use with particular peptides. Alternatively, transient cultures may be established as needed. As discussed herein, after approximately 48 hours' incubation of a culture of insect cells with a vector, that culture is apparently capable of expressing empty MHC molecules which may be loaded with the peptide(s) of choice for the purpose of activating CD8 cells.

B. Preparation of "Special" Cell Lines

After HLA typing, if Drosophila cells expressing the preferred HLA are not available, cDNAs encoding the preferred HLA may be cloned via use of the polymerase chain reaction. The primers disclosed in section B.1. above (SEQ ID NO 1 through SEQ ID NO 12) may be used to amplify the appropriate HLA-A, -B, -C, -E, -F, or -G cDNAs in separate reactions which may then be cloned and sequenced as described in the methods disclosed in Example 1, section 1 above. DNA is then purified from the PCR reaction using a Gene Clean kit (Bio 101, San Diego, Calif.) and ligated directly into the Sma I site of pRmHa-3. Individual clones are isolated, the sequences verified, and stable Drosophila cell lines expressing the HLA established. Alternatively, a bulk population of recombinant plasmids may be grown in large scale and DNA purified by cesium chloride gradients. The purified DNA is then used to transfect Schneider cells using calcium phosphate precipitation techniques. After 24 hours, the precipitate is washed off the cells and replaced with fresh Schneider media containing 1 mM $CuSO_4$. Forty-eight hours later, the bulk population of transiently transfected cells is used for in vitro activation of CD8 after incubation with syngeneic peptides or protease digests of specific proteins.

Stable cell lines expressing the cloned HLA may then be established in the Drosophila cells. Alternatively, a population of insect cells transiently expressing a bulk population of cloned recombinant molecules from the PCR reaction may be used for in vitro CD8 activation.

It is also possible to activate haplotype-specific CD8s in vitro using insect cells expressing class I MHC incubated with peptides where the cell line-expressed MHC is not the expressed element in vivo. This provides a unique opportunity to proliferate CD8 cells which recognize a specific antigen associated with a particular MHC which would not be possible in vivo due to allelic restriction. For example, a peptide (NP) from the nuclear protein of Influenza virus is ordinarily restricted to the $D^b$ molecule; however, we have found that such a peptide can bind to $K^b$ (albeit more weakly than to $D^b$) and can generate a degree of thermal stability to the $K^b$ (see FIG. 3). Furthermore, $K^b$-expressing Drosophila cells preincubated with the NP peptide and cocultured with splenocytes from a B6 mouse results in the in vitro activation of CD8 which specifically recognize the $K^b$ molecule associated with the NP peptide. In addition, the reciprocal experiment using a $K^b$-restricted peptide (OVA) derived from ovalbumin and $D^b$-expressing Drosophila cells results in the proliferation of CD8 which specifically recognize $D^b$ containing the OVA peptide. Such CD8s are able to kill cells (EL4 OVA) transfected with cDNA encoding the ovalbumin protein, indicating that in vivo, some $D^b$ molecules are loaded with the OVA peptide.

This system therefore provides a unique opportunity to proliferate CD8 against specific antigens presented by a Class I molecule which, in vivo, is not the restriction element for that peptide. Although enough antigen is presented in vivo by said class I for the cell to be recognized by CD8 and killed, it is not enough to proliferate such CD8s in vivo. By loading empty Class I molecules expressed by Drosophila cells with peptide, we are presumably able to override the in vivo restriction by providing an excess of antigenic peptide to the Class I molecule in a non-competitive environment such that enough antigen is presented by the Class I to activate the specific CD8 recognizing this complex.

C. AIDS Treatment

In vitro activated cells may be administered to patients for in vivo therapy. Preferably, the Class I genotype (haplotype) of the individual is first determined. Conventional tissue typing is appropriate for this purpose and may be performed at the treatment center or by some appropriate commercial operation. Once the individual's HLA type(s) is (are) determined, the best combination of peptides and Class I molecules suitable for the individual patient is ascertained and prepared as noted above and the appropriate Drosophila cells and peptides are provided for treatment of the patient. Resting or precursor CD8 (T) cells from the blood of the patient are then stimulated with the appropriate peptide-loaded MHC produced by the Drosophila cell culture. After activation, the CD8 cells are reintroduced into the patient's bloodstream, and the disease process in the patient continues to be monitored. Methods of removing and re-introducing cellular components are known in the art and include procedures such as those exemplified in U.S. Pat. No. 4,844,893 to Honsik, et al. and U.S. Pat. No. 4,690,915 to Rosenberg.

Additional treatments may be administered as necessary until the disease is sufficiently remediated. Similar treatment protocols are appropriate for use with other immunosuppressed individuals, including transplant patents, elderly patients, and the like.

D. Cancer Treatment

In cancer patients, a treatment procedure similar to that described above is utilized. However, in such patients, it should be anticipated that conventional therapy to reduce the tumor mass may precede the immune therapy described herein. Therefore, it is preferred that blood samples from the putative patient be obtained and stored (e.g. via freezing) prior to the commencement of conventional therapy such as radiation or chemotherapy, which tends to destroy immune cells. Since few, if any, forms of cancer arise in direct response to viral infection, target peptides for immune treatment are less readily observed. However, recent studies indicate that mutations in the oncogenes ras, neu, and p53 contribute to cancer in as much as 50% of all cancer cases. Thus, peptides derived from these mutated regions of the molecules are prime candidates as targets for the present therapy. Pursuant to the protocols disclosed herein, the best combination of peptides and Class I molecules for the individual patient may be determined and administered.

For example, many tumors express antigens that are recognized in vitro by CD8 cells derived from the affected individual. Such antigens which are not expressed in normal cells may thus be identified, as well as the HLA type that presents them to the CD8 cells, for precisely targeted immunotherapy using the methods of the present invention. For example, van der Bruggen, et al. have described an antigen whose expression is directed by a specific gene and which antigen appears to be presented by HLA A1 (*Science* 254:1643–1647 (1991)). As various human tumor antigens are isolated and described, they become good candidates for immunotherapeutic applications as described herein.

E. Combined Therapies/Conjugates

The soluble, "empty" Class I molecules may further be conjugated with toxic proteins (e.g., pseudomonas toxin) for the treatment or removal of activated CD8 cells that are undesired—i.e., those which are capable of stimulating transplant rejection. Conjugates are constructed and then the Class I molecule portion is loaded with the appropriate peptide, which then "attracts" or "seeks out" the T cells with receptors for the Class I molecule-peptide combination, so that antigen-specific CD8 cells may be eliminated. This approach also may eliminate those T cells which are responsible for transplant rejection. For example, one such procedure may include the following steps: (1) isolate soluble, empty, human Class I MHC molecules from a culture of Drosophila cells; (2) link the empty human Class I MHC molecules to a toxin in vitro; (3) contact, in vitro, the empty, linked Class I MHC molecules with antigenic peptides (e.g., peptides derived from a transplanted tissue) for a time period sufficient to load the MHC molecules with peptide; (4) isolate the peptide-loaded, linked molecules; and (5) administer the peptide-loaded molecules to an individual in need of treatment, for example, one who has undergone a transplant procedure.

Likewise, certain discrete T cell populations have been implicated as the cause of diabetes, rheumatoid arthritis and other putative autoimmune disorders. Such cells may also be selectively eliminated by the above-noted procedure. The application of this protocol to allergy patients should also be considered.

In another, alternative therapeutic mode, it may be feasible to administer the in vitro activated CD8 cells of the present invention in conjunction with other immunogens. For example, the Large Multivalent Immunogen disclosed in U.S. Pat. No. 5,045,320 may be administered in conjunction with activated CD8 cells.

It is also contemplated that cytokines such as IL2 and IL4, which mediate differentiation and activation of T cells, may be administered as well, as cytokines are able to stimulate the T cell response against tumor cells in vivo. It is believed that IL2 plays a major role in the growth and differentiation of CTL (CD8) precursors and in CD8 proliferation. The administration of IL2 to cancer patients is frequently associated with an improved anti-tumor response which is likely related to induction of tumor-specific T cells. However, the best therapeutic effects of IL2 might be obtained by continuous local rather than systemic administration of IL2, thus minimizing the IL2 toxicity and prolonging its biological activity. Thus, it is suggested herein that one may achieve local delivery via transfecting tumor cells with an IL2 gene construct.

IL2 cDNA is constructed as described by Karasuyama and Melchers in *Eur. J. Immunol.* 18:97–104 (1988). The complete cDNA sequence of IL2 is obtained as an Xho I fragment from the plasmid pBMGneo IL2 (see Karasuyama and Melchers, supra) and directly ligated into the Sal I site in pRmHa-3. Recombinant pRmHa-3 plasmid with the insert in the correct orientation (determined via restriction mapping with Hind III) is purified by cesium gradients and used to cotransfect Schneider 2 cells using the calcium phosphate technique. (A mixture of plasmid DNA was prepared for this purpose: 10 µg pRmHa-3 containing IL2 cDNA, 6 µg each of pRmHa-3 plasmid containing MHC Class I heavy chain or β2 microglobulin and 2 µg of phshsneo DNA.) Stable cell lines which are inducible via $CuSO_4$ to express heavy chain, β2 microglobulin and IL2 were obtained by growing the transfectants in G418 medium. These stable cell lines were coated with peptide and used in the in vitro assay as described above. Tumor cells transfected with IL2 are observed to enhance the CTL (CD8) activity against the parental tumor cells and bypass CD4 and T helper function in the induction of an antitumor or cytotoxic response in vivo. Therefore, increasing the potential of the Drosophila system via cotransfection with the IL2 gene is suggested herein.

The foregoing is intended to be illustrative of the present invention, but not limiting. Numerous variations and modifications may be effected without departing from the true spirit and scope of the invention.

---

We claim:

1. A method for activating $CD8^+$ T-cells against a selected peptide in vitro, the method comprising:

(a) providing a stable insect cell line comprising:

(1) a human class I MHC gene, operably linked to an inducible promoter, capable of expressing a human class I MHC antigen on induction of the promoter;

(2) a human β-2-microglobulin gene, operably linked to a second inducible promoter, capable of expressing a human β-2-microglobulin protein, on induction of the second promoter;

(3) wherein the stable insect cell line is capable of assembling the MHC class I antigen and the β-2-microglobulin protein into empty complexes, and transporting and anchoring the empty complexes to the surface of the cell in sufficient numbers to activate a population of $CD8^+$ T-cells against the selected peptide when the peptide is bound to the complexes;

(b) culturing the stable insect cell line under conditions such that the first and second promoters are induced and the empty complexes are produced on the surface of the cell line;

(c) contacting the stable insect cell line with the selected peptide to form peptide-bound complexes on the surface of the cell line; and (d) contacting the peptide-bound complexes with the $CD8^+$ T-cells for a time sufficient to activate the $CD8^+$ T-cells against the selected peptide.

2. The method of claim 1, wherein the stable insect cell line is a Drosophila cell line.

3. The method of claim 1, wherein the stable insect cell line is an armyworm cell line.

4. The method of claim 3, wherein the armyworm cell line is ATCC CRL 1711.

5. The method of claim 1, wherein the stable insect cell line is a moth, silkworm or mosquito cell line.

6. The method of claim 1, further comprising the step of separating the activated CD8$^+$T-cells from the stable insect cell line.

7. The method of claim 6, further comprising the step of adding the activated CD8$^+$T-cells to an acceptable carrier or excipient to form a suspension.

8. The method of claim 1, wherein the first and second promoters are metallothionein promoters.

9. The method of claim 1, wherein the human class I MHC gene and the human β-2-microglobulin gene are integrated in the genome of the stable insect cell line.

10. The method of claim 1, wherein the human class I MHC gene and the human β-2-microglobulin gene are operably linked to polyadenylation sequences.

11. The method of claim 1, wherein the human class I MHC antigen is B7, B27 or A2.1.

12. The method of claim 1, wherein the peptide is derived from a human immunodeficiency virus protein.

* * * * *

UNITED STATES PATENT AND TRADEMARK OFFICE
CERTIFICATE OF CORRECTION

PATENT NO. : 5,529,921
DATED : June 25, 1996
INVENTOR(S) : Peterson et al.

Page 1 of 1

It is certified that error appears in the above-identified patent and that said Letters Patent is hereby corrected as shown below:

Column 1,
Line 6, insert -- This invention was made with government support under Contract No. CA 27489-14 by the National Institutes of Health. The government has certain rights in the invention. --

Signed and Sealed this

Twelfth Day of March, 2002

Attest:

JAMES E. ROGAN
Attesting Officer
Director of the United States Patent and Trademark Office